United States Patent [19]
Berman et al.

[11] Patent Number: 5,853,978
[45] Date of Patent: Dec. 29, 1998

[54] MOLECULARLY CLONED ACQUIRED IMMUNODEFICIENCY SYNDROME POLYPEPTIDES AND METHODS OF USE

[75] Inventors: Phillip W. Berman, Burlingame; Daniel J. Capon, San Mateo; Laurence A. Lasky, San Francisco, all of Calif.

[73] Assignee: Genentech, Inc., San Francisco, Calif.

[21] Appl. No.: 282,857

[22] Filed: Jul. 29, 1994

Related U.S. Application Data

[63] Continuation of Ser. No. 129,009, Sep. 29, 1993, abandoned, which is a continuation of Ser. No. 979,391, Nov. 19, 1992, abandoned, which is a continuation of Ser. No. 227,568, Aug. 2, 1988, abandoned, which is a division of Ser. No. 861,016, May 8, 1986, abandoned, which is a continuation-in-part of Ser. No. 805,069, Dec. 4, 1985, abandoned, which is a continuation-in-part of Ser. No. 685,272, Dec. 24, 1987, abandoned.

[51] Int. Cl.$^6$ .............................. C12Q 1/70; C12P 21/06; C12P 21/04; C07K 1/00
[52] U.S. Cl. ........................... 435/5; 435/69.3; 435/69.7; 530/395; 530/350
[58] Field of Search ................................ 435/69.7, 69.3, 435/5; 530/395

[56] References Cited

U.S. PATENT DOCUMENTS

| | | |
|---|---|---|
| 4,520,113 | 5/1985 | Gallo et al. . |
| 4,571,421 | 2/1986 | Itakura . |
| 4,703,004 | 10/1987 | Hopp et al. . |
| 4,707,439 | 11/1987 | Seto et al. . |
| 4,732,852 | 3/1988 | Cohen et al. . |
| 4,753,873 | 6/1988 | Beltz et al. . |
| 4,755,465 | 7/1988 | Gray et al. . |
| 4,772,547 | 9/1988 | Heimer et al. . |
| 4,774,175 | 9/1988 | Chang et al. . |
| 4,784,941 | 11/1988 | Watanabe et al. . |
| 4,808,536 | 2/1989 | Chang et al. . |
| 4,855,224 | 8/1989 | Berman et al. . |
| 4,861,707 | 8/1989 | Ivanoff et al. . |
| 4,886,747 | 12/1989 | Derynck et al. . |
| 4,952,512 | 8/1990 | Loskutoff et al. . |
| 4,963,495 | 10/1990 | Chang et al. . |

FOREIGN PATENT DOCUMENTS

| | | |
|---|---|---|
| 82/16819 | 4/1984 | Canada . |
| 0013828 | 8/1980 | European Pat. Off. . |
| 0075395 | 8/1982 | European Pat. Off. . |
| 139417 | 5/1985 | European Pat. Off. . |
| 173529 | 3/1986 | European Pat. Off. . |
| Kokai 61110 | 4/1982 | Japan . |
| WO 85/04903 | 7/1985 | WIPO . |
| WO 88/04692 | 6/1988 | WIPO . |

OTHER PUBLICATIONS

Arya et al., "Three Novel Genes of Human T-Lymphotropic Virus Type III: Immune reactivity of their products with sera from acquired immune deficiency patients", *Proc. Natl. Acad. Sci.*, 83:2209–2213 (1986).

Brun–Vezinet et al., "Prealence of Antibodies to Lymphadenopathy–Associated Retrovirus in African Patients with AIDS", *Science*, 226:453–456 (1984).

Cabradilla et al., "Serodiagnosis of Antibodies to the Human AIDS Retrovirus with a Bacterially Synthesized env Polypeptide", *Bio/Technology*, 4:128–133 (1986).

DiCioccio et al., "Structure–Activity Relationships and Specificity of Inhibition of DNA Polymerases From Normal and Leukemia Cells of Man and From Simian Sarcoma Virus by Rifamycin Derivatives", *J. Natl. Cancer Inst.*, 61(5):1187–1194 (1978).

Dowbenko et al., "Bacterial expression of the acquired immunodeficiency syndrome retrovirus p24 gag protein and its use as a diagnostic reagent", *Proc. Natl. Acad. Sci.*, 82:7748–7752 (1985).

Ghrayeb et al., "Human T–Cell Lymphotropic Virus Type III (HTLV–III) Core Antigens: Synthesis in *Escherichia coli* and Immunoreactivity with Human Sera", 5(2):93–99 (1986).

Groopman et al., "HTLV–III in Saliva of People with AIDS–Related Complex and Healthy Homosexual Men at Risk for AIDS", *Science*, 226:447–449 (1984).

Gurgo et al., "Rifamycin Derivatives Strongly Inhibiting RNA→DNA Polymerase (Reverse Transcriptase) of Murine Sarcoma Viruses", *J. Natl. Cancer Inst.*, 49:61–79 (1972).

Hahn et al., "Molecular cloning and characterization of the HTLV–III Virus associated with AIDS", *Nature*, 312:166–169 (1984).

Hu et al., "Expression of AIDS virus envelope gene in recombinant vaccinia viruses", *Nature*, 320:537–540 (1986).

Kalyanaraman et al., "Antibodies to the Core Protein of Lymphadenopathy–Associated Virus (LAV) in Patients with AIDS", *Science*, 225:321–323 (1984).

Kiyokawma et al., "Envelope proteins of human T–cell leukemia virus: Expression in *Escherichia coli* and its application to studies of env gene functions", *Proc. Natl. Acad. Sci.*, 81:6202–6206 (1984).

Lasky et a., "Neutralization of the AIDS Retrovirus by Antibodies to a Recombinant Envelope Glycoprotein", *Science*, 233:209–212 (1986).

(List continued on next page.)

*Primary Examiner*—Lynette F. Smith
*Attorney, Agent, or Firm*—Timothy E. Torchia

[57] ABSTRACT

Diagnostic product and vaccine for Acquired Immunodeficiency Syndrome (AIDS) and methods for making and using same, wherein viral polypeptide sequences from an AIDS associated retrovirus are expressed directly or as a fusion polypeptide in a prokaryotic or mammalian cell expression host to produce a diagnostic product which specifically binds complementary antibody produced by individuals afflicted with AIDS or a vaccine against AIDS which confers resistance to infection by AIDS associated retrovirus. The reverse transcriptase of an AIDS associated retrovirus is used separately or in a whole cell assay to identify compounds which selectively inhibit retroviral reverse transcriptase.

14 Claims, 25 Drawing Sheets

OTHER PUBLICATIONS

Lasky et al., "Protection of mice from Lethal herpes simplex virus infection by vaccination with a secreted form of cloned glycoprotein D", *Bio/Technology*, 2:527–532 (1984).

Mackay et al., "Production of immunologically active surface antigens of hepatitis B virus by *Escherichia coli*", *Proc. Natl. Acad. Sci. USA*, 78:4510–4514 (1981).

Meusing et al., "Nucleic acid structure and expression of the human AIDS/Lymphadenopathy retrovirus", *Nature*, 313:450–458 (1985).

Mitsuya, H. et al., "Suramin Protection of T Cells in Vitro Against Infectivity and Cytopathic Effect of HTLV–III", *Science*, 226:172–174 (1984).

Montagnier et al., "A new type of retrovirus isolated from patients presenting with Lymphadenopathy and acquired immune deficiency syndrome: structural and antigenic relatedness with equine infectious anaemia virus", *Ann. Virol.*, 135E:119–134 (1984).

Poiesz et al., "Detection and isolation of type C retrovirus particles from fresh and cultured Lymphocytes of a patient with cutaneous T–cell Lymphoma", *Proc. Natl. Acad. Sci.*, 77(12):7415–7419 (1980).

Rey et al., "Characterization of the RNA dependent DNA polymerase of a new human T Lymphotropic retrovirus (Lymphadenopathy associated virus)", *Biochem, Biophys. Res. Comm.*, 121(1):126–133 (1984).

Schupbach et al., "Serological Analysis of a Subgroup of Human T–Lymphotropic Retroviruses (HTLV–III) Associated with AIDS", *Science*, 224:503–505 (1984).

Shaw et al., "Molecular Characterization of Human T–Cell Leukemia (Lymphotropic) Virus Type III in the Acquired Immune Deficiency Syndrome", *Science*, 226:1165–1171 (1984).

Steimer et al., "Differential Antibody Responses of Individuals Infected with AIDS–Associated Retroviruses Surveyed Using the Viral Core Antigen $p25^{gag}$ Expressed in Bacteria", *Virology*, 150:283–290 (1986).

Tabin et al., "Adaption of a Retrovirus as a Eucaryotic Vector Transmitting the Herpes Simplex Virus Thymidine Kinase Gene", *Molecular and Cellular Biology*, 2(4):426–436 (1982).

Weinstock et al., "Open reading frame expression vectors: A general method for antigen production in *Escherichia coli* using protein fusions to β–galactosidase", *PNAS*, 80:4432–4436 (1983).

Yang et al., "Rifamycin Antibiotics: Inhibitors of Rausher Murine Leukemia Virus Reverse Transcriptase and of Purified DNA Polymerase From Human Normal and Leukemic Lymphoblasts", *J. Natl. Cancer Inst.*, 49:7–25 (1972).

Chakrabarti, et al, "Expression of the HTLV–III envelope gene by a recombinant", Nature 330:535–537, 1986.

FIG. 1

```
(Pro) Iso (Val) glu Asn Ile Gln Gly Gln Met Val (His) Gln Ala Ile ── Pro
                      5                  10              15
 CCT  ATA  GTG  CAG AAC ATC CAG GGG CAA ATG GTA CAT CAG GCC
```

```
1001  ILEALAPROGLYGLNMETARGGLUPROARGGLYSERASPILEALAGLYTHRTHRSERTHRLEUGLNGLUGLNILEGLYTRPMETTHRASNASNPROPRO
      TATTGCACCAGGCCAGAGATGAGAGACCAAGGGGAAGTGACATAGCACTAGTACCCTTCAGGAACAAATAGGATGGATGACAAATAATCCACCT-

1101  ILEPROVALGLYGLUILETYRLYSARGTRPILEILELEUGLYLEUASNLYSILEVALARGMETTYRSERPROTHRSERILELEUASPILEARGGLNGLYPRO
      ATCCCAGTAGGAGAGAAATTTATAAAGATGGATAATCCTGGGATTAATAAAATAGTAAGAATGTATAGCCCTACCAGCATTCTGGACATAAGACAAGGAC-
                                                ARG
                                                ARG
1201  LYSGLUPROPHEARGASPTYRVALASPARGPHETYRLYSTHRLEUARGALAGLUGLNALASERGLNGLUVALLYSASNTRPMETTHRTHRGLUTHRLEULEU
      CAAAAGAACCCTTTAGAGACTATGTAGACCGGTTCTATAAAACTCTAAGAGCCGAGCAAGCTTCACAGGAGGTAAAAAATTGGATGACAGAAACCTTGTT-
                                                                                                          G
1301  VALGLNASNALAASNPROASPCYSLYSTHRILELEULYSALALEUGLYPROALAALATHRLEUGLUGLYMETMETTHRALACYSGLNGLYVALGLY
      GGTCCAAAATGCGAACCCAGATTGTAAGACTATTTTAAAAGCATTGGGACCAGCAGCTACACTAGAAGAGAATGATGACACATGTCAGGGAGTGGGAGGA-

1401  PROGLYHISLYSALAARGVALLEUEUALAGLUALAMETSERGLNVALTHRASNTHRALATHRILEMETMETGLNARGGLYASNPHEARGASNGLNARGLYSMET
      CCCGGCCATAAGGCAAGAGTTTTGGCTGAAGCAATGAGCCAAGTAACACAATACAGCTACCATAATGATGCAGAGAGGCAATTTTAGGAACCAAAGAAAGA-

1501  VALLYSCYSPHEASNCYSGLYLYSGLUGLYHISTHRALAARGASNCYSARGALAPROARGLYSLYSGLYCYSTRPLYSCYSGLYLYSGLUGLYHISGLN
      TGGTTAAGTGTTTCAATTGTGGCAAAGAAGGGCACACAGCCAGAAATTGCAGGGCCCCTAGGAAAAAAGGGCTGTTGGAAATGTGGAAAGGAAGGACACCA-
                                                               pol
                                                               ┌──► 
                                                               GLYARGSERALAPHELEUGLNGLYLYSALAARGGLUPHESERSERGLUGLNTHRARGALAASN
1601  METLYSASPCYSTHRGLUARGGLNALAASNPHELEUGLNGLYLYSILECYSLEUPROTHRARGGLUGLYGLNGLYILEPHEPHEARGALAASPGLNSERGLN
      AATGAAAGATTGTACTGAGAGACAGGCTAATTTTTTAGGGAAGATCTGCCTTCCTACAAGGGAAGGGCAGGGAATTTCTTCAGAGCAGACCAGAGGCCAA-
                                                                                                     LEU
1701  SERPROTHRILESERSERGLUGLNTHRARGALAASNSERPROTHRARGARGGLULEUGLNVALTRPGLYARGASPASNASNSERPROSERGLUALAGLY
      CAGCCCCACCATTTCTTCAGAGGAACAGAGAGCCAACAGCCCCACCAGAAGAGAGCTTCAGGTCTGGGGTAGAGACAACAACTCCCCTCCAGAAGCAGGA-
                                                                                T
1801  ALAASPARGGLNGLYTHRVALSERPHEASNPHEPROGLNILETHRLEULYSILEGLYLEULYSGLUALALEU
      GCCGATAGACAAGGAACTGTATCCTTTAACTTCCCTCAGATCACTCTTTGGCAACGACCCCTCGTCACAATAAAGATAGGGGGGCAACTAAAGGAAGCTC- 1901  LEUASPTHRGLYALAASPASPTHRVALLEUGLUGLUMETSERLEUPROGLYARGTRPLYSPROLYSMETILEGLYGLYILEGLYGLYPHEILELYSVAL
      TATTAGATACAGGAGCAGATGATACAGTATTAGAGGAAATGAGTTTGCCAGGAAGATGGAAACCAAAAATGATAGGGGGAATTGGAGGTTTTATCAAAGT-
```

FIG. 2C

```
         ARGGLNTYRASPGLNILEGLULEGLUILECYSGLYHISLYSALAILEGLYTHRVALLEUVALGLYPROTHRPROVALASNILEILEGLYARGASNLEU
    2001 AAGACAGTATGATCAAATACTCATAGAAATCTGTGGACATAAAGCTATAGGTACAGTATTAGTAGGACCTACACCTGTCAACATAATTGGAAGAAATCTG
                                        G

LEUTHRGLNILEGLYCYSTHRLEUASNPHEPROILESERPROILEGLUTHRVALPROVALLYSLEULYSPROGLYMETASPGLYPROLYSVALLYSGLNTRP
    2101 TTGACTCAGATTGGTTGCACTTTAAATTTTCCCATTAGCCCTATTGAGACTGTACCAGTAAAATTAAAGCCAGGAATGGATGGCCCAAAAGTAAACAAT

PROLEUTHRGLUGLULYSILEGLYVALGLUILECYSTHRGLUMETGLULYSGLUGLYLYSILESERLYSILEGLYPROGLUASNPROTYRASN
    2201 GGCCATTGACAGAAGAAAAATAGGAGTAGAAATTTGTACAGAAATGGAAAAGGAAGGAAATTTCAAAAATTGGGCCTGAAAATCCATACAA

THRPROVALPHEALAILELYSLYSLYSASPSERTHRLYSTRPARGLYSLEUVALASPPHEARGGLULEUASNLYSARGTHRGLNASPPHETRPGLUVAL
    2301 TACTCCAGTATTTGCCATAAAGAAAAAAGACAGTACTAAATGGAAGAAAATTAGTAGATTTCAGAGAACTTAATAAGAACTCAAGACTTCTGGGAAGTT

GLNLEUGLYILEPROHISPROALAGLYLEULYSLYSLYSSERVALTHRVALLEUASPVALGLYASPALATYRPHESERVALPROLEUASPGLUASPPHE
    2401 CAATTAGGAATACCACATCCCGCAGGTTAAAGAAAAAAATCAGTAACAGTGGATGCATATTTTTCAGTTCCCTTAGATGAAGACT

ARGLYSTYRTHRALAPHETHRILEPROSERILEASNASNGLUTHRPROGLYILEARGTYRGLNTYRASNVALLEUPROGLYLYSGLYSERPRO
    2501 TCAGGAAGTATACTGCATTTACCATAAACAATGAGAGACACCAGGGATTAGATATCAGTACAATGTGCTTCCACAGGGATGGAAAGGATCACC

ALAILEPHEGLNSERSERMETTHRLYSILELEUGLUPROPHEARGLYSGLNASNPROASPILEVALILETYRGLNTYRMETASPASPLEUTYRVALGLY
    2601 AGCAATATTTCCAAAGTAGCATGACAAAATCTTAGAGCCTTTTAGAAAACAAATCCAGACATAGTTATCTATCAATACATGGATGATTTGTATGTAGGA

SERASPLEUGLUILEGLYGLNHISARGTHRLYSILEGLULEUHISPROASPLYSTRPTHRPROGLULYSASPSERTRPTHRVALASNASPILE
    2701 TCTGACTTAGAAATAGGGCAGCATAGAACAAAAATAGAGGAGCTGAGACAACATCTGTTGAGGTGGGACTTACCACACCAGACAAAAACATCAGAAAG

PROPROPHELEUTRPMETGLYTYRGLULEUHISPROASPLYSVALARGGLNLEUCYSLYSLEULEUARGGLYTHRLYSALALEUTHR
    2801 AACCTCCATTCCTTTGGATGGGTTATGGAACTTCCATCCTGATAAATGGACAGTACACCTATAGTGCCTAGAAAGAACAGCTGGACTGTCAATGACAT

GLNLYSLEUVALGLYLYSLEUASNTRPALASERGLNILETYRPROGLYILELYSVALARGGLNLEUCYSLYSLEULEUARGGLYTHRLYSALALEUTHR
    2901 ACAGAAGTTAGTGGGGAAATTGAATTGGGCAAGTCAAATTTACCCAGGGATTAAAGTAAGGCAATTATGTAAACTCCTTAGAGGAACCAAAGCACTAACA
                                                          G
```

FIG. 2D

```
       GluValIleProLeuThrGlyLeuLysLeuLeuGluLeuValLysAsnArgGlyIleLeuLysAspProValHisGlyValTyrTyrAspProSerLysAsp
3001   GAAGTAATACCACTAACAGAGAAGAAAGCAGAGCTAGAACTGGTCAAAAACAGAGAGATTCTAAAAGAACCAGTACATGGAGTGTATTATGACCCTCAAAAG

LeuIleAlaGlyLeuIleGlnLeuTyrGlyIleAsnGlyTyrValThrArgGlyIleLysThrLysProLeuLysThrGlyLeuLeuLeuLysThrArgGlyLeuLysPheLysTyrArgLeuAlaArgMet
3101   ACTTAATAGCAGAGATACAGAGAAGCAGGGCAATGGAAACAGGGGCAAGGCCAATGGACATATCAAATTATCAAGAGCCATTTAAAAATCTGAAAACAGGAAAATATGCAAGAAT

ArgGlyAlaAlaHisThrArgAlaAsnAspValLeuLysGlyLeuAsnGluThrArgGlyLeuAlaValAlaValGlyLeuAsnLysSerIleLeuValIleLeuThrArgThrProGlyLysPheLys
3201   AGGGGTGCCCACACTAGAAATGATGTAAAACAATTAACACAGAGGCAGTGCAAAAATAACCACAGAAAGCATAGTAATATGGGGAAAGACTCCTAAATTTAAA

LeuProIleGlyLeuAsnLysSerGluThrArgProGluThrTrpTrpThrGluAsnAlaAlaThrArgProIleGluPheValAlaAsnThrProProLeuValLys
3301   CTGCCCATAGGACTGAATAAATCAGAAACACATGGGAACATGGGAAGAACAGGAATTCCTGGGATTCTGAGTGGGAGTTTGTCAATACCCCTCCTTTAGTGA
                                                                                                           T
                                                                                                           Lys
       LeuTrpTyrGlnLeuGluLysGluProIleValGlyAlaGluThrPheTyrValAspGlyAlaAlaAsnArgGluThrLysArgGlyLysAlaGlyLeuTyr
3401   AACTATGGTACCAGTTAGAAGAAGAACCAATAGTAGGAGCAGAGACTTTCTATGTAGATGGGGCAGCTAACAGGGAGACTAAGAGAGGAAAGGCAGGATA
             T                                                                                             A

ValThrAsnLysGlyArgGlnLysValValProLeuThrAspThrThrAsnGlnLysThrGluLeuGlnAlaIleTyrLeuAlaLeuGlnAspSerGlyLeu
3501   TGTTACTAACAAAGGAAGACAAAAGGTTGTCCCCCTAACTGACACAACAAATCAGAAGACTGAGTTACAAGCAATTTATCTAGCTTTGCAGGATTCGGGA
                                                                                                       A

LeuGluValAlaAsnIleValThrAspSerGlnTyrAlaLeuGlyIleIleGlnAlaGlnProAspLysSerGluSerGluLeuValAsnGlnIleIleGluGlnLeu
3601   TTAGAAGTAAACATAGTAACAGACTCACAATATGCATTAGGAATCATTCAAGCACAACCAGATAAGAGTGAATCAGAGTTAGTCAATCAAATAATAGAGC
                                                                                                         A

LeuIleLysLysGluLysValTyrLeuAlaTrpValProAlaHisLysGlyIleGlyGlyAsnGluLysValAspLysLeuValSerAlaGlyLeuIleArg
3701   AGTTAATAAAAAAGGAAAAGGTCTATCTGGCATGGGTACCAGCACACAAAGGAATTGGAGGAAATGAACAAGTAGATAAATTAGTCAGTGCTGGAATCAG

LysIleLeuPheLeuAspGlyIleAspLysAlaGlnAspGluHisGluLysTyrHisSerAsnTrpArgAlaMetAlaSerAspPheAsnLeuProPro
3801   GAAAATACTATTTTTAGATGGAATAGATAAGGCCCAAGATGAACATGAAAAATATCACAGTAATTGGAGAGCAATGGCTAGTGATTTTAACCTGCCACCT

ValValAlaLysGluIleValAlaLeuAlaSerCysTyrAspAsnLeuLysLysGlyIleGlyLeuSerProGlyIleLeuTrpGlnLeuLeuGlnAspAsp
3901   GTAGTAGCAAAAGAAATAGTAGCCAGCTGTGATAATGTCAAGCTAAAAGGAGAAGCCATGGAGACTAGTAGTCCAGGAATATGGCAACTAG
```

```
                                                                              VAL
     ILEVALSERPROARGCYSGLUTYRGLNALAGLYHISASNLYS VALGLYSERLEULEUGLNTYRLEUALALEUALAALELEUILETHRPROLYSLYSILELYS
                                          sd
5001 ACATAGTTAGCCCTAGGTGTGAATATCAAGCAGGATATCAAGGTAGGATCTCTACAATACTTGGCACTAGCAGCATTAATAACACCAAAAAAGATAAA
                                                                                                 G
     PROPROLEUPROSERVALTHRARGGLUASPARGTRPASNLYSPROGLNLYSTHRLYSGLYHISARGGLYSERHISTHRMETASNGLYHISAM*
5101 GCCACCTTTGCCTAGTGTTACGAGAAACTGACAGAGAGGATAGAGATGGAACAAGCCCCAGAAGACTAAGGGCCACACAGAGGGCCACACAATGAATGGACACTAG
                                 A
5201 AGCTTTTAGAGGAGCTTAAGAATGAAGCTGTTAGACATTTTCCTAGGATTTGGCTCCATGGCTTAGGGCAACATATCTATGAAACTTATGGGATACTTG
                                                                sa
                                                                 A
5301 GGCAGGAGTGGAAGCCATAATAAGAATTCTGCAACAACTGCTGTTTATCCATTTTCAGAATTGGGTGTGACATAGCAGAATAGGCGTTACTGACAGAG
                                                                sa
5401 GAGAGCAAGAAATGGAGCCAGTAGATCCTAGAGACTAGAGAGCCCTGGAAGCATCCAGGAAGTCAGCCTAAAACTGCTTGTACCAATTGCTATTGTAAAAAGTG
                                                                                                 G   A
5501 TTGCTTTCATTGCCAAGTTTGTTTCATAACAAAAGCCTTAGGCATCTCCTATGGGCAGGAAGAAGCGGAGACAGGCAGCGAAGACCTCCTCAAGGCAGTCAG
              sdG                          T                                              G   A     GAA
5601 ACTCATCAAGTTTCTCTATCAAAGCAGTAAGTAGTACATGTAATGCAACCTATACAAATGCAACCAGGTTAATTGATAGACTAATAGAAAGAGCAGAAGACAGTGG
                                              C   (TAA)                                        A
5701 TTGTGTGGTCCATAGTAATCATAGAATATTAAGACAAAGAAAAATAGAAAATAGAGAAAATATTAAGACAAAGAAGAATAGAGACTAATTGATAGACTAATAGAAAGAGCAGAAGACAGTGG
         ┌env                                                                    ASN      ----gp65 env
     METARGVALLYSGLULYSTYRGLNHISLEUTRPARGTRPGLYTHRMETLEULEUGLYMETLEUCYSSERALATHRGLULYS
5801 CAATGAGAGTGAAGGAGAAATATCAGCACTTGTGGAGATGGGGGTGGAGATGGGCACCATGCTCCTTGGGATGTTGATGATCTGTAGTGCTACAGAAAA
                                                                                           A
     LEUTRPVALTHRVALTYRTYRGLYVALPROVALTRPLYSGLUALATHRTHRTHRLEUPHECYSALASERASPALALYSALATYRASPTHRGLUVALHIS
5901 ATTGTGGGTCACAGTCTATTATGGGGTACCTGTGTGGAAGGAAGCAACCACCACTCTATTTTGTGCATCAGATGCTAAAGCATATGATACAGAGGTACAT
```

FIG. 2G

```
          AsnValThrProAlaThrHisAlaCysValProThrAspProAsnProGlyLeuGlyLeuValValLeuValAlaSerAsnPheAlaSerAsnMetThrProLeuTyrSerAsnAspSerMet
6001      AATGTTTGGGCCACACATGCCTGTGTACCCAGACCCCAACCCAAGAGAAGTAGTATTGGTAAATGTGACAGAAAATTTAACATGTGAAAAATGACA

ValGluGlnMetHisGlyAspIleIleSerLeuThrProAlaSerProGlyLeuAsnSerLeuLysThrProLeuCysValLysLeuThrProLeuCysValAlaLeuSerLeuLysCysThrArgAsp
6101      TGGTAGAACAGATGCATGAGGATATAATCAGTTTATGGGATCAAAGCCTAAAGCCTAAAGCCTAAGCCCACTCTGTGTTAGTTAAAGTGCACTGA

LeuLeuLysSerAlaSerProThrArgAsnThrArgAsnSerSerSerGlyLeuTyrArgGlyMetIleLeuMetGlyLeuLeuLysGlyLeuIleLeuLysAsnCysSerPheAsnIleSerThrSerIleLeuArg
6201      TTTGAAGAATGATACTACTAATAATAATACCAATAGTAGTAGCGGGAGAATGATAATGGAGAAGGAGAGATAAAAAACTGCTCTTCAATATCAGCACAAGCATAAGA
                                                                                                                                    A

GlyLeuTyrLysValGlyLeuAsnLysGluThrTyrArgLeuAlaProHeTyrArgLeuLysLeuAspIleIleProIleAspAsnAspThrThrSerTyrTyrThrHisSerCysTyrSerAsnThrSerVal
6301      GGTAAGGTGCAGAAGGTGCAGAAGAAAGAGAATATGCATTTTTATAAACTTGATATAATACCAATAGATAATGATACTACCAGCTATACGTTGACAAGTTGTAACACCTCAG
                                                                                                                                    A

IleThrArgGlnAlaCysProLysValSerPheGluProIleProIleHisTyrCysAlaProAlaGlyLysPheAlaIleLeuLysCysAsnAsnLysThrPhe
6401      TCATTACACAGGCCTGTCCCAAAGGTATCCTTTGAGCCTATTCCCATACATATTGTGCCCCGGCTGGTTTTGCGATTCTAAAATGTAATAATAAGACGTT

AsnGlyThrArgProCysThrAsnValSerThrValGlnCysThrHisGlyIleArgProValValSerThrGlnLeuLeuLeuAsnGlySerLeuAla
6501      CAATGGAACAGGACCATGTACAAATGTCAGCACAGTACAATGTACACACCAGTAGTATCAACTCAACTGCTGTTAAATGGCAGTCTAGCA
                                                                                                  THR
                                                                                                  AC

GluGluGluValValIleArgSerAlaAsnPheThrAspAsnAlaLysThrIleIleValGlnLeuAsnGlnSerValGlyLeuAsnCysThrArgProAsn
6601      GAAGAAGAGGTAGTAATTAGATCTGCCAATTTCACAGACAATGCTAAAACCATAATAGTACAGCTGAACATCTGTAGAAATTAATTGTACAAGACCCA
                                             VAL                                                G
                                             T

AsnAsnThrArgLysSerIleArgIleGlnArgGlyProGlyArgAlaPheValThrIleGlyLysIleGlyAsnMetArgGlnAlaHisCysAsnIle
6701      ACAACAATACAAGAAAAGTATCCGTATCCAGAGAGGACCAGGGAGAGCATTTGTTACAATAGGAAAAATAGGAAATATGAGACAAGCACATTGTAACAT
          LYS                                                                                   ALA
          AA                                                                                    C

SerArgAlaAlaLysTrpAsnAsnThrLeuLysGlnIleAlaSerLysLeuArgGluGlnPheGlyAsnAsnLysThrIleIlePheLysGlnSerSerGly
6801      TAGTAGAGCAGCAAAATGGAATAACACTTTAAAAACAGATAGCAAATTGGAAGAGCAAGTTTGGGGTAATAATAAAACATTAAGCAATCCTCAGGA
                                                                                                  GC

GlyAspProGlyLeuIleGluValThrArgHisSerPheAsnCysGlyGlyGluPhePheTyrCysAsnSerThrArgLeuPheAsnSerThrTrp
6901      GGGGACCCAGAAATTGTAACGCACAGTTTAATTGTGGAGGGGAATTTTTCTACTGTAATTCAACACACTGTTTAATTAGTACTTGGTTTAATAGTACTTT
```

FIG. 2H

```
          SerThrGluGlySerAsnAsnThrGluGlySerAspThrIleThrLeuProCysArgIleThrLeuProCysArgIleGluLeuLysSerGlnPheIleGluAsnMetTrpProGlyLysAsnGlyLysValAlaGlyLeuValAlaLeuLysAla
7001 GGAGTACTGAAGGGTCAAATAACACTGAAGGAAGTGACACAATAAACACACTCCCATGCAGAGAATAAAACAATTATAAACATGTGGCAGGAAGTAGGAAAAGC-
                                                             ILE                                    A'           SER
          MetTyrAlaAlaProProIleSerGluGlyLeuAsnIleLysArgCysSerSerAsnIleThrGlyLeuLeuLeuThrArgAspGlyGlyAsnAsnAsnAsnGlyGluGlu
7101 AATGTATGCCCCTCCCATCAGCGGACAATTAGATGTTCATCAAATATTACAGGGCTGCTATTAACAGGGACAGATGGTGGTAATAACAATAACAATGAGTCCGAG-
                                                                                                           G
          IleAsnPheArgProGlyGlyGlyAspMetArgAspAsnTrpArgSerGluLeuTyrLysTyrLysValValLysIleGluProLeuGlyValAlaProThrLys
7201 ATCTTCAGACCTGGAGGAGGAGATATGAGGGACAATTGGAGAAGTGAATTATATAAATATAAAGTAGTAAAAATTGAACCATTAGGAGTAGCACCCACCA-
                                          gp41 env
          AlaLysArgArgValValGlnArgGluLysArgAlaValGlyLeuGlyAlaLeuPheLeuGlyPheLeuGlyAlaAlaGlySerThrMetGlyAlaAlaAla
7301 AGGCAAAGAAGAGAAGTGGTGCAGAGAGAAAAAAGAGCAGTGGGAATAGGAGCTTTGTTCCTTGGGTTCTTGGGAGCAGCAGGAAGCACTATGGGCGCAGC-
                                                                                                                  A
          SerMetThrLeuThrValGlnAlaArgGlnLeuLeuSerGlyIleValGlnGlnGlnAsnAsnLeuLeuArgAlaIleGluAlaGlnGlnHisLeuLeuGln
7401 GTCAATGACGCTGACGGTACAGGCCAGACAATTATTGTCTGGTATAGTGCAGCAGCAGAACAATTTGCTGAGGGCTATTGAGGCGCAACAGCATCTGTTG-
                                                                                                  HisThr
          GlnLeuThrValTrpGlyIleLysGlnLeuGlnAlaArgIleLeuAlaValGluArgTyrLeuLysAspGlnGlnLeuLeuGlyIleTrpGlyCysSerGlyLys
7501 CAACTCACAGTCTGGGGCATCAAGCAGCTCCAGGCAAGAATCCTGGCTGTGGAAAGATACCTAAAGGATCAACAGCTCCTGGGGATTTGGGGTTGCTCTG-
                                                                                                                  C    C  C
          LysLeuIleCysThrThrAlaValProTrpAsnAlaSerTrpSerAsnLysSerLeuGluGlnIleTrpAsnAsnMetThrTrpMetGluTrpAspArgAsnIle
7601 GAAAACTCATTTGCACCACTGCTGTGCCTTGGAATGCTAGTTGGAGTAATAAATCTCTGGAACAGATTTGGAATAACATGACCTGGATGGAGTGGGACAG-
                                                                                                    A
          GluIleAsnAsnTyrThrSerLeuIleHisSerLeuIleGluSerGlnAsnGlnGlnGluLysAsnGluLysGluLeuLeuGluLeuAspLysTrp
7701 AGAAATTAACAATTACACAAGCTTAATACACTCCTTAATTGAAAGTCAAAACCAGCAAGAAAAGAATGAACAAGAATTATTGGAATTAGATAAATGG-
```

FIG. 2I

```
                SER              PHE
       ALAASNLEUTRPASNTRPLEUASNILETHRASNTRPLEUTRPTYRILELYSLEUPHEILEMETILEVALGLYGLYLEUVALGLYLYLEUARGILEVALPHEALA
  7801 GCAAATTTGTGGAATTGGTTGAACATAACAAATTGGCTGTGTGGTATATAAAATTATTCATAATGATAGTAGGAGGCTTGGTAGGTTAAGAATAGTTTTTG-
                G                  -T                                                                    -
                    VAL
       VALLEUSERILEVALASNARGVALARGGLNGLYTYRSERPROLEUSERPHEGLNTHRHISLEUPROTHRPROARGGLYPROASPARGPROGLUGLYILE
  7901 CTGTACTTTCTATAGTAAATAGAGTTAGGCAGGGATATTCACCATTATCGTTTCAGAACCCCACCTCCCAACCCCGAGGGGACCCGACAGGCCCGAAGGAAT-
              G   G                                                                                      -
              GLY
       GLUGLUGLUASPGLYGLUARGASPARGASPARGSERILEARGLEUVALASNGLYSERLEUALALEUILETRPASPASPLEUARGSERLEUCYSLEUPHE
  8001 AGAAGAAGAAGATGGAGAGAGAGATAGAGATAGAAGACAGATCCATTAGAACGAGATCCTTAGTGAACGAGATCTGCGGAGCCTGTGCCTCTTC-
            G   G                                                                                         -
       SERTYRHISARGLEUARGASPLEUGLULEUILEVALTHRARGILEVALGLULEUGLYARGARGGLYTRPGLUALALEULYSTYRTRPASNLEULEU
  8101 AGCTACCACCGCTTGAGAGACTTACTCTTGATTGTAACGAGGATTGTGGAACTTCTGGGACGCGCAGGGGGTGGGAAGCCCTCAAATATTGGTGGAATCTCC-
       GLNTYRTRPSERGLNGLULEULYSASNSERALAVALSERLEULEUASNALATHRALAILEALAVALALAGLUGLYTHRASPARGVALILEGLUVALVAL
  8201 TACAAATATTGGAGTCAGGAGCTAAAGAATAGTGCTGTTAGCTCTTAATGCCACAGCTATAGCAGTAGCTGAGGGGACAGATAGGGTTATAGAAGTAGT-
                                                                                                    E'
                                                                                                    ┌→ METGLYGLYLYSTRPSERLYSSERSER
       GLNGLYALATYRARGALAILEARGHISILEPROARGARGILEARGGLNGLYLEUGLUARGILELEULEUOC*
  8301 ACAAGGAGCTTATAGAGCTATTCGCCACATACCTAGAAGAATAAGACAGGGCTTGGAAAGGATTTTGCTATAAGATGGGTGGCAAGTGGTCAAAAGTAG-
           VAL
       VALILEGLYTRPPROALAVALARGGLUARGMETARGARGALAGLUPROALAALAALASERARGASPLEUGLULYSHISGLYALA
  8401 TGTGATTGGATGGCCTGCTGTAAGGGAAGAATGAGAGACGAGCTGAGCCAGCAGCAGCATCTCGAGACCTAGAAAAACATGGAGCA-
            G
```

FIG. 2J

```
           THR     ASP                                                          GLU
      ILETHRSERSERASNTHRALAALAALAASNASNALAALACYSALAALATRPLEUGLUALAGLNGLUGLUGLUGLULYSVALGLYPHEPROVALTHRPROGLNVALPROLEU
8501  ATCACAAGTAGCAACAGCAGCTAACATGCTTGTCGCCTTGCCTAGAAGACAAGAGGAGAAGGTGGGTTTCCAGTCACACCTCAGGTACCTT
                       C            A                                           G
                                                                               U3
      ARGPROMETTHRTYRLYSALAALAVALASPLEUSERHISPHELEULYSGLULYSGLYGLYLEUGLULYLEUILEHISSERGLNARGARGGLNASPILE
8601  TAAGACCAATGACTTACAAGGCAGCTGTAGATCTTAGCCACACTTTTAAAAGAAAAGGGGGACTGGAAGGGCTAATTCACTCCCAAGGAAGACAAGATAT
                 C                                       (+)          IR

LEUASPLEUTRPILETYRHISTHRGLNLEUTYRPROASPTRPGLNASNTYRTHRTHRPROGLYILEARGTYRPROLEUTHRPHEGLYTYRTRPCYS
8701  CCTTGATCTGTGGATCTACCACACAAGGCTACTTCCCTGATTGGCAGAACTACACAACCAGGGATCAGATATCCACTGACCTTTGGATGGTGC

GLU  LEU
      TYRLYSLEUVALPROVALGLUPROASPLYSVALGLUGLUALAASNTHRSERLEULEUHISPROVALSERLEUHISGLYMETASPASPPRO
8801  TACAAGCTAGTACCAGTTGAGCCAGATAAGGTAGAGGAGGCCAACAAAGGAGAACACCAGCTTGTTACACCCTGTGAGCCTGCATGGAATGGATGACC
                                G      T                 A

GLUARGGLUVALLEUGLUTRPARGPHEASPSERARGLEUALAPHEHISHISVALALAARGGLULEUHISPROGLUTYRPHELYSASNCYSOP*
8901  CGGAGAGAAGAGTGGAGGTTTGGAGTCTCGACTGGCCTTAGCATTTCATCACGTGGCCCGAGAGCTGCATCCGGAGTACTTCAAGAACTGCTGATATCG

9001  AGCTTGCTACAAGGGACTTTCCGCTGGGACTTTCCAGGGAGGCGTGGCCTGGGCCTGGGGAGTGGCCAGCCCTCAGATGCTGCA TATAAG CAGCT
                                                                                          C

U3   R
9101  GCTTTTTGCCTGTACTGGGTCTCTCTCTGGTTAGACCAGATCTGAGCCTGGGAGCTCTCTGGCTAACTAGAGAACCCACTGCTTAAGCCTC AATAAA GCTTG
              R
9201  CCTTGAGTGCTTC
```

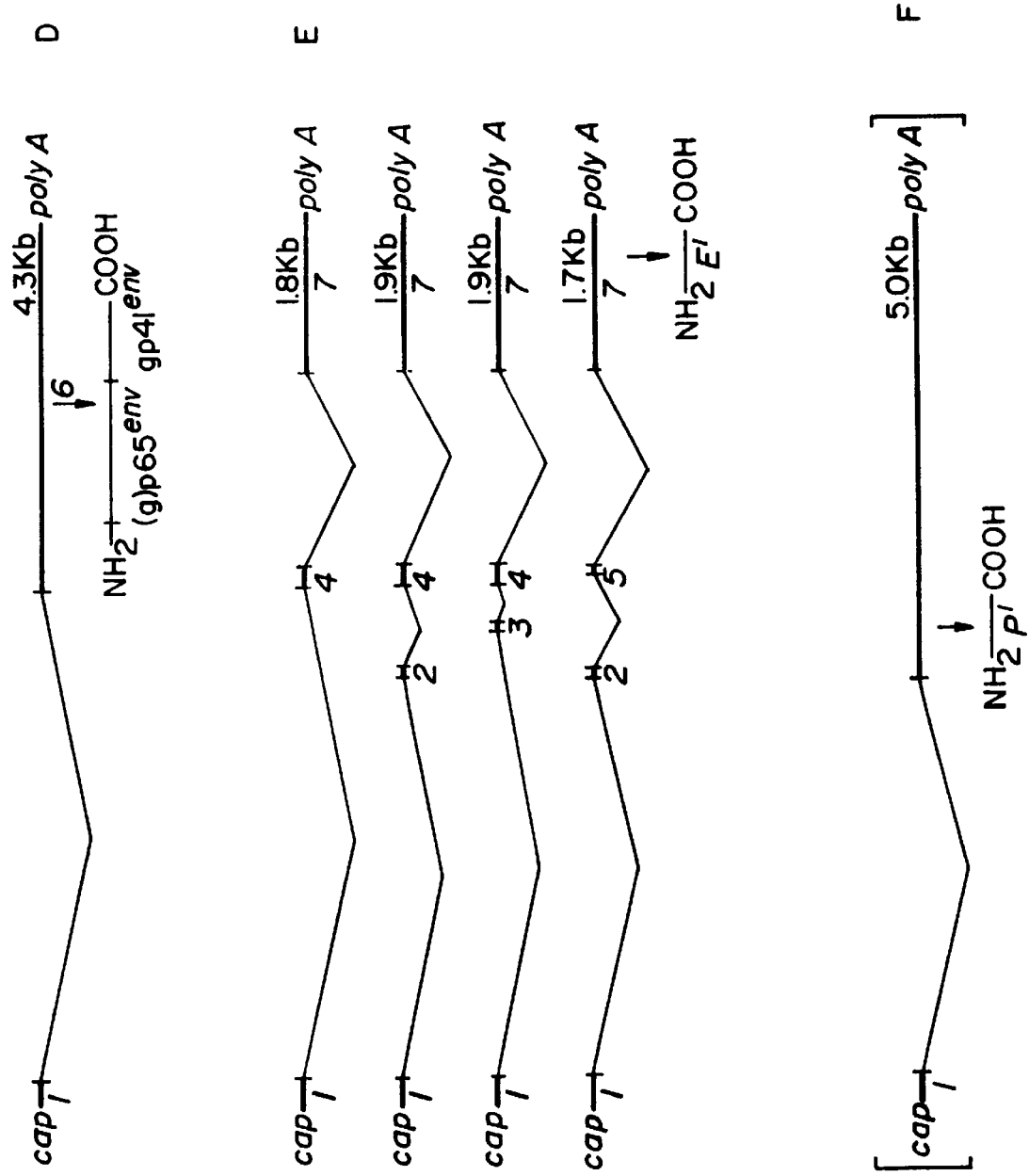

MOLECULARLY CLONED ACQUIRED IMMUNODEFICIENCY SYNDROME POLYPEPTIDES AND METHODS OF USE

This is a continuation of application Ser. No. 08/129,009 filed on 29 Sep. 1993, now abandoned, which is a continuation of Ser. No. 07/979,391 filed Nov. 19, 1992, abandoned, which is a continuation of Ser. No. 07/227,568 filed Aug. 2, 1988, abandoned, which is a division of Ser. No. 06/861,016 filed May 8, 1986, abandoned, which is a continuation-in-part of Ser. No. 06/805,069 filed Dec. 4, 1983, which is a continuation-in-part of Ser. No. 06/685,272 filed Dec. 24, 1984.

FIELD OF THE INVENTION

The present invention relates to immunological products derived from molecular cloning, and to their method of use. More particularly, this invention relates to immunological polypeptides useful as diagnostic products and vaccines in the detection of and vaccination against viral etiological agents of acquired immunodeficiency syndrome. This invention also relates to polypeptides of AIDS retrovirus reverse transcriptase and to their method of use.

BACKGROUND OF THE INVENTION

Analysis of the immune response to a variety of viral infectious agents has been limited by the fact that it has often proved difficult to culture such pathogens in quantities sufficient to permit the isolation of viral polypeptides which may be used (a) as a diagnostic product to detect an immune response to such pathogens or (b) as a vaccine to confer resistance to infection by such pathogens.

The advent of molecular cloning has overcome some of these limitations by providing a means whereby gene products from pathogenic agents can be expressed in virtually unlimited quantities in a non-pathogenic form.

Although antigens from the viruses for influenza (1), foot and mouth disease (2), hepatitis (3), vesicular stomatitis virus (4) and rabies (5) lave been reported to be expressed in *E. coli*, several laboratories have reported that the surface antigen for hepatitis B expressed in prokaryotes is not immunologically reactive with antisera to the naturally occurring antigen (6).

Acquired immunodeficiency syndrome (hereinafter referred to as AIDS) is a devastating disease of the adult immune system which significantly affects cell-mediated immunity. The disease is manifested by a profound lymphopenia which appears to be the result of a loss of T-lymphocytes that have the helper/inducer phenotype T4 as defined by the monoclonal antibody OKT4 (7). Other clinical manifestations include opportunistic infections, predominantly *Pneumocystis carinii* pneumonia, and Karposi's sarcoma (7).

Pre-AIDS, a syndrome that often precedes the onset of AIDS, is characterized by chronic generalized lymphadenopathy. It has been reported that about 10% of patients with pre-AIDS develop AIDS (8).

The predominant risk group for AIDS includes homosexual and bisexual males, intravenous drug abusers, recipients of blood components (primarily hemophiliacs receiving treatment with Factor VIII) and recipients of blood transfusions (7). The epidemiology of this syndrome indicates that AIDS is caused by an infectious agent which is transmitted by intimate contact or contact with blood or blood products (7).

A human retrovirus related to the previously described human T-lymphotropic viruses HTLV-I and HTLV-II, is the causative agent for AIDS (8, 9, 10). Several laboratories originally isolated and propagated retrovirus associated with AIDS patients (11) and propagated in a permissive T-cell line (12). Similarly, Luc Montagnier of the Pasteur Institut in Paris has found a virus in AIDS patients designated LAV (lymphadenopathy associated virus). Some authors have reported that LAV may be similar or identical to HTLV-III (13, 14). A virus isolated from an AIDS patient, designated ARV (AIDS Related Virus), was reported to have been identified and cloned (15). These and other AIDS retroviruses are hereinafter referred to as AIDS associated retrovirus.

HTLV-III is a retrovirus with a genome comprising approximately 10 kb of RNA. The virus particle contains a capsid consisting of a number of proteins. The primary core protein is designated p-24 and has a corresponding molecular weight of about 24,000 daltons. The p-24 core protein is synthesized in vivo as part of a precursor polypeptide encoded by the gag region of the HTLV-III genome. This precursor polypeptide is processed in the infected cell to form p-24 and other viral proteins. In addition, an envelope protein designated gp-41 (MW 41,000 daltons), is also a constituent of the virus particle and is encoded in the env region of the HTLV-III genome.

Antibodies to the envelope protein gp-41 of HTLV-III have been detected in serum from AIDS and pre-AIDS patients. Approximately 88% of AIDS and 79% of pre-AIDS patients have detectable antibodies to HTLV-III envelope protein (16). One author has reported that there is a 90–100% sero-conversion to such antibodies (8). In addition to antibodies to the gp-41 envelope protein, antibodies to the HTLV-III core protein p-24, and the HTLV-III proteins designated p-55, p-60 as well as the glycoproteins gp-65, gp-120 and gp-160 have been detected in patients with AIDS (16, 17). The detection of antibodies to these and other as yet unknown antigens is, therefore, a significant indication of exposure to or productive infection by the agent responsible for AIDS.

In addition, certain of these viral polypeptide sequences may be used as a vaccine to induce the production of neutralizing antibodies conferring resistance to AIDS infection. A need exists for variant sequences such as fusions of the viral polypeptide with highly immunogenic polypeptides, in order to facilitate induction of a high titer immune response, as well as for deletions of undesired viral sequences.

Accordingly, it is an object herein to express, in a prokaryotic host, viral antigens of an AIDS associated retrovirus which are non-pathogenic and which may be used as diagnostic product to detect AIDS.

It is a further object of the present invention to prokaryotically express a diagnostic product to detect AIDS consisting of variant composite polypeptides of naturally occurring AIDS related polypeptide sequences.

Further, an object of the present invention is to express in mammalian cell culture AIDS associated polypeptides or variants, including fusion polypeptides of an AIDS associated polypeptide which may be used as a vaccine against AIDS.

Still further, an object of the present invention is to express AIDS RNA dependent DNA polymerase (reverse transcriptase) for use in an assay to identify transcriptase inhibitors.

SUMMARY OF THE INVENTION

In accordance with this invention, DNA encoding AIDS-associated polypeptides is identified and employed in recombinant prokaryotic or mammalian cell culture systems to synthesize predetermined AIDS-associated polypeptides and derivatives and amino acid sequence variants thereof. Derivatives of AIDS-associated polypeptides include unglycosylated or variantly glycosylated polypeptides, as well as formylmethionyl N-terminal species.

Variants of normal AIDS-associated virus polypeptides are provided wherein one or more amino acid residues of the normal polypeptides have been deleted or substituted by other residues, or one or more amino acid residues inserted. These variants include predetermined fragments of normal polypeptides (deletion variants), fusion polypeptides containing an AIDS-associated virus polypeptide or fragment thereof with a second polypeptide which is not AIDS-associated virus polypeptide or fragment thereof (fusion or insertional variants), and all of the above in which an amino residue has been substituted. Preferred deletion variants are gp41 or gp160 envelope proteins from which one or more hydrophobic regions have been deleted.

DNA encoding the polypeptides of this invention are provided, as well as vectors operably incorporating such DNA and mammalian or prokaryotic cell cultures transformed therewith.

The predetermined polypeptide sequences of an AIDS-associated retrovirus produced herein are essentially free of other naturally occurring AIDS related polypeptides. These polypeptides contain at least one antigenic determinant which is capable of specifically binding complementary antibody. Specific polypeptide sequences described herein are designated p-24, p-15, E', reverse transcriptase and envelope (env) polypeptides. In preferred embodiments, fragments and/or fusions of predetermined polypeptide sequences of an AIDS associated retrovirus, containing at least one antigenic determinant capable of specifically binding complementary antibody, are provided. In one species of this embodiment, a C-terminal portion of the p-24 and the entire p-15 sequence is removed. This truncated p-24, expressed in E. coli, demonstrates an unexpected reactivity with antibody to an AIDS associated retrovirus. Particularly preferred fragments are those of the env protein gp120 which are able to bind normal host cell receptors in competition with the intact virus, as well as E' polypeptide fragments.

The fusion polypeptides comprise (a) a predetermined polypeptide sequence of an AIDS associated retrovirus or fragment thereof having at least one antigenic determinant capable of specifically binding complementary antibody and (b) a second polypeptide sequence which is not immunologically reactive with antibodies normally present in a biologically derived sample which is to be assayed for the presence of antibodies to AIDS associated retrovirus. If the fusion polypeptide is to be used as a component of a vaccine the second polypeptide sequence also should be incapable of inducing antibodies which are cross-reactive with polypeptides which are naturally occurring in the subject such vaccine is directed to. In this case, polypeptides from lower eukaryotes other than from yeast are useful.

In one species of a fusion polypeptide, DNA sequences encoding a polypeptide sequence of human growth hormone (HGH) are positioned five prime to a DNA sequence encoding the p-24 and p-15 polypeptide sequence of HTLV-III. This is expressed and processed in E. coli as an HGH-p24 fusion polypeptide which specifically binds complementary antibody. Similarly, fusions of E' and env polypeptides such as gp41 and gp120 with viral, synthetic or prokaryotic polypeptides are provided. A preferred fusion is the fusion of a mature envelope polypeptide or fragment thereof with a signal sequence heterologous to the HTLV-III retrovirus, typically a eukaryotic or other viral polypeptide signal sequence. These results demonstrate that viral antigens associated with AIDS may be expressed as a fusion polypeptide to detect naturally occurring antibodies produced by AIDS infected individuals.

The immunoprotective polypeptide sequences of this invention are formulated into therapeutically effective dosages with a pharmaceutically acceptable vehicle and administered to AIDS-susceptible animals in order to induce the production of antibodies to such polypeptide sequences.

In a contemplated embodiment, a polypeptide comprising or consisting of a predetermined polypeptide sequence of RNA dependent DNA polymerase (reverse transcriptase) from an AIDS associated retrovirus is cloned and expressed for use in an assay system to identify compounds which inhibit such AIDS associated reverse transcriptase. Such compounds may be administered as a pharmaceutical agent to inhibit infection by AIDS associated retrovirus or dissemination of such retrovirus in infected individuals.

BRIEF DESCRIPTION OF THE DRAWINGS

FIG. 1 shows the amino terminal polypeptide sequence of p24 core protein obtained from live HTLV-III retrovirus and the corresponding DNA sequence deduced therefrom.

Figure 2E:
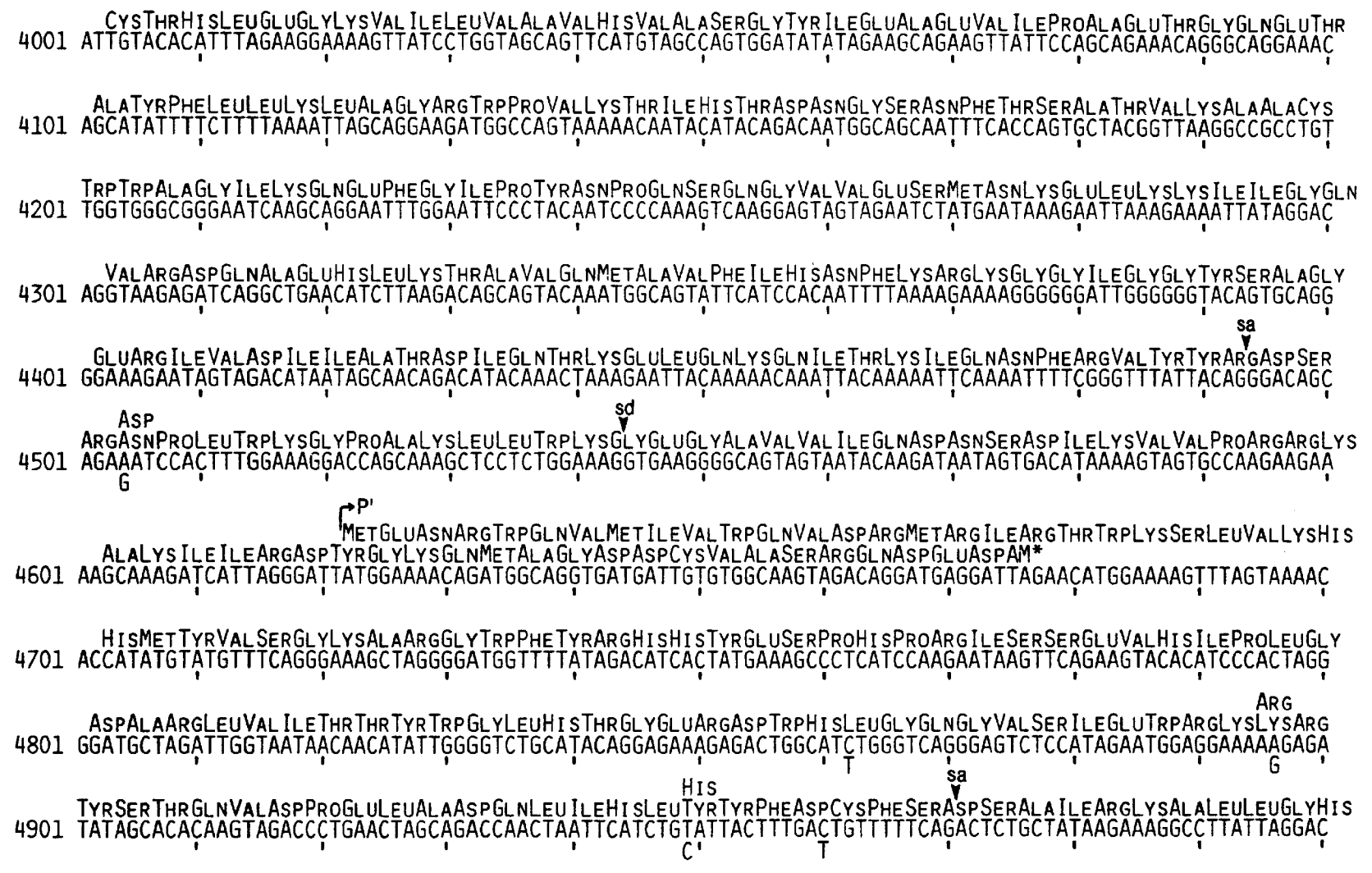

FIGS. 2A–2D show the DNA sequence, the putative polypeptide sequence and a partial restriction map of the HTLV-III genome. The terminal repeat ("R") and unique regions (U5 for 5' and U3 for 3') are shown. The putative positions assigned to the gag region, reverse transcriptase ("pol"), envelope ("env") and E' and P' proteins are shown. The designations sd and sa are splice donor and splice acceptor sites, respectively. Overlapping amino acid sequences represent putative mRNA splicing phenomena. Alternative bases indicate differences found among clones, indicative of variation found among strains in the viral population.

FIGS. 2L-1 and 2L-2 shows the putative mRnA splicing activity of the virus, the resulting messengers and the proteins thereby encoded.

DETAILED DESCRIPTION

Figure 2K:
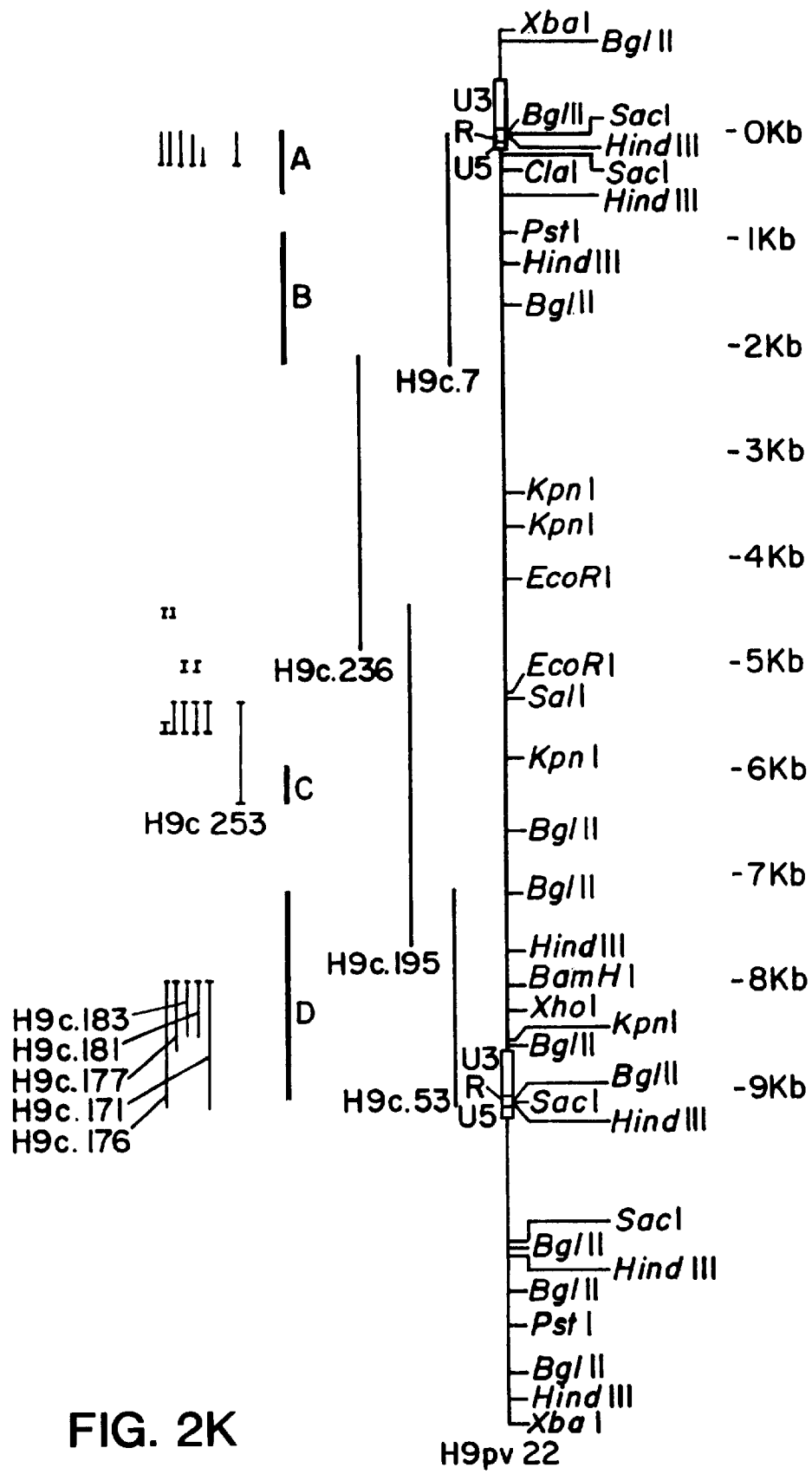
FIG. 2K depicts a restriction enzyme map of the provirus DNA and overlapping cDNA clones.

Applicants have demonstrated that viral protein from an AIDS associated retrovirus can be expressed directly or as a variant polypeptide in host cells and that such recombinant polypeptides are capable of specifically binding antibody to an AIDS associated retrovirus. Such variant polypeptides include viral polypeptides fused with one or more second polypeptide sequences as well as deletions, insertions, substitutions and derivatives of the viral polypeptide. In addition, directly expressed and certain variant polypeptides, each of which contain fragments of a predetermined polypeptide sequence of an AIDS associated retrovirus, also react with antibody to AIDS associated retrovirus. These results indicate that such recombinant polypeptides may be used as diagnostic agents to detect AIDS in individuals, donated blood and blood products.

Further, such polypeptides may be used as immunogens to induce the production of neutralizing antibodies which confer resistance to infection by an AIDS associated retrovirus.

Still further, the reverse transcriptase of an AIDS associated retrovirus may be used to identify compounds which may inhibit infection by AIDS associated retrovirus or the dissemination of such retrovirus in infected individuals.

The fusion polypeptides of the present invention comprise an AIDS associated polypeptide sequence and a second polypeptide sequence. These second polypeptide sequences may be used to: 1) promote secretion of the fusion polypeptide from a bacterial host into the extra-cellular environment or the periplasm of gram negative bacteria, 2) facilitate the functional association of the fusion polypeptide with the surface membrane of recombinant host cells or 3) provide a polypeptide sequence which may be used to purify the fusion polypeptide (e.g. purification of an HGH-AIDS fusion polypeptide by fractionation on an immunoadsorbent specific for HGH). Depending upon the particular applications, second polypeptide sequences used to form a fusion polypeptide with an AIDS associated retrovirus may be of prokaryotic or eukaryotic origin and may be positioned at the amino terminus, carboxy terminus, at both ends of the AIDS associated polypeptide sequence, or inserted within the AIDS associated polypeptide sequence.

Examples of second polypeptide sequences which may be used to promote secretion of the fusion polypeptide include (1) the signal sequence of Herpes Simplex Virus gD protein disclosed in copending U.S. patent application Ser. No. 527,917 filed Aug. 30, 1983; (2) the signal sequence of *E. coli* alkaline phosphatase or *E. coli* enterotoxin STII disclosed in copending U.S. application Ser. No. 658,342, filed Oct. 5, 1984, and references disclosed therein, and (3) pre-HGH disclosed in copending U.S. application Ser. No. 488,232 filed Apr. 25, 1984 or other higher eukaryotic signal sequences such as that of gamma interferon.

An example of a second polypeptide sequence which facilitates functional membrane association is the transmembrane sequence of Herpes Simplex Virus disclosed in U.S. application Ser. No. 527,917 filed Aug. 30, 1983.

Since many individuals at risk for AIDS also have antibodies to *E. coli* and other enterobacteria, the second polypeptide must be chosen to avoid false positive immunological reactivity with these antibodies. Polypeptide sequences from enterobacteria should therefore be used as a second polypeptide only if such sequences are removed during processing or otherwise prevented from reacting with the biologically derived samples to be assayed for the presence of antibody produced in response to infection by an AIDS associated virus, e.g. by recombinant expression such that the bacterial protein epitopes are modified so as to no longer be cross-reactive with the native protein (see the LE fusions described below).

When the fusion polypeptide of the present invention is used as a vaccine against AIDS infection, the second polypeptide sequence must be chosen to avoid the production of antibodies to polypeptides which are naturally occurring in the subject such vaccine is directed to. For example, in a vaccine for humans the second polypeptide sequence is preferably not HGH. Such vaccines, however, may contain prokaryotic polypeptide sequences or preferably eukaryotic polypeptide sequences other than those of yeast and primates.

The present invention specifically discloses the cloning and expression of certain HLV-III-encoded polypeptides. However, the present invention also contemplates the cloning and expression of other HTLV-III polypeptides. HTLV-III polypeptides which possess antigenic determinants to antibodies for AIDS and pre-AIDS patents include gp-160, gp-120, gp-65, gp-41, p-60/p-55. The gp-160 polypeptide appears to be a precursor polypeptide for gp-120 and gp-41. These particular HTLV-III polypeptides are illustrative and are not intended to limit the scope of the invention.

In addition, the present invention contemplates the generation of a library of products, each containing different antigenic determinants that may be used to determine which antigenic determinants are best suited for detection of AIDS or pre-AIDS. Such a library, for example, Bay be used to determine which antigenic determinants are immunologically reactive to serum derived from healthy individuals who are serologically positive for AIDS. Those antigenic determinants which test positive to such serum but negative to serum from AIDS patients may be prime candidates for a vaccine to induce the production of neutralizing antibodies. Further, diagnostic products containing such antigenic determinants may be used to identify individuals with neutralizing antibodies who are unlikely to develop the severe clinical manifestations associated with AIDS.

Although the present invention is based on studies of HTLV-III it is to be understood that HTLV-III may be similar or identical to LAV or ARV. As so related, polypeptide products derived from those retroviruses are within the scope of the present invention. Accordingly, the designation AIDS associated retrovirus refers to HTLV-III, LAV, ARV, and/or other retrovirus that may cause AIDS or ARC (AIDS-associated complex).

As used herein, a polypeptide sequence of an AIDS associated retrovirus is the full length native polypeptide sequence or the predetermined sequence derived from genomic sequencing.

A naturally occurring (native) polypeptide sequence is the polypeptide formed in virus infected cells or found in the culture fluid of such cells.

Variant polypeptide sequences of an AIDS associated retrovirus include: (1) fusions of viral polypeptide or fragments thereof with second polypeptide sequences including N and C terminal fusions and insertions; (2) deletions of the N-terminal, C-terminal, or an internal region of the polypeptide sequence of viral polypeptide to produce a fragment of a polypeptide sequence of an AIDS associated retrovirus; (3) substitutions of one or more amino acids in a polypeptide sequence of an AIDS associated retrovirus and (4) derivatives such as labelled or bound viral polypeptide sequences which may be labelled by well known techniques or bound to a solid phase such as that disclosed in U.S. Pat. No. 3,720,760 incorporated herein by reference.

"Second polypeptides" are sequences which are fused with a polypeptide sequence of an AIDS associated retrovirus or fragment thereof to form the fusion polypeptide sequences of the present invention. These second polypeptides may be full length or partial protein sequences of eukaryotic, non-AIDS viral or prokactic origin and may be used to promote secretion of the fusion polypeptide, facilitate association of the fusion polypeptide with the surface membrane of an expression host or aid in the purification of the fusion polypeptide. When used as a vaccine, the second polypeptide of a fusion polypeptide is a sequence which is not normally capable of inducing antibodies which are cross-reactive with naturally occurring polypeptides, in the subject such vaccine is directed to.

"Complementary antibody" refers to antibody raised against a corresponding naturally occurring viral epitope or epitope encoded by AIDS-associated retrovirus.

A DNA sequence of an AIDS associated retrovirus encodes the polypeptide and variant polypeptide sequences of the present invention described above.

"Biologically derived sample" includes any biological fluid or tissue sample taken from a human or animal subject which may be assayed to detect the presence of complementary antibody produced in response to exposure to or infection by an AIDS associated retrovirus. Such samples typically comprise blood, urine, semen, and saliva but may include any biological material in which such complementary antibody or AIDS associated retrovirus may be found.

Prokaryotes are preferred for cloning and expressing DNA sequences to produce the diagnostic product and vaccine of the present invention. For example, *E. coli* K12 strain 294 (ATCC No. 31446) is particularly useful. Other microbial strains which may be used include *E. coli* strains such as *E. coli* B, and *E. coli* X1776 (ATCC No. 31537), and *E. coli* c600 and c600hf1, *E. coli* W3110 (F$^-$, $\lambda^-$, prototrophic, ATTC No. 27325), bacilli such as *Bacillus subtilus*, and other enterobacteriaceae such as *Salmonella typhimurium* or *Serratia marcesans*, and various pseudomonas species. When expressed in prokaryotes the polypeptides of the present invention typically contain an N-terminal methionine or a formyl methionine, and are not glcosylated. These examples are, of course, intended to be illustrative rather than limiting.

In general, plasmid vectors containing replication and control sequences which are derived from species compatible with the host cell are used in connection with these hosts. The vector ordinarily carries a replication site, as well as sequences which encode proteins that are capable of providing phenotypic selection in transformed cells. For example, *E. coli* is typically transformed using pBR322, a plasmid derived from an *E. coli* species (18). Plasmid pBR322 contains genes for ampicillin and tetracycline resistance and thus provides easy means for identifying and selecting transformed cells. The pBR322 plasmid, or microbial plasmid must also contain, or be modified to contain, promoters which can be used by the microbial organism for an expression of its own proteins. Those promoters most commonly used in recombinant DNA construction include β-lactamase (penicillinase) and lactose promoter systems (19–21) and a tryptophan (trp) promoter system (22, 23). While these are the most commonly used, other microbial promoters have been discovered and utilized, and details concerning the their nucleotide sequences have been published, enabling a skilled worker to ligate them functionally with plasmid vectors (24). In the specific embodiments disclosed, a trp promoter (22, 23) was used to express the diagnostic product and vaccine of the present invention.

In addition to prokaryotes, eukaryotic cells may be used to express the AIDS associated virus polypeptides including particularly the reverse transciptase of an AIDS associated retrovirus. *Saccharomyces cerevisiae*, or common baker's yeast is the most commonly used among eukaryotic microorganisms, although a number of other strains are commonly available. For expression in Saccharomyces, the plasmid YRp7, for example, (25–27) is commonly used. The plasmid already contains the trp1 gene which provides a selection marker for a mutant strain of yeast lacking the ability to grow in tryptophan, for example ATCC No. 44076 or PEP4-1 (28). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (29) or other glycolytic enzymes (30, 31), such as enolase, glyceraldehyde-3-phosphate dehydrogenase, hexokinase, pyruvate, decarboxylase, phosphofructokinase, glucose-6-phosphate, isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA termination. Other promoters, which have the additional advantage of the transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and the enzymes responsible for maltose and galactose utilization. Any plasmid vector containing yeast-compatible promoter, origin of replication and termination sequences is suitable.

Cultures of cells derived from multicellular organisms also are employed for expression of AIDS associated retrovirus proteins. Mammalian or vertebrate cells are of particular interest, such as VERO and HELA cells, Chinese Hamster ovary (CHO) cell lines, and WI38, BHK, COS-7 and MDCK cell lines. Expression vectors for such cells ordinarily include an origin of replication, a promoter for controlling expression of the DNA encoding the AIDS associated retroviral polypeptide, along with a mammalian selection marker, RNA splice site, polyadenylation site and transcriptional terminator sequences as required.

Vectors capable of transforming mammalian host cells to expression of AIDS associated polypeptides are preferably introduced into host cells with a selection marker, e.g. the gene encoding DHFR (dihydrofolate reductase) in known fashion and then amplified by exposing the transformants to increasing concentrations of selection agent, e.g. methotrexate. For example see U.S. Pat. No. 4,399,216.

For use in mamalian cells, the transcriptional and translational control functions are conventionally obtained from viral sources. For example, commonly used promoters are derived from polyoma, Simian Virus 40 (SV40) and most particularly Adenovirus 2. The early and late promoters of SV40 virus are useful as is the major late promoter of adenovirus as described above. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from adenovirus or other viral (e.g. Polyoma, SV40, VSV, BPV, etc.) source, or may be provided by the host cell chromosomal replication mechanism, if the vector is integrated into the host cell chromosome.

For vectors of the invention which comprise DNA sequences encoding both AIDS associated polypeptide and a cotransformation, selection and amplification gene such as the DHFR enzyme, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine.

On the other hand, if DHFR protein with low binding affinity for MTX is used as the controlling sequence, it is not necessary to use DHFR resistant cells. Because the mutant DHFR is resistant to methotrexate, MTX containing media can be used as means of selection provided that host cells are themselves methotrexate sensitive.

Alternatively, a wild type DHFR gene may be employed as an amplification marker in a host cell which is not deficient in DHFR provided that a second drug selectable marker is employed, such as neomycin resistance.

An example, Which is set forth hereinafter, contemplates the use of CHO cells as host cells and an expression vector which encodes the reverse transcriptase of an AIDS associated retrovirus.

As more fully set out below, the diagnostic product of the present invention is utilized in place of its counterpart derived from a live pathogen in analogous immunoassays. In that regard, a commercial diagnostic test kit would include the above diagnostic products with a variety of other imminological products, at least one of which is labeled, for detection of its complementary antibody or the antigen. The system has been described with respect to the molecular cloning and expression of specific proteins of HTLV-III which possess sufficient antigenic determinants to render them capable of specifically binding complementary antibody, namely antibody to HTLV-III. The specific techniques for cloning and expressing exemplary polypeptides are set forth in more detail in the examples that follow.

There are a number of known techniques for the determination of an unknown quantity of antigen or antibody in biological fluids such as serum, urine, or saliva or from skin samples or the like. In principle, the present invention utilizes such known techniques but substitutes certain molecularly cloned diagnostic reagents of a type set forth above in the otherwise known procedure.

Accordingly, the procedures themselves will be described only generally with reference being made to conventional immunology text for the details of the procedures. It would be well known to skilled workers in the field how to utilize the novel diagnostic products of the present invention in conventional immunological techniques.

For simplicity of description, the general term "diagnostic product" will be used in describing the antigen functional product of the present invention. The term "diagnostic product" is defined as a predetermined polypeptide sequence of an AIDS associated retrovirus with one or more antigenic determinants capable of specifically binding complementary antibody induced by a AIDS associated retrovirus. The diagnostic product is formed in a recombinant host cell capable of its production. The polypeptide sequence may be either functionally associated with a surface membrane of the recombinant cell or it may be recovered and used free of the host cell membrane. Further, the antigenic polypeptide sequence may be fused to a second polypeptide sequence.

The diagnostic methods used in assaying AIDS associated retrovirus, its constituent polypeptides and complementary antibodies are conventional. These include the competitive, sandwich and steric inhibition techniques. The first two methods employ a phase separation step as an integral part of the method while steric inhibition assays are conducted in a single reaction mixture. The methodology for assay of retrovirus or its polypeptides on the one hand and for substances that bind retrovirus or viral polypeptides on the other hand are essentially the same, although certain methods will be favored depending upon the size of the substance being assayed. Therefore the substance to be tested is referred to herein as an analyte, irrespective of its status otherwise as an antigen or antibody, and proteins which bind to the analyte are denominated binding partners, whether they be antibodies, cell surface receptors or antigens.

Analytical methods for AIDS associated retrovirus, its polypeptides, complementary antibody or cell surface receptors all use one or more of the following reagents: Labelled analyte analogue, immobilized analyte analogue, labelled binding partner, immobilized binding partner and steric conjugates. The labelled reagents also are known as "tracers".

The label used is any detectable functionality which does not interfere with the binding of analyte and it binding partner. Numerous labels are known for use in immuno assay, examples including enzymes such as horseradish peroxidase, radioisotopes such as $^{14}C$ and $^{131}I$, fluorophores such as rare earth chelates or fluorescein, spin labels and the like. Conventional methods are available to covalently bind these labels to proteins or polypeptides. Such bonding methods are suitable for use with AIDS associated retrovirus, viral polypeptides, complementary antibody and retrovirus receptors, all of which are proteinaceous.

Immobilization of reagents is required for certain assay methods. Immobilization entails separating the binding partner from any analyte which remains free in solution. This conventionally is accomplished by either insolubilizing the binding partner or analyte analogue before the assay procedure, such as by adsorption to a water insoluble matrix or surface (Bennich et al., U.S. Pat. No. 3,720,760) or by covalent coupling (for example using glutaraldehyde cross-linking), or by insolubilizing the partner or analogue afterward, e.g., by immunoprecipitation.

Steric conjugates are used in the steric hinderance method for homogeneous assay. These conjugates are synthesized by covalently linking a low molecular weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate resulting in a change in flourescence when the the hapten is a fluorophore.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner is generally insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of AIDS associated retrovirus, viral polypeptide or complementary antibody present in the test sample. These heterologous assays are called ELISA systems when enzymes are used as the detectable markers.

Another species of competitive assay is a homogenous assay which does not require a phase separation. Here, a conjugate of an enzyme with the analyte is prepared so that when anti-analyte binds to the analyte the presence of the anti-analyte modifies the enzyme activity. In this case, a polypeptide of an AIDS associated retrovirus or its immunologically active fragments are conjugated with a bifunctional organic bridge to an enzyme such as peroxidase. Conjugates are selected for use with complementary antibody so that binding of the complementary antibody inhibits or potentiates enzyme activity. This method per se is widely practiced under the name EMIT.

Sandwich assays particularly are useful for the determination of polypeptides of an AIDS associated retrovirus, complementary antibody or retrovirus cell surface receptors, i.e., large molecules. In sequential sandwich assays an immobilized binding partner is used to adsorb test sample analyte, the test sample is removed by washing, the bound analyte is used to adsorb labelled binding partner and bound material then separated from residual tracer. The amount of bound tracer is directly proportional to test sample analyte. In a "simultaneous" sandwich assay, test sample is not separated before adding the labelled binding partner.

The foregoing are merely exemplary assays for AIDS associated retrovirus, polypeptides of an AIDS associated retrovirus, complementary antibody and retrovirus cell surface receptors. Other methods now or hereafter developed for the determination of these analytes are included within the scope hereof.

In order to simplify the examples certain frequently occurring and well-known methods employed in recombinant constructions will be referenced by shorthand phrases or designations.

Plasmids are generally designated by a lower case p preceded and/or followed by capital letters and/or numbers. The starting plasmids or sources of DNA herein are commercially available, are publicly available on a restricted basis, or can be constructed from available plasmids or polynucleotides in accord with published procedures. In addition, other equivalent plasmids are known in the art and will be apparent to the ordinary artisan since the plasmids generally only function as replication vehicles for the pre-protein and its control sequences, or for elements thereof in intermediate constructions. "Digestion" of DNA refers to catalytic cleavage of the DNA with an enzyme that acts only at certain locations in the DNA. Such enzymes are called restriction enzymes, and the sites for which each is specific is called a restriction site.

The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1ug or plasmid or DNA fragment is used with about 1 unit of enzyme in about 20 $\mu$l of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleaic acid is recovered with aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop upon ligation (described below) that would impede insertion of another DNA fragment at the restriction site. Unless otherwise stated, digestion of plasmids is not followed by 5' terminal dephosphorylation. Procedures and reagents for dephosphorylation are conventional (32).

"Recovery" or "isolation" of a given fragment of DNA from a restriction digest means separation of the digest by polyacrylamide gel electrophoresis, identification of the fragment of interest by comparison of its mobility versus that of marker DNA fragments of known molecular weight, removal of the gel section containing the desired fragment, and separation of the DNA from the gel, generally by electroelution. This procedure is known generally.

A "Western Blot" is a method by which the presence of polypeptide is confirmed by reaction with labelled complementary antibody. The polypeptide is separated eletrophoretically on a polyacrylamide gel and electrophoretically transferred to nitrocellulose. The nitrocellulose is incubated with labelled complementary antibody, unbound antibody removed and the location of residual label is identified.

"Transformation" means introducing DNA into an organism so that the DNA is replicable, either as an extrachromosomal element or chromosomal integrant. Unless otherwise provided, the method used herein is the $CaCl_2$ transformation method (33).

"Ligation" refers to the process of forming phosphodiester bonds between two double stranded nucleic fragments (34). Unless otherwise provided, ligation may be accomplished using known buffers and conditions with 10 units of T4 DNA ligase ("ligase") per 0.5 $\mu$g of approximately equimolar amounts of the DNA fragments to be ligated.

"Fill in" or "blunting" refers to the repair of sticky ended (overhanging) restriction enzyme fragments in order to create a blunt end that will ligate to other blunt terminal DNA. Generally 2–15 $\mu$g of DNA are incubated in 50 mM NaCl, 10 mM Tris (pH 7.5), 10 mM $MgCl_2$, 1 mM dithiothreitol with 250 $\mu$M of each of four deoxynucleoside triphosphates and 8 units DNA polymerase Klenow fragment at 20° C. for 30 minutes. The reaction is terminated by phenol and chloroform extraction and ethanol precipitation.

"Preparation" of DNA from transformants means isolating plasmid DNA from microbial culture. Unless otherwise provided, the alkaline/SDS method was used (34).

"Oligonucleotides" are short length single or double stranded polydeoxynucleotides which are made by chemically known methods and then purified on polyacrylamide gels (35).

The following specific examples are intended to illustrate more fully the nature of the present invention without acting as a limitation upon its scope.

EXAMPLE 1

This example discloses plasmid construction and expression of the p-24 core polypeptide of HTLV-III in a prokaryotic expression host.

A. Virus Growth and Viral RNA Isolation

HTLV-III$_B$/H9 cells (ATCC CRL 8543) were obtained from Dr. Larry Arthur, Frederick Cancer Research Facility, Frederick, Md. Cultures were maintained in suspension and adapted to RPMI 1640 supplemented with 5% FBS, 2 mM L-glutamine, and 100 μg/ml penicillin-strepomycin mixture. Cells were seeded at a density of $3\times10^5$ viable cells/ml in 10-liter volumes, and cultures harvested at a density of $10–15\times10^5$ viable cells/ml approximately 96 hours after seeding.

Following clarification to remove cells, culture fluids were concentrated by ultrafiltration. HTLV-III virus particles were purified by banding of ultra-filtrate concentrate in a 20% to 60% sucrose gradient in a Beckman SW27 rotor for 16hr at 27,000 rpm using a Beckman LB-M ultracentrige. Sucrose fractions between 30% and 40% were pooled, diluted with TNE (10 mM tris pH 7.5, 0.1M NaCl, 1 mM EDTA) and pelleted by differential ultracentrifugation in a Beckman Type 50 rotor. Virus particles were resuspended in TNE at a concentration approximately 2000 times greater than that of the original medium. These concentrates contained 2.5 to 3.0 mg of protein per ml.

Total RNA was extracted from HTLV-$III_3$/H9 cells (berger, et al., "Biochemistry" 18:5143 (1979)). PolyA containing RNA was purified by fractionation on oligo dT cellulose (Aviv, et al., "P.N.A.S. U.S.A." 74:5463 (1977)) and used for cDNA synthesis.

B. Cloning of the p-24 gene

DNA Synthesis

PolyA RNA was primed with oligo dT for reverse transcriptase mediated cDNA synthesis (Capon, et al., "Nature" 304:507 (1983)). Second strand DNA synthesis by DNA polyerase I was self-primed. The resulting doubled stranded DNA was treated with S1 nuclease to nick the resultant loop and to remove single stranded nucleotides. This blunt ended double stranded DNA was used to construct an HTLV-III phage library.

Phage Library Construction and Detection of HTLV-III Clones

The above double stranded DNA was blunt end ligated with T-4 ligase to R-1 linkers (37) which were synthesized by known techniques (35). This R-I/cDNA was ligated into Eco R1 digested λ GT10 to generate an HTLV-III cDNA library as disclosed (37).

Two copies of the phage library were replica plated onto nitrocellulose filters where the DNA was fixed for in situ hybridization (32). One set of filters was hybridized with $^{32}P$ labelled cDNA prepared from the polyA positive RNA obtained from HTLV-III infected T-cells which was used to generate the cDNA library. The other set of filters was hybridized with $^{32}P$ labelled cDNA obtained from the same cell line which was not infected with HTLV-III. Differential phage hybridization, analogous to the method employed for detecting bacterial cDNA clones (38), allowed applicants to identify a number of HTLV-III positive clones.

Subcloning and Sequencing of of HTLV-III Clones

The above-identified HTLV-III clones from the cDNA phage library were digested with Eco RI. The cDNA inserts were isolated and subcloned into the RI site of pBR322 (ATCC 37017) and propagated in *E. coli* 294 (ATCC 31446).

A number of these subcloned R1 inserts were sequenced by the dideoxy method (39), producing the proviral sequence shown in FIGS. 2*a*–2*d*.

Amino Terminal Sequencing

Live HTLV-III virus particles were purified as previously described. The constituent proteins were fractionated on a 12% polyacrylamide gel using Laemmeli buffer (42). Approximately 600 μg of virus protein was loaded per lane under reducing conditions (41). The gel was stained with Coomassie blue and a protein band having a corresponding molecular weight of 24,000 daltons was cut from the gel. The protein was electroeluted from the gel (41) for amino terminal sequence analysis (42). The amino acid sequence for the first 17 amino acids, excluding residue 16, is shown in FIG. 1. The corresponding DNA sequence is shown directly below the amino acid sequence. A comparison of this DNA sequence with that obtained for the HTLV-III genome in FIG. 2 revealed one particular clone, designated p 7.11 in FIG. 3, which contained a DNA sequence encoding this peptide sequence. This approximately 2.2 kilobase covers the precursor gag region and encodes, 5' to 3', p-12, p-15, p-24 a second p-15 protein, and approximately 300 extra base pairs 3' to the gag region. The DNA sequence and corresponding amino acid sequence of this precursor gag region is shown in FIG. 2. A partial restriction map of the 220 amino acid p-24 core protein region including an R-1 site 3' from the expected carboxy terminal amino acid is depicted for p-7.11 in FIG. 3.

Subcloning of p 7.11

Plasmid 7.11 was digested with Eco R1. The 2.2 kilobase insert was isolated and double digested with RsaI and PstI. The RsaI-PstI and PstI-EcoR1 sequences were isolated. Plasmid UC9 (43) was digested with SmaI and Eco R1. The large fragment comprising most of pUC9 was isolated and hybridized with the Rsa-I PstI and PstI-Eco-R1 fragments. The blunt RsaI and Sma I ends were ligated with T-4 ligase. The resulting plasmid, designated pUCp-24, was used to transform *E. coli* 294.

In constructing pUCp-24 the RsaI site of p-7.11 was used. In so doing, the first ten N-terminal amino acids were excluded from this construction. To incorporate these ten amino acids a synthetic oligonucleotide was constructed (35). The DNA sequence of this 39-mer is

```
  5'                                           3'
p-GATCCCACCTATAGTGCAGAACATCCAGGGGCAAATGGT
       GGTGGATATCACGTCTTGTAGGTCCCCGTTTACCA-p
```

The 5' end of this oligonucleotide contains a synthetic BamHI site for subsequent ligation. Both strands were phosphorylated with polynucleotide kinase Plasmid pUC-24 was digested with BamHI and SphI. The large fragment containing most of the pUC plasmid and the 3' end of the p-24 DNA sequence was isolated. Plasmid 7.11 was digested with Rsal and SphI. The fragment containing p-24 DNA sequence 5' to the Sph I site was isolated. This fragment and the synthetic 39-mer were hybridized to the BamHI-SphI fragment obtained from pUC-24. The blunt ends from the 39-mer and RsaI-SphI fragment were ligated with T-4 ligase. This plasmid, designated pUCp24L, was used to transform *E. coli* 294.

C. Expression Vectors for P-24 Core Protein and Truncated P-24 Core Protein

Figure 4A:
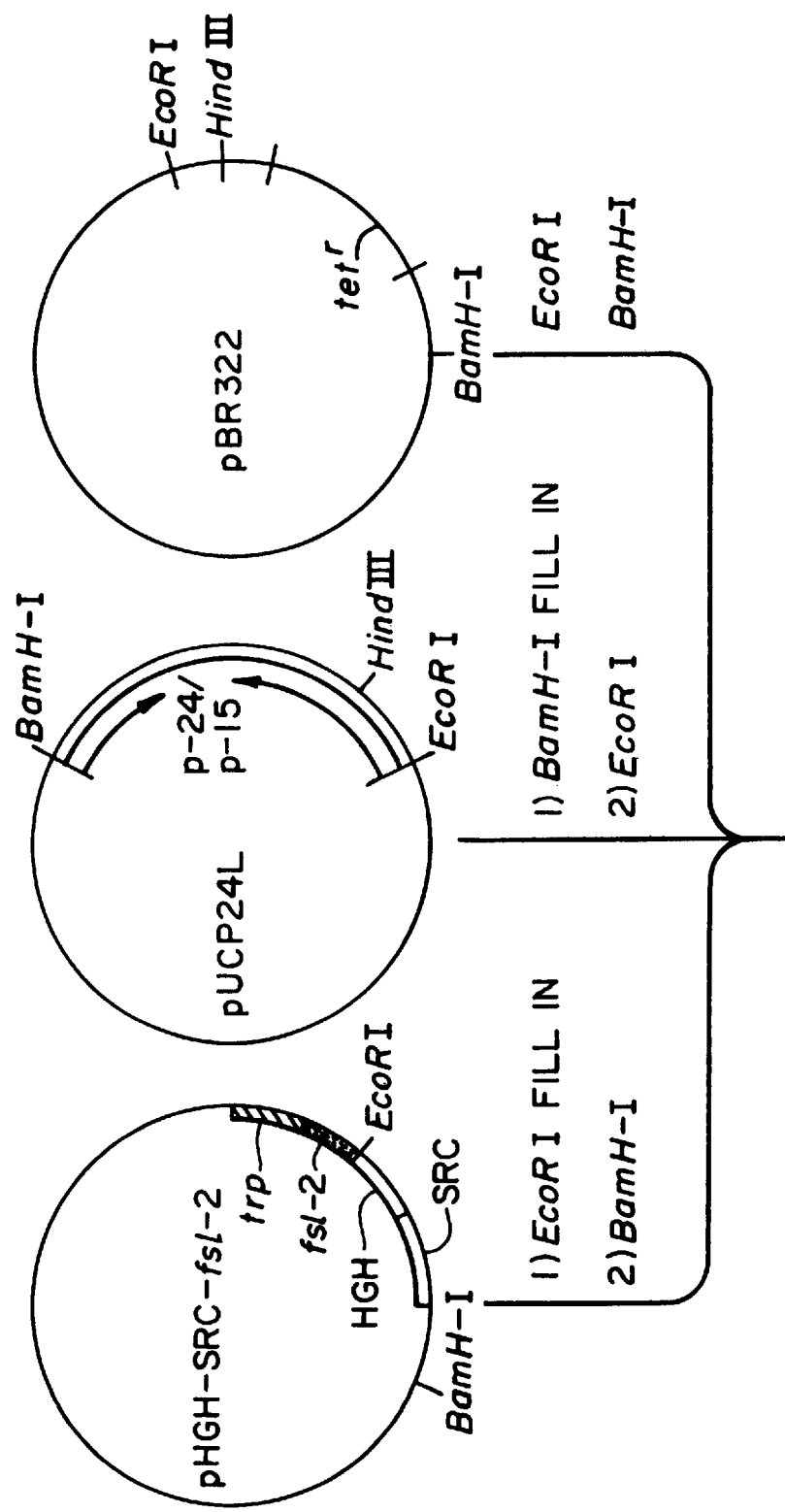
FIGS. 4A–4B depicts the construction of p-24 and truncated p-24 expression vectors.
Figure 4B:
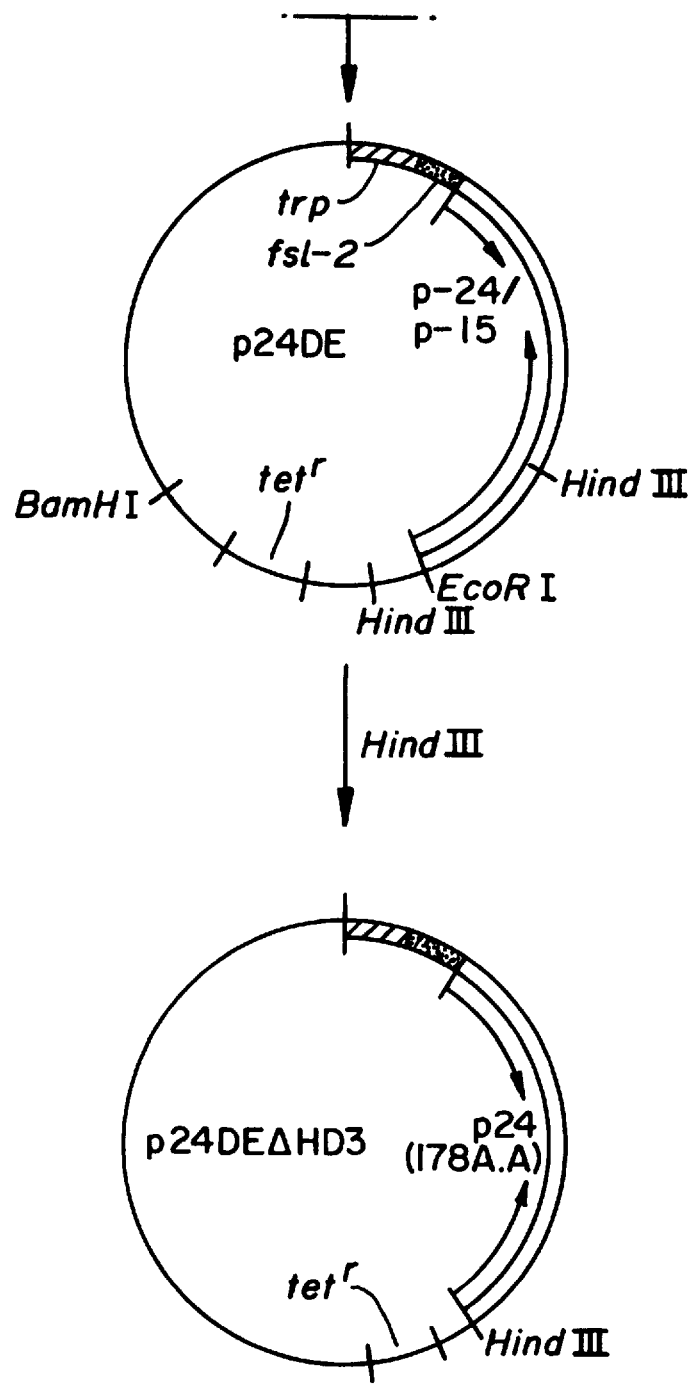

The construction of a p-24 and a truncated p-24 expression vector are depicted in FIG. 4.

Construction of pHGH-SRC-fsl-2

Plasmid pSRCex16 (44) contains pBR322 and a fusion of the first 69 nucleotides of HGH with the DNA encoding the 60,000 MW phosphoprotein of SRC, the fusion being under the control of the E. coli trp promoter. It is not important that the plasmid encode any protein. Instead, any pBR322 plasmid derivative which contains a trp promoter is satisfactory (45).

Plasmid pSRCex 16 is partially digested with EcoRI and filled using the Klenow fragment of DNA polymerase I in order to destroy the EcoRI site in the trp promoter, thereby leaving an EcoRI site at the beginning of the HGH fragment. The resulting plasmid, pEARI5RCex16 was then digested with EcoRI in order to open the plasmid, trimmed with SI nuclease to blunt the ends and ligated to a linker (fsl-2) (46) having the following structure:

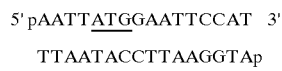

Ligation with the fsl-2 linker recreates the EcoRI site immediately after the ATG, which is underlined above, at the EcoRI cleavage point indicated by an arrow. Accordingly, the first base of the first codon of p24/p-15, as constructed below, is provided by the vector. This plasmid is designated pHGH-SRC-fsl-2.

Construction of a Full Length p-24 Expression Vector

Plasmid pUCp24L was cleaved with BamHI. The cleaved fragment was treated the Klenow fragment of DNA polymerase I in the presence of 0.5 mM nucleotide triphosphates to fill in the BamHI restriction site. This fragment was then digested with EcoRI. The fragment containing the p-24 and p-15 (p-24/p-15) DNA sequence was isolated.

Plasmid HGH-SRC-fsl-2 was cleaved with EcoRI and filled in as previously described. The cleaved plasmid was subsequently digested with BamHI. The fragment containing the trp promoter and ATG initiation codon was isolated. This fragment was hybridized with a fragment confering tetracycline resistance derived from digesting pBR322 by digestion with BamHI and EcoRI and with the blunt ended BamHI-Eco-RI fragment obtained from pUCp24L. The blunt ends were ligated with T-4 ligase. This plasmid, designated p24DE was used to to transform E. coli 294. Transformants were selected by their ability to resist tetracycline. Expression of this plasmid was expected to produce a polypeptide consisting of the full length p-24 core protein and the p-15 protein.

Construction of a p-24 Fragment Expression Vector

Plasmid p-24DE contains a HindIII restriction site located in the vicinity of the DNA sequence encoding amino acids 178–179 of the p-24 core protein. In addition, the p-24DE contains a HindIII site in the tetracycline resistance gene derived from pBR322 located 3' to the p-24 DNA sequence. Digestion of p-24DE with HindIII followed by removal of the fragment encoding amino acids 179–200 and the p-15 protein and the religation of the fragment containing the 5' p-24 DNA sequence under control of the trp promoter produced the plasmid designated p-DE-24ΔHD3. A TAA stop codon within the pBR322 sequence 3' to the truncated p-24 DNA sequence results in the expression of the first 178 amino acids of p-24 core protein and eight amino acid residues encoded by the pBR322 DNA sequence.

EXAMPLE 2

This example discloses the construction and cloning of an expression vector of p-24 core protein sequence of HTLV-III as a fusion polypeptide in a prokaryotic host.

Figure 5A:
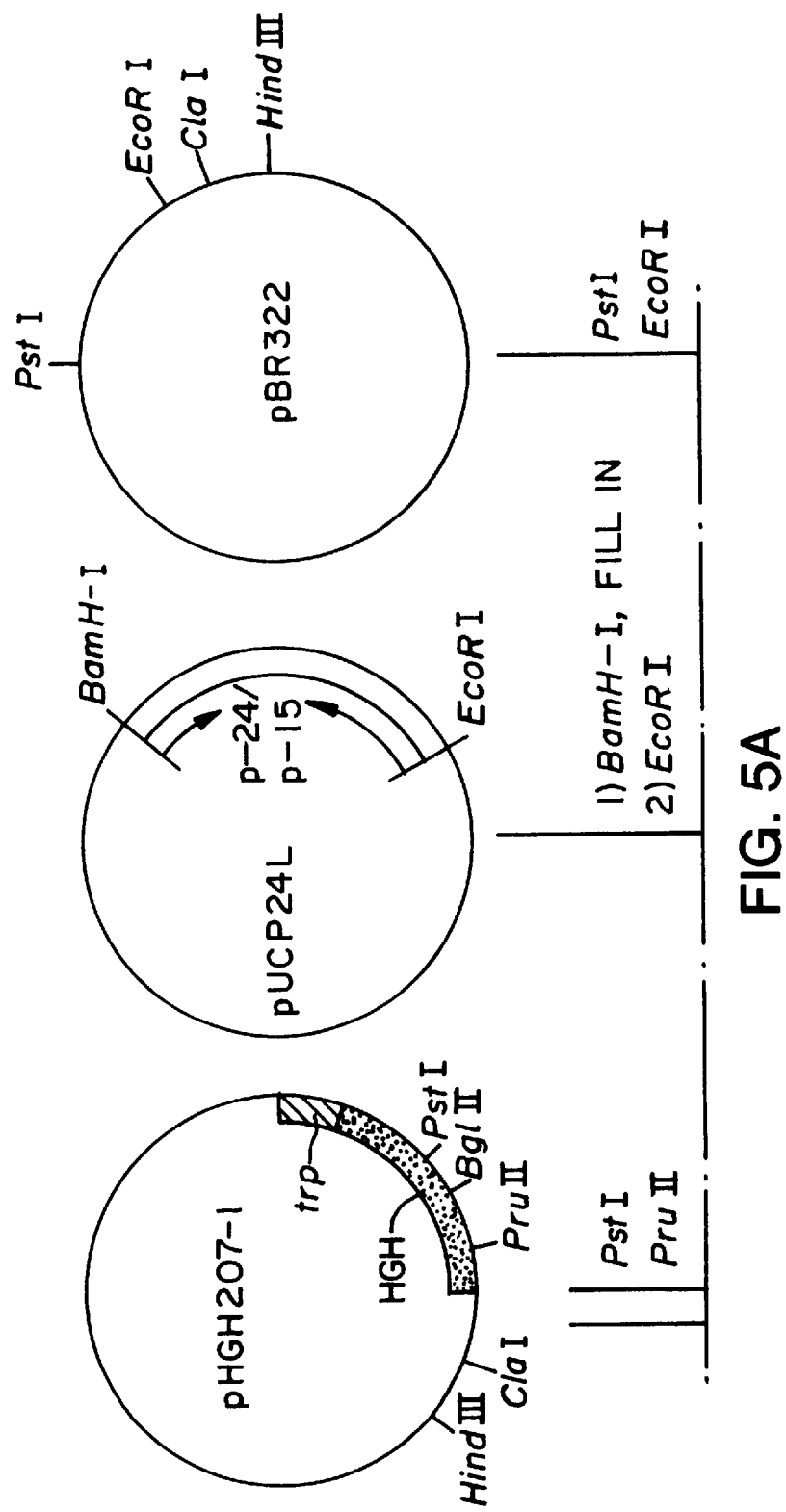
FIGS. 5A–5B depicts the construction of expression vectors for a p-24 composite polypeptide and a truncated p-24 composite polypeptide.
Figure 5B:
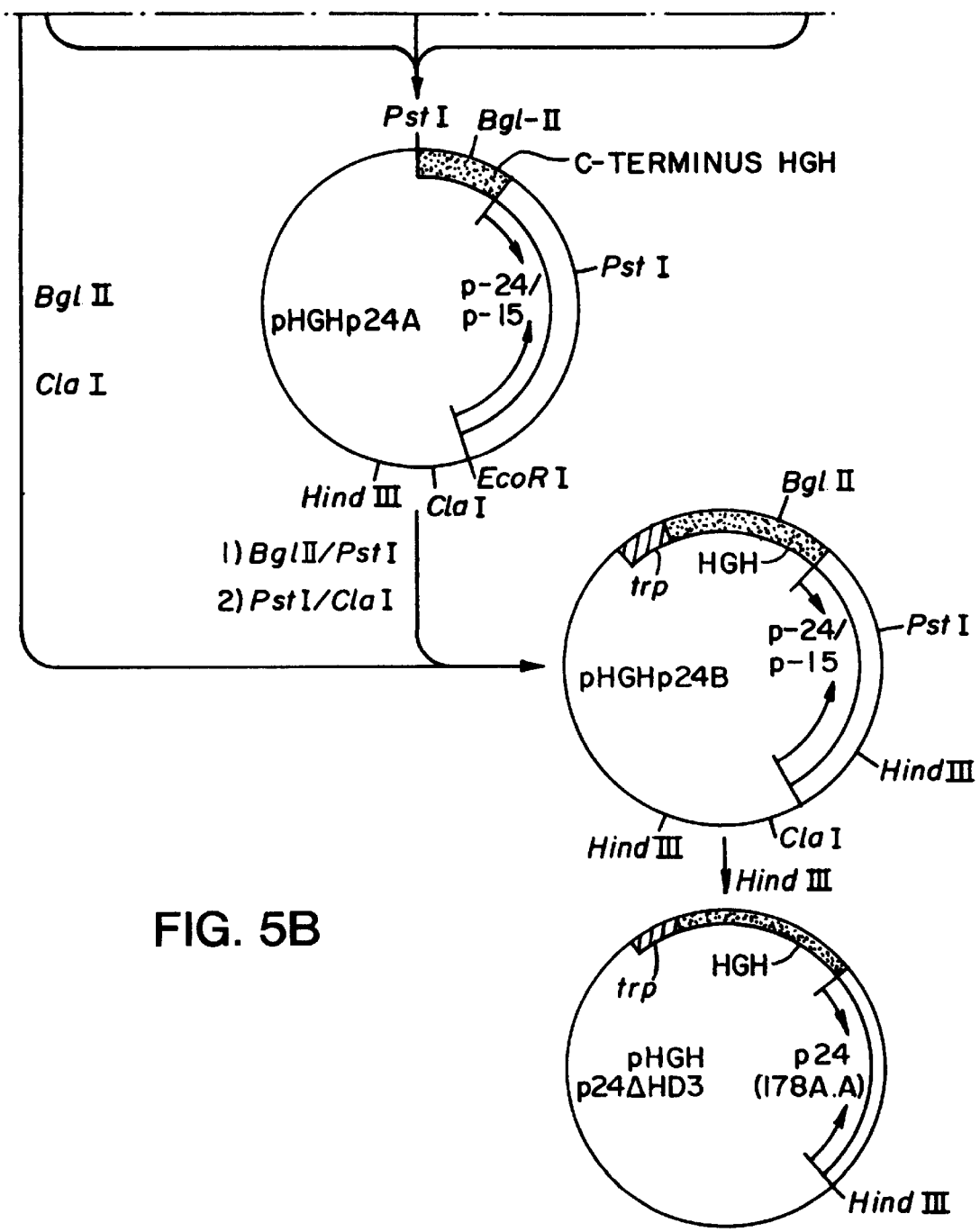

A. Expression Vectors for Fusion Polypeptides of p-24 Core Protein and Truncated p-24 Core Protein The construction of vectors for the expression of composite polypeptides for the p-24 and a fragment of p-24 are depicted in FIG. 5.

Construction of a p-24 fusion polypeptide expression vector

Plasmid pUCp24L was cleaved with BamHI, blunt ended and digested with EcoRI as described above. The fragment containing the p-24/p15 DNA sequences was isolated.

Plasmid HGH 207-1 (45) was digested with Pst1 and Pvu2. The sequence encoding HGH 3' from the Pst1 site to the PvuII site was isolated. This sequence excludes DNA sequences 5' from the Pst1 site as well as the last 8 amino acid residues of mature HGH. These two fragments were hybridized to a PstI-EcoRI fragment derived from pBR322 which contains a gene conferring tetracycline resistance. T-4 ligase was used to ligate the PvuII and blunt ended BamHI site prior to transformation of E. coli 294 with this plasmid, designated pHGH p-24-A.

Plasmid HGHp24-A does not encode the mature HGH amino acid sequence 5' to the Pvu-2 site of pHGH 3'R. A DNA sequence encoding such residues was inserted into the plasmid by the following method.

Plasmid HGH 3'R was digested with BglII and ClaI. The fragment containing the tac promoter and HGH 5' DNA sequences encoding mature HGH to the BglII site was isolated.

Plasmid HGH 207-1 was digested with BglII and PstI. The BglII-PstI fragment containing part of HGH and part of p-24 was isolated. The same plasmid was digested with Pst1 and ClaI followed by isolation of the fragment containing p-15 and part of p-24.

These three isolated fragments were ligated to produce pHGHp24-B. This plasmid contains DNA sequences under control of the tac promoter for expression of mature HGH, except for the C-terminal 8 amino acids of HGH, fused to p-24 core protein and-p-15 protein.

Construction of a Truncated p-24 Fusion Polypeptide Expression Vector

Digestion of pHGHp-24B with HindIII followed by religation results in the same deletion as that obtained for p24DE. The resulting sequence, however, was expected to express a fusion polypeptide of mature HGH (absent 9 C-terminal amino acids) fused to the first 178 amino acids of p-24 and eight amino acid residues from the expression plasmid 3' to the p-24 DNA sequence. This plasmid is designated pHGHp-24ΔHD3.

EXAMPLE 2a

This Example describes the isolation of cDNA encoding the gp41 envelope protein, its tailoring for expression in prokaryotes, expression of a p41 fusion in E. coli and the in vitro resolubilization of the expressed fusion.

Figure 8A:
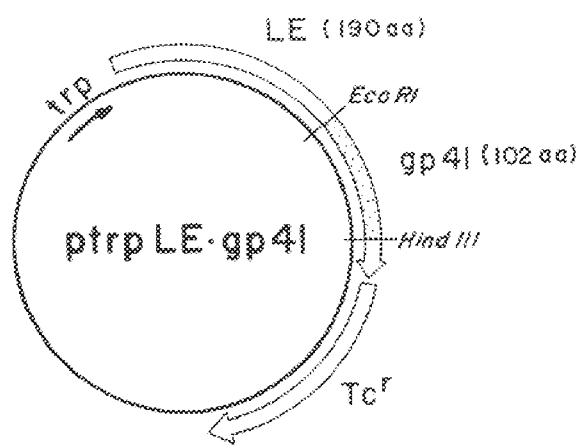
FIGS. 8A, 9A and 10A depict the structure of the plasmids ptrpLE.gp41, ptrpLE.E' and pSVE.E'DHFR. These plasmids are used for the expression, respectively, of fusions of the env and the E' protein of HTLV-III in bacteria and of the unfused E' protein in CHO cell culture.
Figure 8B:
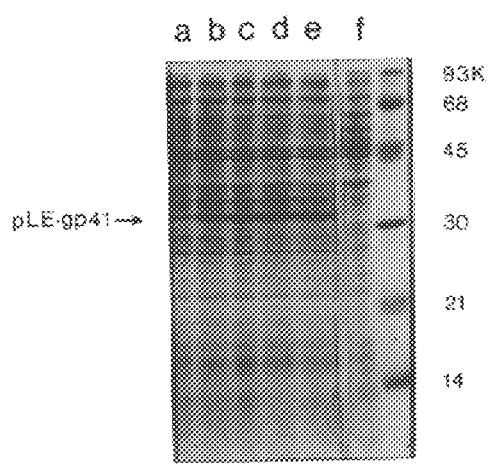
FIGS. 8B, 9B and 10B show polyacrylamide gel electrophoresis patterns demonstrating the synthesis, respectively, of the protein fusions encoded by ptrpLE.gp41, ptrpLE.E' and unfused E' protein encoded by pSVE.E'DHFR.

Viral mRNA was isolated, cDNA prepared from the viral mRNA, and the cDNA cloned into λ GT10 phage as described in Example 1 A and B above. A cDNA clone, H9c.53 was identified that comprised cDNA encoding the complete p41 envelope region (bp 7336 to 8992, FIG. 2d). H9c.53 was digested with RsaI and HindIII and the fragment I corresponding to nucleotides 7417–7722 of the proviral genome was isolated. Fragment I encodes amino acid residues being ValGlnAlaArg and the C-terminal residues being AsnTyrThrSer). Fragment I was ligated to an excess of synthetic EcoRI adaptor (having the sequence AATTCATGTCTTACGGTCAAGG) with a phosphorylated blunt end and a 5' hydroxyl EcoRI end as described above in Example 1B, digested with HindIII in order to cleave ligation-formed dimers, and the resulting 326 bp EcoRI-HindIII fragment isolated on a 6% polyacrylamide gel. Plasmid pNCV(55a) was digested with EcoRI and HindIII and the vector fragment recovered. The 326 bp, gp41-encoding fragment was ligated to the pNCV fragment and the ligation mixture used to transform E. coli (ATCC 31446) to tetracycline resistance. A tetracycline resistant plasmid was recovered (ptrpLEgp41). This plasmid is shown in FIG. 8A. The open reading frame under the control of the trp promoter encodes a gp41 fusion having at its amino terminus 190 residues representing the combined sequence of the amino terminus of the E. coli trp E gene product and its leader together with the amino acid sequence encoded by the EcoRI adaptor, and at its c-terminus 14 residues encoded by residual pBR322 sequence. The fusion contained 306 residues in total.

While the gp41 fusion represents a combined amino and carboxyl fusion of prokaryotic peptides with a gp41 fragment, it will be appreciated that, either or both of the prokaryotic sequences may be deleted or substituted for by other prokaryotic, eukaryotic or synthetic polypeptides. When direct expression of the DNA encoding the gp41 fragment was attempted, rather than as an amino terminal fusion, immunoreactive material could not be identified in the cell culture extracts. The reasons for this are unknown, but may involve instability of the unfused product in E. coli. Accordingly gp41 or its fragments should be expressed in prokaryotes as N-terminal fusions. Such fusions of course will include fusions with the secretory leaders of E. coli periplasmic or extracellular proteins, e.g. the ST-II heat stable enterotoxin or alkaline phosphatase signals, among others. In this case gp41 will be secreted as a mature protein free of prokaryotic sequences. Plasmids encoding fusions of signal peptides with the mature gp41 fragment are readily constructed by inserting synthetic DNA encoding the known sequences of prokaryotic signals in place of the trp LE-adaptor sequence in ptrpLEgp41 using appropriate flanking restriction sites and adaptors or linkers as required. Any remaining extraneous DNA is excised using M13 phage deletional mutagenesis or other conventional method.

The gp42 was truncated to the 102 residue fragment so as to avoid including sequences near the amino and carboxyl terminus that are particularly rich in hydrophobic residues, specifically the two long hydrophobic stretches of 28 and 22 amino acids contained within the putative transmembrane region of gp41. Hydrophobic regions are known in some instances to be deleterious to *E. coli* growth (56, 57). The region extending from residues 29–130 relative to the amino terminus of gp41 did not contain these hydrophobic regions. Note, however, that other host cells such as mammalian cells are suitable for expression of the intact gp41 protein or gp41 fragments containing one or both terminal hydrophobic regions.

*E. coli* (ATCC 31446) was transformed with ptrpLEgp41 and grown in M9 minimal media until values at $A_{550}$ of 6.6, 9, 12, 17 and 21 were reached. Total cellular proteins were electrophoretically separated on 10% SDS polyacrylamide gel and stained with Coomasie blue. The results are shown in FIG. 8*b*, wherein lanes a–e correspond to the above densities in ascending order, while lane f depicts total cellular protein from a pBR322-transformed control (k represents 1,000 daltons). *E. coli* transformants accumulated a prominent protein (LEgp41, at about 10% by weight of the total intracellular bacterial protein) with an apparent molecular weight of 33,000 daltons, consistent with the predicted size of 306 amino acids. Recombinant LEgp41 was purified from refractile bodies enriched for the protein by gel filtration and ion-exchanged chromatography using procedures similar to those previously described for trpLE-foot and mouth disease virus polypeptide fusions (55a). Specifically, cells were washed in 10 mM Tris-HCl, 1 mM EDTA, resuspended in 4 volumes of the same buffer, sonicated, and the refractile bodies collected by centrifugation at 5,000 rpm for 30 minutes in a Corvall GSA rotor. The particles were washed twice and solubilized with 7M guanidine HCl, 0.1% β-mercaptioethanol (BME). The resulting extract was clarified at 19,000 rpm for 4 hours in a Beckman Ti60 rotor. The high speed supernatant was passed through a Sephacryl S-300 (Pharmacia) column. Fractions from the included volume containing LEgp41 were identified by electrophoresis on SDS-polyacrylamide gels, pooled and dialysed extensively against 7.5M urea, 0.1% BME. This pool was chromatographed on DEAE-52 cellulose (Whatman) in 7.5M urea, 0.1% BME, 10 mM Tris-HCl pH 8.5. LEgp41 material that flowed through the column was pooled and dialysed into 4M urea, 10 mM Tris HCl pH 8.5 at a concentration of 0.2 mgs/ml. The purified LEgp41 appeared greater than 95% homogeneous on SDS-polyacrylamide gels by silver staining. LEgp41 was not glycosylated.

This purification procedure eliminated the need to preadsorb patient sera with *E. coli* proteins where the sera is destined for assay of its anti-AIDS antibody level using the LEgp41 fusion; apparently there are little or no pre-existing antibodies to the LE portion in patient sera, at least no antibodies in the conformation in which they exist in LEgp41. This also suggests that immunization programs using fusions of bacterial proteins such as LE with HTLV-III sequences presents a low risk of inducing a hyperimmune response, notwithstanding the fact that humans are commonly exposed to such proteins. Prokaryotic protein fusions for use in vaccines are identified by screening pooled sera from normal individuals for the presence of antibodies that cross-react with the candidate fusion. Conventional methods such as Western Blotting or radioimmunoassay are used for the screening, for example as shown below in Example 2b.

EXAMPLE 2b

Enzyme-linked immunosorbent assay (ELISA) for the detection of antibodies to LEgP41

Purified LEgp41 (Example 2a) was coated in 96-well microtiter plates in 0.05M sodium carbonate pH 9.6 as described (58). Sera were diluted 1:100 fold in TBS and incubated in coated microtiter wells for 1 hour at room temperature. Following 3 washes with TBS the plates were incubated for two hours at room temperature with antibody-enzyme conjugate (mouse monoclonal anti-human IgG F c-horseradish peroxidase, Travenol-Genentech Diagnostics). Plates were again washed with TBS, developed with 3,3',5,5'-tetramethylbenzidine, and color development measured in a plate reader (Dynatech) at 590 nm. Samples with absorbance values greater than twice the mean of negative control sera were scored as positive.

Significant antibody levels to purified LEgp41 were detected in sera from 125 of 127 (98%) clinically diagnosed AIDS patients. By comparison, none of 300 sera from random blood donors previously shown to be seronegative for HTLV-III using a commercial whole virus ELISA test kit were found to react with LEgp41 above the cutoff absorbancy (OD590>0.12). The two AIDS patient sera which did not react with LEgp41 were the only AIDS sera nonreactive by commercial whole virus ELISA. One of these sera was found to react with whole virus on Western Blots but this reactivity could be attributable to p24 core antigen. The other LEgp41 negative AIDS sera did not react with virus on Western Blots, although virus could be cultured from this patient. The reactivity of LEgp41 with the 125 positive AIDS sera was highly sensitive, ranging from 0.21–1.64 OD590 units, with only 3 sera giving OD590 values of <0.4 units. Thus, recombinant LEgp41 shows excellent specificity and sensitivity in detecting antibodies directed against the AIDS retrovirus.

The purified LEgp41 ELISA similarly detected antibodies found in sera from ARC (AIDS-related complex) patients and healthy homosexual men. Sixty of 69 (86%) ARC patient sera reacted with LEgp41, yielding essentially identical results as the commercial whole virus ELISA. Of the 9 nonreactive ARC samples, Western blot analysis with whole virus revealed that two of the sera were positive for p24 only, while the remaining seven sera were completely nonreactive although virus could be recovered from four of these patients.

As expected, a small fraction of sera obtained from asymptomatic homosexual men (26/75, 34%) was reactive in the LEgp41 ELISA. The 26 LEgp41 ELISA-positive sera from this cohort included all 24 positive sera detected by the commerical whole virus ELISA and were confirmed positive by Western Blots utilizing whole virus. Significantly, two of the LEgp41 seropositive samples from healthy gay men were found to be repeatably nonreactive in the commercial whole virus ELISA.

There was no evidence of nonspecific reactivity in the LEgp41 ELISA with sera from six patients with diseases that characteristically give false-positive responses in other serological tests (systematic lupus erythematosis, rheumatoid arthritis, heterophile positive monomucleosis or Goodpasture's syndrome). As an additional test of specificity, sera previously giving false-positive reactions in a commercial whole virus ELISA were examined by the LEgo41 ELISA. A group of 58 sera which had given nonrepeatable positive results with the commerical whole virus ELISA were found not to react in the LEgp41 ELISA. Furthermore, 25 sera which gave repeatable positive results in the commercial ELISA test, but which were negative in more accurate Western Blot assays, also did not react in the LEgp41 ELISA.

EXAMPLE 3

Immunoassay of expressed recombinant polypeptide

A. Expression of full length and truncated p-24 and p-24 fusion polypeptide

E. coli 294 containing each of the Example 2 plasmids is first grow-n in L broth which is rich in tryptophan. This medium represses the trp promoter. Expression of recombinant polypeptide is induced by transferring the culture to M-9 medium, which does not contain tryptophan, after the L-broth culture has obtained an O.D of approximately 0.5 at 550 nm. After about one hour, indole acetic acid is added to the medium to produce a final concentration of about 10 µg/ml to further induce expression. After an additional 5–6 hours at 37° C. the cells are collected by centrifugtation, lysed (47) and subjected to Western blot analysis.

B. Immunological Assay of Expressed Polypeptides

Rabbit Anti-HTLV-III

The polypeptides expressed by the above-identified plasmids were assayed for immunological reactivity with serum from rabbits inoculated with Triton treated HTLV-III retrovirus and which were subsequently boosted with live HTLV-III virus.

Figure 6:
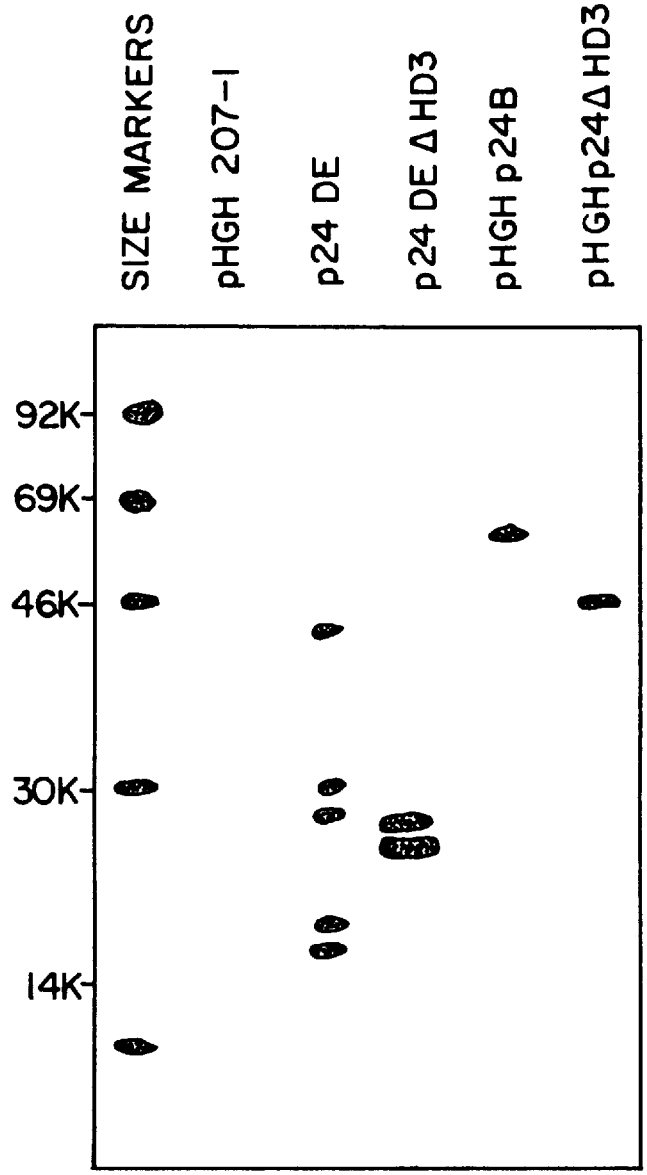
FIG. 6 is a Western Blot of the polypeptide expressed by pDE-24, pDE24ΔHD3, pHGHp-24ΔB and pHGHp-24ΔHD3. The blot was treated with rabbit anti-HTLV-III antibody.

A Western blot of p24DE and p24DEΔHD3 polypeptides and pHGHp24B and pHGHp24ΔHD3 fusion polypeptides expressed in M-9 medium supplemented with indole acetic acid and reacted with HTLV-III rabbit antiserum and $^{125}$I labelled Protein A is shown in FIG. 6. A number of immunologically reactive bands for the p24DE polypeptide are apparent in lane 3. The band corresponding to a molecular weight of about 44,000 daltons corresponds to an expressed protein comprising p-24 and p-15. Surprisingly, two doublets with molecular weights of approximately 24,000 and 15,000 were also observed. The cause of these doublet signals is not presently understood. However, the detection of these doublet signals with molecular weights which are consistent with the gag proteins produced naturally from the polycistronic gag region indicate that this strain of E. coli is capable of processing such precursor polypeptide sequences to produce HTLV-III proteins which may be detected by complementary antibody. A Western blot of p-24DEΔHD3 polypeptide is also shown in lane 4 of FIG. 6. Again, a doublet having a molecular weight of about 20,000 daltons is observed. The absence of a 44,000 dalton p-24/p-15 full length HTLV-III protein and the 15,000 dalton doublet detected for p24DE is consistent with the above interpretation of the p24DE Western blot.

Lanes 5 and 6 of FIG. 6 contain respectively the immunologically reactive proteins expressed by pHGHp24B and pHGHp24ΔHD3. The band in lane 5 having a molecular weight of approximately 65,000 daltons is consistent with the expected composite polypeptide constructed. Further, the band in lane 6 has the expected molecular weight of about 45,000.

Assay with Human AIDS Serum

Figure 7:
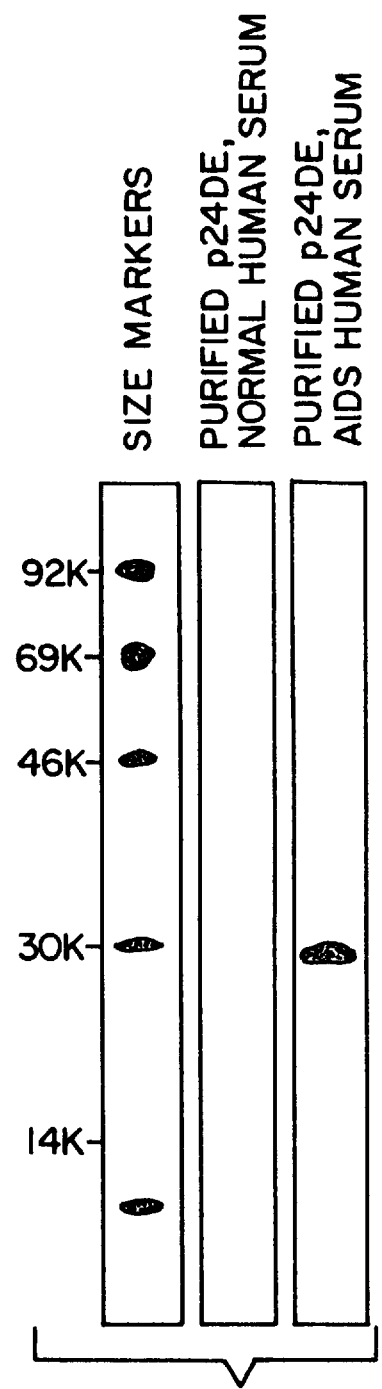
FIG. 7 is a Western blot of the polypeptide expressed by pDE-24. The blot was treated with human serum derived from an individual with AIDS.

The polypeptide expressed by plasmid p24DE was assayed for immunological reactivity with serum from an individual afflicted with AIDS. In FIG. 7, strip 3 depicts the Western blot obtained from p24DE polypeptide treated with human AIDS serum and $^{125}$I labelled Protein A. A diffuse band having a molecular weight of approximately 24,000 daltons can be seen. Strip 2 is a control which contains p-24DE polypeptide treated with normal human serum and $^{125}$I labelled protein A. Strip 1 contains size markers. This assay indicates that polypeptides of the present invention can be used to detect complementary antibody made in response to exposure to or infection by an AIDS associated retrovirus.

Vaccine

The vaccines of the present invention are contemplated and comprise the predetermined polypeptides and fusion polypeptides previously described. The following examples disclose the use of vaccines containing p-24 polypeptide sequences from HTLV-III. However, any polypeptide sequence of an AIDS associated retrovirus, especially those encoded by the env region of the retrovirus genome, may be used.

EXAMPLE 3

Immunization of Mice

The polypeptides encoded by p-24DE and p-24DEΔHD3 are used to immunize BALB/C mice. Each mouse is immunized with 5–25 μg of p-24DE or p-24DEΔHD3 polypeptide contained in 200 μl of an emulsion consisting of 50% aqueous antigen and 50% complete Freund's adjuvant. Each mouse is immunized at multiple intradermal and subcutaneous sites as follows; 25 μl in each rear foot pad, 50 μl in the tail and 100 μl distributed among 3–5 intradermal sites along the back. A control group is similarly injected with emulsion which does not contain antigen. Four weeks after primary immunization the mice are boosted with 5–25 μg of polypeptides as above with the exception that the emulsion was prepared with incomplete Freund's adjuvant. For the booster immunization each mouse receives 200 μl of the antigen emulsion or emulsion lacking antigen distributed as follows: 50 μl in the tail and 50 μl distributed among intradermal sites along the back. Three weeks after boosting approximately 500 μl of blood is collected from each mouse by tail bleeding. The sera obtained from this blood is used for in vitro neutralization studies.

In Vitro Neutralization Studies

Sera from mice immunized with p-24DE or p-24DEΔHD3 polypeptide and from mice in the control group are tested for the ability to neutralize HTLV-III in vitro. 25 μl of serially diluted mouse serum (2-fold dilution: 1:8 to 1:16384) is incubated with 175 μl of HTLV-III concentrate for one hour at 37° in Dulbecco's modified Eagle medium. After incubation, each dilution is applied to approximately 40,000 HUT-78 T-cells (48) contained in each well of a 96 well tissue culture plate. After 3–4 days incubation, virus growth is determined by an immunofluoresence assay for HTLV-III (49) or by a reverse transcriptase assay. The absence of HTLV-III infection of HUT-78 T-cells indicates that the polypeptide induces the production of neutralizing antibodies to HTLV-III in mice.

Primate Assay for Neutralizing Antibodies

The polypeptides which raise neutralizing antibodies in mice are used to immunize chimpanzees which are known to develop generalized lymphadenopathy when infected by HTLV-III retrovirus. Each chimpanzee in an experimental group is immunized with 50–100 μg of polypeptide contained in a 200 μl emulsion consisting of 50% aqueous antigen and 50% complete Freund's adjuvant. Each chimpanzee is immunized as follows at multiple intradermal sites. A control group is injected with emulsion not containing antigen. After four weeks the chimpanzees in each group are boosted with 200 μl of the emulsion or antigen emulsion as above except that the emulsion is prepared with incomplete Freund's adjuvant.

Five weeks after boosting, the chimpanzees in the experimental and control group are challenged with various doses of HTLV-III concentrate. Those polypeptides which prevent the development of lymphadenopathy in the experimental group of chimpanzees are candidates for a vaccine which is capable of inducing the production of neutralizing antibodies in humans which resist infection by AIDS associated retrovirus.

Because complete Preund's adjuvant is not acceptable for use in humans, the above identified polypeptides which prevent lymphadenopathy in chimpanzees challenged by HTLV-III are formulated with an adjuvant suitable for human use. Such formulation may comprise alum precipitated polypeptide complexes (22) which are used to immunize chimpanzees in an experimental group. A control group is vaccinated with adjuvant alone. Formulations which prevent lymphadenopathy in the experimental group comprise a polypeptide in admixture with a pharmaceutically acceptable vehicle which may be used as a human vaccine.

EXAMPLE 5

The composite polypeptides encoded by pHGH p-24-B and pBGHp24ΔHD3 are used in a manner analgous to that disclosed in Example 4 to determine which composite polypeptide confers resistance to AIDS infection in chimpanzees as evidenced by the absence of the development of lymphadenopathy in immunized chimpanzees challenged with HTLV-III retrovirus. The use of HGH polypeptide sequences in such composite polypeptides, however, is not preferred for a human vaccine against infection by AIDS associated retrovirus since such composite polypeptides may induce an autoimmune response against HGH in human subjects. Accordingly, a composite polypeptide vaccine to resist infection by an AIDS associated retrovirus in humans should consist of a predetermined sequence of an AIDS associated retrovirus or fragment thereof expressed as a fusion polypeptide with a secondary polypeptide sequence which is not capable of inducing a substantial autoimmune response to polypeptides naturally occurring in humans.

AIDS Associated RNA Dependent DNA Polymerase

The polypeptide sequence of an AIDS associated RNA dependent DNA polymerase (AIDS reverse transcriptase) is contemplated to be used in an assay to identify compounds which inhibit such transcriptase activity and which may be used as a pharmaceutical agent to inhibit infection by AIDS associated retrovirus or dissemination of such retrovirus in infected individuals. Suramin, a known inhibitor of AIDS reverse transcriptase (53), is disclosed in the following example. However, the assay of other compounds for transcriptase inhibition is contemplated because of the severe clinical side effects that Suramin elicits when administered to humans (53). Examples of such selective inhibitors have been disclosed by several laboratories (54).

EXAMPLE 6

A. Cloning and Expression of AIDS Reverse Transcriptase

The region of the viral genome encoding the AIDS associated retrovirus reverse transcriptase of HTLV-III terminates at nucleotide 4674. Its N-terminus is located within the region extending from nucleotide 1639 to about nucleotide 1800. For the purposes described below it is preferred to select an amino terminus that is located within the gag region (1639–1769), thereby encompassing all optional amino terminii. The region located proximate to nucleotide 1800 includes a number of suitable met codons which are useful to the start codons for constructions expressing the reverse transcriptase. However, it is not critical that in situ met codons be selected. Instead, an exogenous, vector-borne ATG codon is ligated to partial exonuclease digests or M13 deletion mutants of the 5' region of the reverse transcriptase gene. Constructions that are properly in-frame are easily identified by the ability of transformant cell extracts to reverse transcribe RNA. Alternatively, the normal in vivo N-terminus for the reverse transcriptase as processed in a given host is determined by purifying the enzyme from infected cells, sequencing the amino terminus in accord with methods known per se and identifying the cDNA nucleotide sequence encoding the amino acid sequence of the amino terminus. Preferably, the cDNA of the figures is digested with BglII, which cleaves at nucleotide 1642, and SalI (5367). The 3725 bp fragment is recovered. N-terminal cleavage sites other than BglII are at 1738 (DdeI) and 1754 (AluI). However, these enzymes also cleave at points internal to the reverse transcriptase gene. Thus, it would be necessary to conduct a partial digest with DdeI or AluI in order to expect to recover a full length gene. Another cleavage site other than SalI which is located distal to the reverse transcriptase gene is that of StuI (at 4987).

Having isolated DNA encoding the reverse transcriptase gene which bears terminal ligation sites, the DNA is ligated into a replicable vector. The vector will be selected depending upon the intended host, and this in turn on whether the DNA is to be simply replicated or whether it will be desired to use the vector for expression of the enzyme. Ordinarily, the vector will contain a bacterial origin of replication and an antibiotic selection gene, e.g. for tetracycline resistance. These elements are available in a large number of publicly known plasmids such as pBR322. Since it is preferred to express the reverse transcriptase in higher eukaryotic cells, the vector will also contain elements necessary for the stable replication of the gene, for identification of transformants, for promoting the transcription of the gene and for properly terminating the transcribed mRNA in higher eukaryotes. Typically, these will be respectively, the SV40 origin of replication and a source of T antigen (such as supplied by chromosomal integrants found in such cell lines as COS-1, available from Cold Spring Harbor Laboratories), a gene encoding mouse thymidine kinase, the SV40 early or late promoters and the Hepatitis B surface antigen polyadenylation site. Such vectors are known, for example, see EPA 73,656; 92,182 and 93,619 all of which are incorporated by reference.

Known vectors may not contain convenient restriction sites for direct insertion of the reverse transcriptase DNA obtained as described above. This will not constitute an obstacle to those skilled in the art since methods are known per se for introducing new restriction sites or for converting cohesive-ended restriction terminii into blunt ends. For example, the hepatitis surface antigen gene in pHS94 of EPA 73,656 is excised by EcoRI and BamHI digestion, EcoRI and BamHI linkers ligated to the BglII and SalI sites of the cDNA fragment, respectively, and the modified cDNA ligated into the vector fragment obtained from the pHS94 digestion. Then the construction is completed in accord with EPA 73,656.

The vector bearing the reverse transcriptase gene is transfected into permissive hosts such as the COS-1 monkey kidney cell lines or the CHO (Chinese hamster ovary) cell line. Other stable eukaryotic cell lines may be employed as hosts, as well as yeast and prokaryotes where appropriate origins of replication and promoters are provided (for yeast, the two micron origin and a promoter such as that of metallothionein, and for bacteria the pBR322 origin and a promoter such as trp which is described elsewhere herein in connection with expression of the gag and envelope proteins of the AIDS associated retrovirus in prokaryotes).

In this connection, other AIDS associated retroviral proteins such as gag and envelope polypeptides may be expressed in eukaryotic cells, whether yeast or mammalian, as such cells bear a more immediate phylogenetic relationship to the normal retroviral hosts than do prokaryotes.

The reverse transcriptase is preferably synthesized in recombinant culture under the control of an inducible promoter so that any toxic effects of the polymerase on the cell are minimized until a generous amount of mRNA has accumulated. Alternatively, the gene encoding the enzyme is ligated at its 5' end to a signal sequence recognized and processed by the intended host, which in the case of higher eukaryotes, for example, include the known secretion signals for interferons, secreted hormones like insulin or viral surface antigens.

B. Assay of Reverse Transcriptase Inhibition

A cell culture expressing AIDS reverse transcriptase is lysed and divided into aliquots. Various amounts of the compound to be assayed are added to each aliquot of lysate. An oligonucleotide of polyA together with oligo dT primers and $^{32}P$ labelled TTP is added to each aliquot. After incubation at 37° C., the amount of acid precipitated counts is determined. Those compounds which inhibit AIDS reverse transcriptase but which do not comparatively inhibit human DNA polymerase are then selected for further in vitro toxicity and efficacy studies.

Alternatively, AIDS reverse transcriptase is recovered from an expression host by methods known per se, including immunoaffinity adsorption, Sephadex gel filtration, ion exchange chromatography and electrofocusing on native polyacrylamide gels. The recovered reverse transcriptase is then used to assay compounds as described above.

EXAMPLE 7

Cloning and Expression of the E' Polypeptide

Figures 1, 2L:
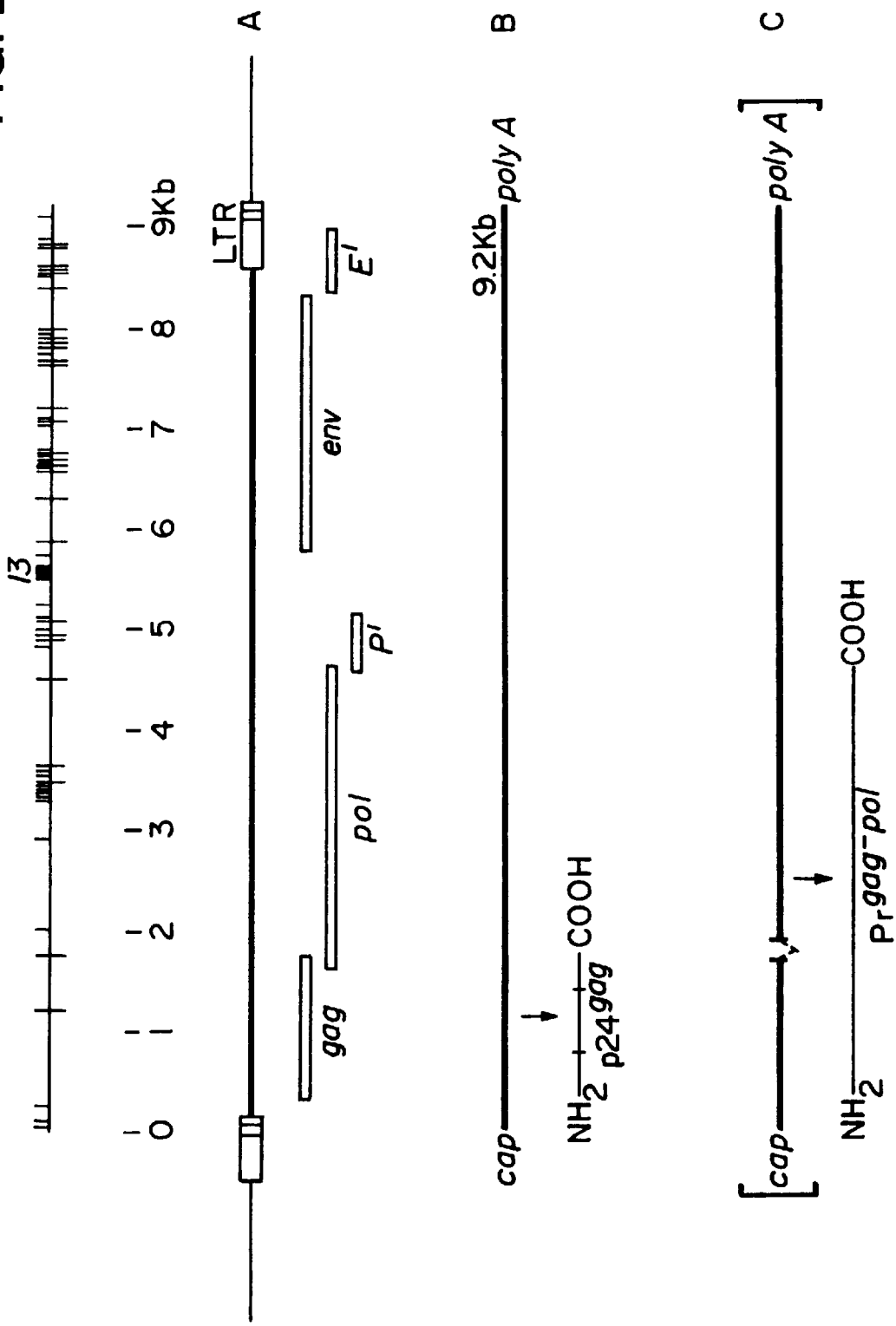
Figure 3A:
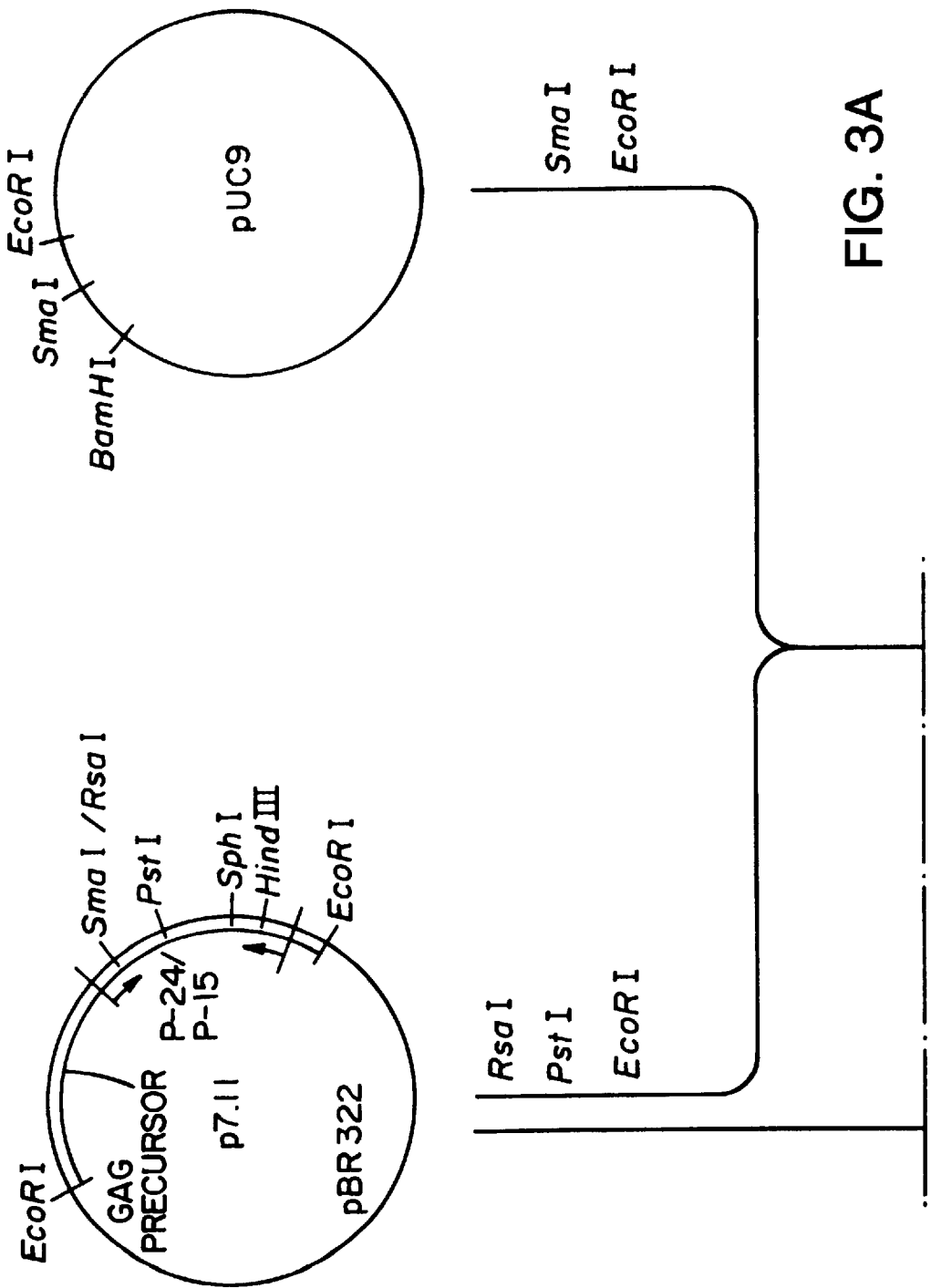
FIGS. 3A–3B depicts the strategy employed to subclone p7.11.
Figure 3B:
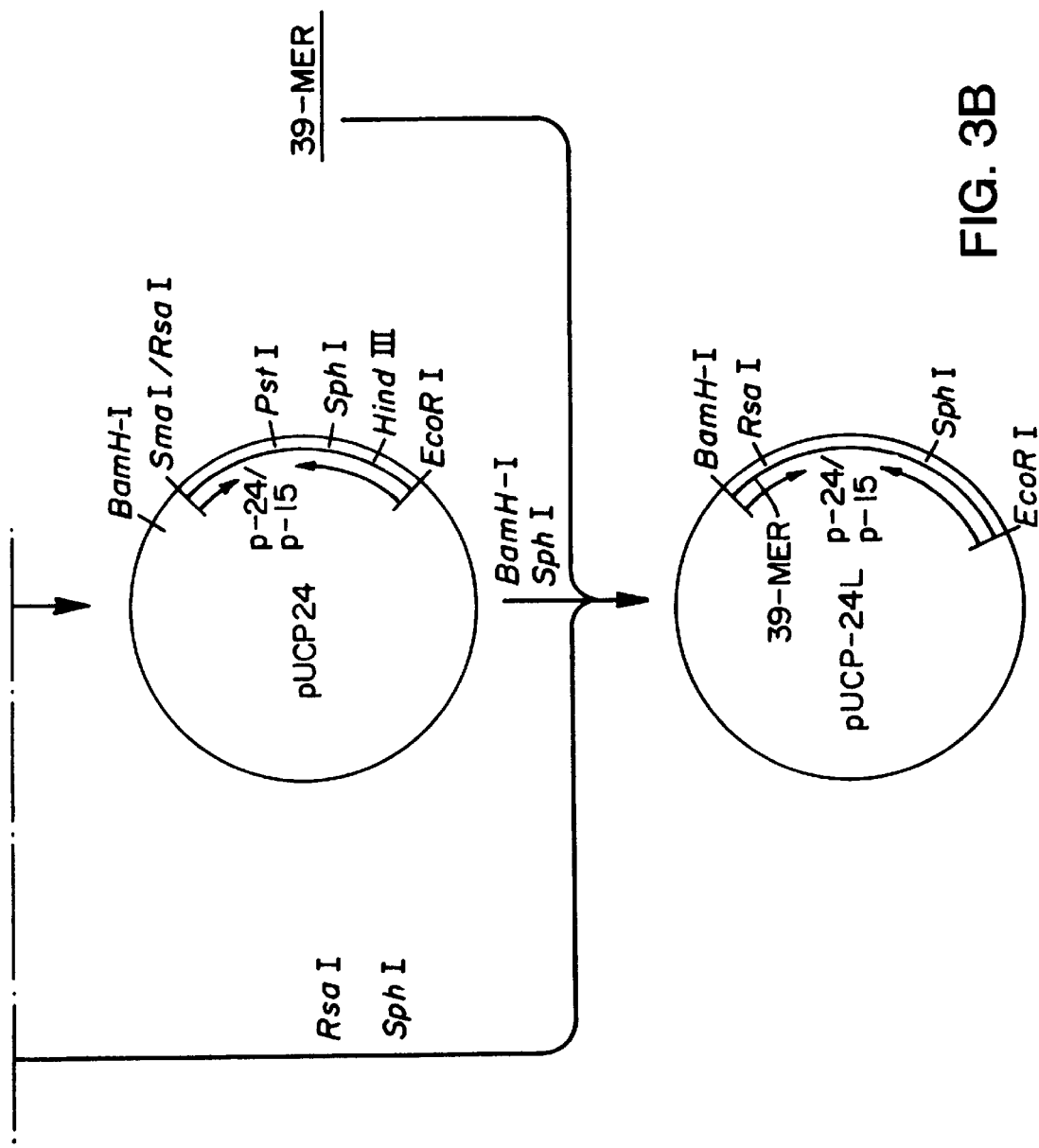

An E' polypeptide of AIDS-associated retrovirus is defined as the 206 residue polypeptide designated "E'" in FIG. 2, its naturally-occurring alleles, or its amino acid sequence variants which are immunologically cross-reactive with antisera capable of binding the E' polypeptide produced in cells infected with AIDS-associated retrovirus. In addition to the C-terminal deletional derivatives described below, other deletions, insertions or substitutions that do not substantially change the immunoreactivity of the peptide with sera from patients infected with HTLV-III or other AIDS-associated retro viruses are included within the scope of the term "E' polypeptide" or "E' protein" as used herein. A further example of a deletional variant is E' protein in which the first 19 residues, through $Arg_{19}$, are deleted. The trpLE fusion described below is an insertional variant. Other variants will be apparent to the ordinary artisan. They are readily produced by methods of recombinant synthesis or, in the case of certain deletions, by proteolytic hydrolysis.

In accordance with this invention, E' polypeptides are produced by recombinant methods so as to be free of proteins from AIDS-associated retrovirus-infected cells that are not encoded by the AIDS-associated retrovirus. Such polypeptides obviously are not present in AIDS-associated retrovirus virions.

cDNA clone H9.c53 contained the E' sequence. The E' sequence is shown in FIG. 2 commencing at nucleotide 8375. The first stop codon in reading frame downstream from the ATG at 8375 is an OP stop codon at nucleotide 8993. The Cys residue immediately preceding this stop codon presumably is the C-terminus of the E' polypeptide. However, other C-terminii upstream from this Cys residue also are within the scope of this invention. E' polypeptides include sequences that are C-terminated at any residue within about the last 50 residues shown in FIG. 2, preferably immediately adjacent and downstream from a lysinyl or argininyl residue.

An expression plasmid for the synthesis of a fusion of the E' polypeptide of FIG. 2 with a bacterial polypeptide is described hereafter. One aliquot of H9.c53 was digested with HaeIII and XhoI and the 62 bp fragment coding for E' residues 14–34 recovered (fragment 1). Another aliquot was digested with XhoI and HindIII and the 719 bp fragment was recovered which encodes amino acids 35–206 and contains the stop codon followed by untranslated 3' sequence (fragment 2).

A synthetic oligonucleotide (fragment 3) was prepared (35) having the following sequence encoding the first 13 residues of the E' polypeptide flanked at its 5' end by an EcoRI cohesive terminus and ending with a 3' blunt end for ligation to the HaeIII-generated blunt end of fragment 1.

Figure 9A:
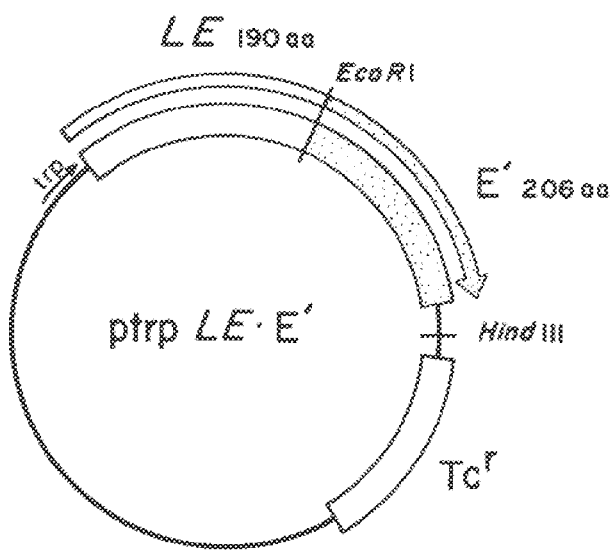

PAATTCATGGGTGGCAAGTGGTCAAAAAGTAGT-G T G A T T G G A T G G - O H
HO-GTACCCACCGTTCACCAGTTTTTCATCAC-ACTAACCTACCP pNCV(55a) was digested with EcoRI and HindIII, which are unique sites in pNCV, and the vector fragment recovered. This vector fragment was ligated simultaneously to fragments 1, 2 and 3, the ligation mixture transformed into *E. coli* 294 and antibiotic resistant colonies identified. ptrpLE-E' was obtained from a resistant colony by preparation of plasmid DNA. The structure of this plasmid is shown in FIG. 9*a*.

ptrpLE-E' contains a continuous open reading frame encoding a bacterial (*E. coli*) derived protein (LE) fused at its C-terminus to the full E' sequence.

This plasmid was enployed as follows to prepare the E' protein fusion (LE-E'). ptrpLE-E' was transformed into *E. coli* strain 294, grown overnight in LB broth (32) containing 5 mcg/ml tetracycline, diluted 1:50 into M9 broth (32) containing tetracycline and grown at 37° C. to an absorbance of 0.5 at 550 nm. Total cell proteins were prepared from 25 ml of induced cell culture. Cells were resuspended in 1/250 volume of 0.01M Tris-HCl pH7.5, 0.001M EDTA, 0.03M mercaptoethanol and 0.8% SDS, boiled for 2 minutes and precipitated with 3 volumes of cold acetone. The precipitated proteins were redissolved by boiling in SDS-polyacrylamide gel loading buffer (40).

Figure 9B:
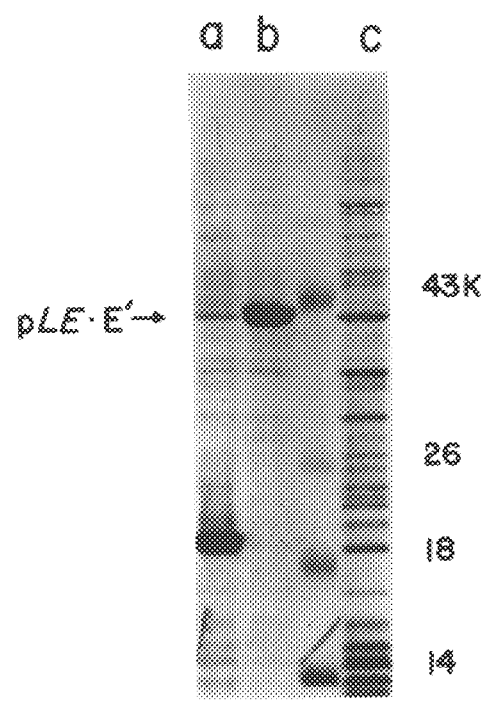
Figure 10A:
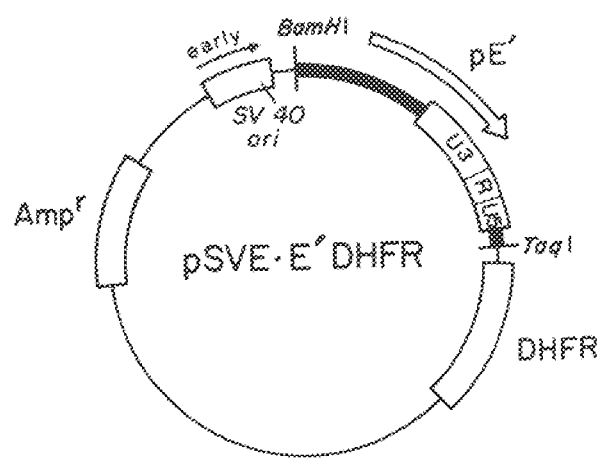
Figure 10B:
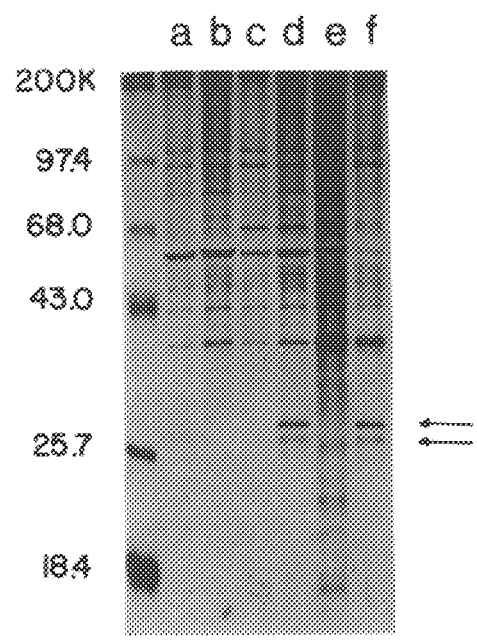

Initial attempts to directly express unmodified E' sequences in *E. coli* were unsuccessful due to an apparent instability of the protein. However, the foregoing method gave efficient expression of the E' polypeptide in *E. coli*. LE is a protein of 190 residues derived from translated sequences of the trp leader and trpE gene product (55b), which forms stable, insoluble aggregates in vivo and has been used successfully to stabilize synthesis of other foreign proteins in *E. coli* (55c, 55a). Expression of the LE-E' fusion protein from ptLE-E' is under the control of an *E. coli* trp promoter and trp leader ribosome binding site (FIG. 9*a*). Cultures of *E. coli* transformed with ptrpLE-E' were grown under conditions of tryptophan depletion as described above to derepress the trp promoter, and their proteins analysed by electrophoresis on 10% SDS-polyacrylamide gel and staining with Coomassie blue. As shown in FIG. 9*b*, cells containing plasmid ptrpLE-E' accumulate a prominent protein of Mr 41,000 (lane b), which is not present in cultures of *E. coli* transformed with pBR322 (lane c). The Mr 41,000 protein has two important characteristics of the expected LE-E' fusion protein. First, this protein is seroreactive with antisera to LE, and second, it has an Mr of 22,000 greater than LE (FIG. 9*b*, lane a) consistent with the size predicted for a protein containing 206 additional amino acids.

To determine whether LE-E' exhibits antigenic sites recognized by human sera following exposure to the AIDS retrovirus, total cell proteins extracted from *E. coli* transformed with ptrpLE-E' were employed as an antigen in a Western blot assay. Note that individual sera were first preadsorbed with a soluble extract of *E. coli* proteins (blocking extract), although this was later found to be unnecessary.

In the Western blot assay, total cellular proteins were prepared from induced cultures of *E. coli* transformed with ptLE-E' (FIG. 9*a*) or ptrpLE-gp41 (described above) and electrophoresed on SDS-10% poylacrylamide gels as described above. Proteins were electrophoretically transferred to nitrocellulose sheets as described(55e). Individual blot strips were incubated overnight at room temperature with a 1:200 dilution of the indicated sera in TBS buffer (0.025M Tris-HCl pH7.2, 0.15M NaCl and 0.05% Tween-20) containing 5% normal goat serum and 5 mcg/ml protein blocking extract from *E. coli* transformed with pBR322. Blocking extract was prepared by sonicating bacteria in 0.01M Tris-HCl pH 7.5, 0.15M NaCl and 0.5% NP40, and removing the insolue residue by centrifugation at 10,000×g. total cell proteins prepared from *E. coli* transformed with pNVC or ptrpLE-E' were employed for preadsorption of sera with LE or LE-E' proteins, respectively. After extensive washing in TBS buffer, the strips were successively incubated with biotinylated goat anti-human or anti-rabbit IgG (Vector Labs), avidin conjugated horseradish peroxidase (Miles-Yeda) and developed with peroxidase substrate (0.5 ng/ml 4-chloro-1-napthol and 0.16% hydrogen peroxide in TBS). Following each incubation, strips were washed extensively with TBS.

Sera from 37% of AIDS patients (17/46), 81% of ARC patients (21/26), and 39% of healthy homosexual men (29/75) tested gave a clear reaction with the LE-E' immunoblots, while none of 37 sera from random blood donors was found to react (Table 1 below). Identical results were obtained for a representative subset of these sera in Western blot experiments in which total cell proteins from *E. coli* transformed with plasmid ptrpLE17-E', a derivative of ptrpLE-E', were utilized as the antigen. These cells express LE17-E', a fusion protein that differs from LE-E' in that nly residues 1–17 of the LE protein are present, indicating that the seroreactivity detected between AIDS-related sera and LE-E' fusion proteins is specific for epitopes associated with E' sequences.

TABLE 1

Prevalence of antibodies to bacterial LE-E' in AIDS risk groups

| Risk group | E'+ | gp41+ | E'+/gp41+ | E'+/gp41− | E'+/gp41+ | E'+/gp41− | WB+ | WB+gp41+ |
|---|---|---|---|---|---|---|---|---|
| AIDS | 17/46 | 44/46 | 16/46 | 1/46 | 28/46 | 1/46[a] | 45/45 | 44/46 |
| ARC | 21/26 | 22/26 | 19/26 | 2/26 | 3/26 | 2/26 | 22/26 | 22/26 |
| HHM | 29/75 | 24/75 | 18/75 | 11/75 | 6/75 | 40/75 | 24/75 | 24/75 |
| cntrls | 0/37 | 0/37 | 0/37 | 0/37 | 0/37 | 0/37 | N.D.[b] | N.D. |

E', reactivity in LE-E' western blot assay; gp41, reactivity in LE-gp41 western blot assay (see Examples above); WB, reactivity in whole virus western blot assay; HHM, healthy homosexual males; controls, random blood donor samples.

(a) This individual ws positive in an HTLV-III cultivation assay (b) All 37 control sera were seronegative in a commercial whole virus ELISA (Abbott)

Two major points are evident from this comparison of LE-E' and gp41 seroreactivity in different AIDS risk groups. First, LE-E' seroreactivity is far less frequently detected than gp41 seroreactivity in AIDS patients (37% vs. 96%), but with roughly the same frequency with sera from ARC patients (81% vs. 85%) and healthy homosexual males (39% vs. 32%). Secondly, a significant number of the healthy homosexual males were seropositive for LE-E' but not gp41 (11/75). The fact that antibodies to E' are detectable sooner than antibodies to env antigens in a statistically significant number (11/75) of healthy homosexual males, a group at high risk for developing AIDS and ARC, as well as a smaller number of AIDS and ARC patients (3/72), was completely unexpected and surprising particularly since no protein of the Mr of E' has been identified as a virion component and, because E' contains no apparent secretory leader, it would not be expected to find the protein in the serum. Seroconversion to env antigens was monitored by Western blots utilizing either whole HTLV-III virus (55e) or a recombinant LE-gp41 antigen (supra), each assay having a reliability of >98% in detecting sera from clinically diagnosed AIDS patients. Since many of the healthy homosexual men studied here were seronegative for E' as well as virus antigens and consequently may not have been exposed to the virus, the actual frequency of E'+gp41− individuals in this sample may be as high as 31% (11/35). These results may be related to previous observations that HTLV-III can be isolated from the lymphocytes of symptom-free seronegative persons (55 m), and have considerable practical importance for the early clinical diagnosis of and screening for AIDS retrovirus exposure.

In contrast to the situation found for asymptomatic individuals with virus exposure and ARC patients, antibodies to E' are detected at a much lower frequency than antibodies to gp41env in AIDS patients (37% vs. 96%). A similar pattern of less freguent reactivity among AIDS patients has been previously noted for the core protein p24gag relative to the major envelope protein gp120env in radioinuunoprecipitation analysis (55 n). It is unclear whether this phenomenon represents a differential susceptibility to developing AIDS, but more likely reflects the selective loss of antibody titers or lower titers to E' and p24gag than to viral envelope antigens.

To obtain direct evidence for E' expression in HTLV-III-infected cells, high titer antisera specific for E' were prepared by immunizing rabbits with LE-E' isolated by preparative SDS-polyacrylamide gel electrophoresis. The region of the gel containing LE-E' (about 100 mcg) was excised, homogenized in incomplete Freund's adjuvant and administered subcutaneously at two week intervals. The rabbit sera were screened for the ability to immunoprecipitate E'-related proteins from extracts of HTLV-III-infected cells metabolically labelled with $^{35}$S-cysteine. The publicly available H9/HTLV-IIIB cell line was employed for this purpose, since we had previously observed that these cells produce a high level of 1.7–1.9 kb mRNAs potentially capable of encoding an E' translation product (~1% of polyA+ RNA) (55e). Following four injections of antigen, sera obtained from two rabbits were capable of immmoprecipitating 5–6 distinct proteins of Mr 23,500–28,000 from B9/HTLV-IIIB cells. Preimmune sera from the same animals failed to immunoprecipitate any one of these proteins. Furthermore, the immune sera did not detect any of these proteins in uninfected H9 cells. The proteins detected in H9/HTLV-IIIB cells by the immune sera included three major proteins of Mr 28,000, 25,500 and 25,000 and two minor proteins of Mr 26,500 and 23,500. In some experiments the Mr 23,500 protein could be resolved into two distinguishable species.

LE-E' positive sera from 3 AIDS patients and 1 ARC patient were capable of immunoprecipitating proteins from the HTLV-III infected cells of Mr 28,000 and 25,000 that were not precipitated by sera from control donors. The immunoprecipitation of these proteins could be only partially displaced by LE-E' protein, however, suggesting that the LE-E'+ AIDS and ARC sera recognize E' determinant(s) not displayed by the recombinant protein.

This rabbit antiserum contained antibody capable of binding AIDS-associated retroviral E' polypeptide but was free of any antibody capable of binding any other AIDS-associated retroviral-encoded polypeptide as well being free of bound E' polypeptide. It conventionally is immobilized to facilitate separations. For example, the antiserum or antibody is bound or adsorbed to a polyolefin, e.g. polystyrene microtiter plate wells, or to matrices to which anti-rabbit IgG (e.g. goat) has been preadsorbed.

The E' protein next was expressed in recombinant mammalian cell culture. Applicants' starting plasmid was obtained from pFD11 (EP 117,060 A) by a complex procedure using certain plasmids conveniently available to applicants. This procedure is not preferred for use by the art. Instead, the starting plasmid is preferably obtained from pFD11 by the following method. pFD11 is digested with HindIII at its unique HindIII site and the vector recovered. An adaptor having the sequence

AGCTTGGATCCTTTTTATCGATA
ACCTAGGAAAAATAGCTATTCGA is ligated to the vector fragment and transformed into E. coli 294. pFD11d Is obtained from an ampicillin resistant colony. The ligation of the adaptor into pFD11 introduces BamH1 and Cla1 sites immediately upstream from the mouse DHFR gene. pFD11d is digested with BamH1 and Cla1 and the vector fragment isolated.

H9C.53 was digested with BamH1 and TaqI and the fragment (fragment 4) was isolated that contained the portion of the env gene downstream from the BamHI site at nucleotide 8053, the E' coding region and its untranslated 3' region through to nucleotide 232. The untranslated 3' region included the 3' long terminal repeat (LTR). The pFD11d vector fragment (supra) was ligated to fragment 4 and *E. coli* 294 transfected. pSVE.E'DHFR was obtained from an ampicillin resistant colony. The E'-encoding DNA thus was placed uner the transcriptional control of the SV40 early pronoter, while the LTR provided sequences for the cleavage and polyadenylation of the E' gene transcripts together with sequences for promoting transcription of the dhfr gene.

CHO dhfr-K1 DUX-B11 cells (55f) were grown on DMEM medium containing 10% fetal bovine serum. Transfections with pSVE.E'DHFR were performed by the calcium phosphate precipitation method (55g) as described (55h). Following a 6 hour exposure to the vector, the cells were shocked with 20% glycerol (v/v) in PBS (55i) and grown for 1–1/2 days in nonselective medium. Cells were then passaged into selective medium (F12 medium lacking glycine, hypoxanthine, and thymidine and supplemented with 10% dialysed fetal bovine serum) and refed every 2–3 days. A population of approximately 300 resistant colonies was massed after two weeks. Immunoprecipitation analysis of a population of the initial dhfr+ colonies revealed a barely detectable level of E'. This population was further amplified for pSVE.E'DHFR by selection for growth in methotrexate (55j, 55k). Approximately $2 \times 10^5$ cells were seeded into a 100 mm dish of selective medium containing $10^{-7}$M methotrexate and the media changed every 2 days. A population of approximately 50 resistant colonies arising after three weeks in this media (CHO/E'.100) was massed and E' protein recovered as follows. The cells were collected by centrifugation, washed with phosphate buffered saline (PBS) and lysed in 2 ml of RIPA buffer (0.05M Tris-HCl pH7.5, 0.15N NaCl, 1% Triton X-100, 1% deoxycholate and 0.1% sodium dodecyl sulfate) containing 0.5% aprotinin. The extract was preincubated for two hours with 10 mcl. of preimmune rabbit sera at 4° C., cleared twice with 50 mcl. of Pansorbin (Calbiochem), and incubated overnight with 2 mcl. of rabbit anti-LE-E' sera at 4° C. The immunoprecipitate was incubated for 30 minutes with 10 mcl. of Pansorbin, collected by centrifugation and the pellet washed twice with RIPA buffer and once with water. The immunoprecipitate is solubilized and E' separated from the rabbit antibody by ultrafiltration, electrophoresis or other conventional technique. On a commercial scale the antibody or antisera is preinsolubilized and E' eluted from the immobilized immmunoadsorbent using pH 3–5 buffer.

The population of colonies arising in $1 \times 10^{-7}$M methotrexate (CHO/E'.100) produced significant amounts of two E'-encoded proteins specifically immunoprecipitated by the rabbit sera to LE-E' but not preimmune rabbit sera. Neither protein was detectable in the parent CHO cells with the immune sera. Furthermore, immunoprecipitation of both E'-related proteins detected in CHO/E'.100 cells was readily competed by the LE-E' protein but not the LE protein, demonstrating that the reaction was specific for E' sequences.

A direct comparison shows that the two E'-related polypeptides made in CHO/E'.100 cells have electrophoretic mobilities identical with Mr 28,000 and 26,500 proteins observed in H9/HTLV-IIIB cells. In addition, the relative amounts of these two proteins in CHO/E'.100 and H9/HTLV-IIIB cells are essentially identical. However, it is uncertain whether the 28,000 and 26,500 H9/HTLV-IIIB cell proteins are chemically identical to the E'-related recombinant polypeptides, produced herein. Pulse-labeling studies indicated that neither protein in CHO cell culture is the direct precursor of the other. Approximately 80–90% of the Mr 28,000 and 26,500 E' protein was contained within the cytosolic fraction of transfected CHO cells. Immunoprecipitation of cell supernatants from CHO/E'.100 cultures did not reveal any secreted E' proteins.

The recombinant E'-polypeptides are sterilized by passing a solution of the polypeptides through a 0.22 micron filter in order to remove bacteria. The filtrate is formulated into a vaccine by further purifying the polypeptide, for example by gel filtration, as desired and formulating the polypeptide into a pharmaceutically-acceptable carrier such as isotonic saline, D5W and the like. The amount of E' protein employed will be sufficient upon S.C. injection, followed by i.v. boost, to generate a detectable titer of anti-E' in the subject. This will necessarily turn on the immunocompetence of the test subject, so the dose frequency and route of administration of antigen must be determined by the attending physician through monitoring of the serum anti-E' levels. E'-containing vaccines optionally include other predetermined AIDS-associated retroviral polypeptides such as gp41. This will be helpful in ensuring a complete potentiation of the immune response to a potential AIDS-associated retroviral infection. The role of the E' gene protein in viral reproduction and pathogenesis remains a major unanswered question raised by these studies. Our ability to readily detect individuals who are seroreactive with LE-E' but not with whole virus antigens on immunoblots suggests that E' is not a virion component, but could also be explained if E' were lost during virus purification. Others have described unidentified proteins of Mr 25,000–28,000 in HTLV-III-infected H9 cells immunoprecipitated by AIDS-related sera (55o, 55n,55p), which may correspond to E' proteins, but the same polypeptides were not detected in HTLV-III virion preparations (55o,55p). In CHO/E'.100 cells most intracellular E' was found in cytoplasmic rather than nuclear fractions, suggesting that E' does not participate in a nuclear event such as transcription initiation. These studies must be considered preliminary, however, since they may not accurately reflect the location of E' in infected cells.

Transcriptional mapping studies have suggested that E' may be an abundantly expressed protein in infected cells. Approximately 20% of the viral RNA synthesized in H9/HTLV-IIIB cells represents a family of spliced, subgenomic 1.7–1.9 kb RNAs consisting of a 289 bp leader containing sequences 5' to gag, a middle exon located upstream of env, and 1.3 kb of sequence from the 3' end of the genome containing the E' gene (55e). Either of two additional short untranslated leaders from the pol or P' regions may also be present. Depending upon alternate utilization of two splice acceptor sites (at nucleotides 5,359 and 5,558), a middle exon of either 268 bp or 69 bp is generated (55e, 55q). The 268 bp exon contains two AUG triplets not present in the 69 bp exon, one of which may serve as the initiator codon for the tat reading frame (55q). In 1.7–1.9 kb mRNAs that contain the 69 bp middle exon the predicted E' AUG initiator codon is preceded by a single AUG triplet, but we nonetheless expected it to be utilized efficiently for translation initiation since the upstream AUG triplet is flanked by unfavorable nucleotides (55r) and is followed by an in-frame termination codon well upstream of the E' AUG initiator (55s). Our ability to obtain efficient expression of E' proteins in CHO cells with a plasmid containing the upstream AUG triplet (pSVE.E'DHFR) confirmed our expectation. Alternative usage of the two middle exons within the 4.3 kb viral mRNA class (55e), similarly determines whether the tat reading frame precedes the env gene. If differential splicing is the mechanism for generating mRNAs encoding either the E' and env proteins or the tat reading frame, it may represent a crucial regulatory event in the reproduction of the AIDS retrovirus.

E' polypeptides or antibodies thereto are employed in conventional assay procedures as are generally described above. For assay of the E' polypeptide in the body fluids of test subjects (serum, saliva, plasma, urine, etc.), a "competitive" type test kit preferably will contain labeled (enzyme, radioisotope, fluorescent group, etc.) E' polypeptide such as LE-E' or either species of E' described above, antibody capable of binding E' polypeptide and, optionally, other conventional reagents such as incubation and washing buffers. This test kit is employed in methods known per se for use with the selected label, e.g. ELISA, radioimmunoassay or fluorescence polarization. Similarly, conventional "sandwich" assays also are useful in determining the presence of E' polypeptide or its antibody in test subject samples. Assays for the E' protein are unusual for AIDS diagnosis because they are the first known that are directed at determining a protein which is not present in purified preparations of the AIDS virion but which are encoded by the viral genome and apparently expressed by host cells in the course of a viral infection and/or replication in vivo. Detection of such proteins is a preferred diagnostic approach because they are believed to constitute the first indicia of viral infection, preceding the accumulation of virion antigens such as env and the generation of host antibodies directed against HTLV-III-encoded proteins.

It also is within the scope of this invention to assay body fluids for DNA or RNA encoding the E' protein using standard hybridization assays, e.g. Southern or Northern assays, respectively. DNA or RNA is used in such assays that is merely capable of hybridizing with the FIG. 2 E'-encoding sequence; it need not encode an E' protein. Such nucleic acids are readily synthesized as oligonucleotides and then screened for the ability to hybridize to the E'-polypeptide encoding DNA set forth in FIG. 2. The diagnostic nucleic acid is labelled in conventional fashion using detectable tags such as radiophosphorus and the like.

EXAMPLE 8

Figure 11A:
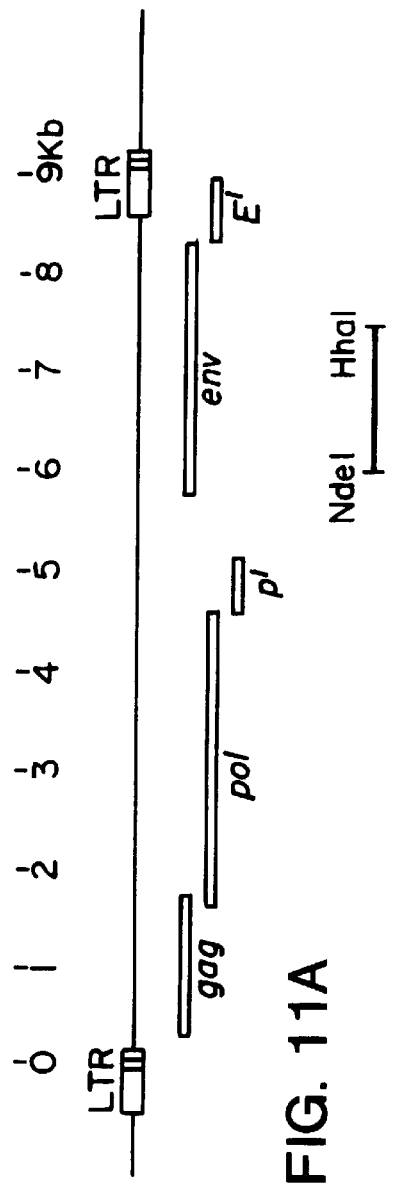
FIG. 11A shows the region of the HTLV-III genome used for env protein preparation in recombinant higher eukaryotic cell culture.
Figure 11B:
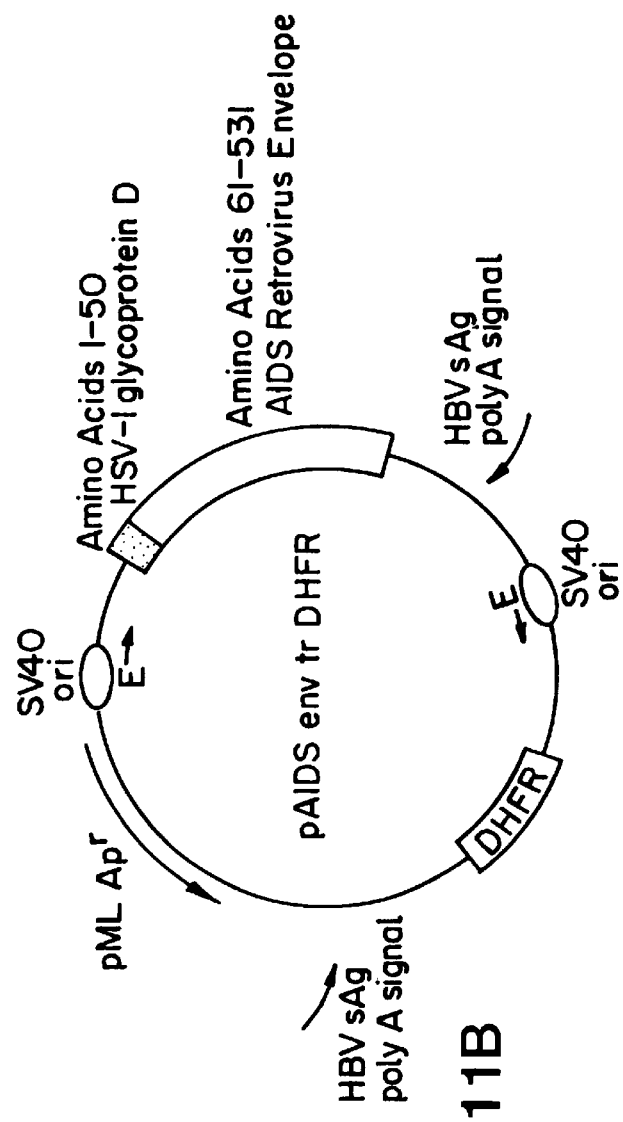
FIG. 11B depicts an expression plasmid for secreting an HTLV-III envelope protein from cultured mammalian cell culture transformants.

Recmmbinant Snthesis of a Secreted Form of An HTLV-III Retrovirus Envelope Protein in Mammalian Cells FIG. 11a illustrates the viral genome with the location of each of the five major open reading frames of the virus. The env reading frame encodes the viral envelope antigen utilized here. An envelope fragment encoding amino acid residues 61–531 was used for expression of a secreted envelope protein. This fragment was ligated to a vector which contained the components necessary for proper expression of this integrated envelope gene as well as for selection in mammalian cells. "SV40 ori" contains an early promoter from the SV40 virus ("E") which is utilized to drive transcription. of either the AIDS retrovirus envelope or the dihydrofolate reductase (dhfr) gene. Transcription termination and message polyadenylation are accomplished using signals derived from the 3' non-translated region of the hepatitis B virus surface antigen gene ("HBV s Ag poly A signal"). Growth in E. coli is accomplished by the inclusion of the ampicillin resistance gene ("Ap R") of pBR 322 as well as the origin of replication of this plasmid. Finally, the murine dhfr gene is utilized as a selectable marker for transfection and selection in chinese hamster ovary (CHO) cells which lack this gene.

A. Construction of Expression Vector

The contemplated method for assembling this vector from publicly available starting plasmids is as follows, this being a modification of that method which was actually used. pE348HBV E400D22 (also called pE342HBV E400D22, European patent application 117,058A) is digested with HpaI and the linearized plasmid recovered (fragment 1). Those skilled in the art recognize that the most efficient ligation in the next step is achieved when the opened plasmid is treated with bacterial alkaline phosphatase. This prevents insert-less recircularization of the plasmid. A blunt-ended duplex stop linker having the coding sequence TCTAGAGGATCCCCAACTAA-GTAAGATCTAG is ligated to vector fragment 1, the ligation mixture transfected into E. coli 294 and the vector recovered from an $Amp^r$ colony. Since the insert is blunted at both ends it is conventional to confirm that the recovered plasmid contains the insert in the correct orientation. The underlined sequences represent stop codons in each of the three possible reading frames. The inclusion of the stop linker introduces a synthetic nine-residue polypeptide at the C terminus of the env protein.

The stop-linkered vector is digested with XbaI, blunted with Klenow, partially digested with EcoRI and a 5706 bp vector fragment 2 recovered. This digestion serves to remove the hepatitis B surface antigen coding sequence.

Clone H9c.53 described above which contained HTLV-III retroviral env cDNA is digested with HhaI, blunted with Klenow, digested with EcoRI and the approximately 1.6 kB env-containing fragment 3 ligated to vector fragment 2. A vector 4 containing the complete envelope gene is recovered from an $Amp^r$ colony. This vector is digested with NdeI, blunted with Klenow, and then partially digested with PstI. Vector fragment 5 is recovered, wherein the sequence located between a nucleotide located within the $Amp^r$ gene in the 3' direction up to residue 61 of the env protein is removed. This removes the 61 N-terminal residues of the env protein, including the retroviral signal, the mature N-terminal residue being at residue 31 of the gp160 preprotein.

pgDtruncDHFR (EP 139,417A) is digested with PstI and PvuII and 1514 bp fragment 6 recovered containing (a) the 3' portion of the $Amp^r$ $Amp^r$ gene (corresponding to that part of the sequence removed from vector 4 in the previous step), (b) an SV40 origin, (c) the 25 residue herpes gD protein signal and (d) the first 25 N-terminal residues of the mature gD protein. Fragments 5 and 6 are ligated, the ligation mixture transformed into E. coli 294 and pAIDSenvtrDHFR was recovered from an $Amp^r$ colony.

In a closely related alternate method for constructing an expression vector for gp120, pEH3Bal14 (also referred to as pEHBal14, EP 139,417A) vas used in place of pE348HBV E400D22 and constructed as described above except that the DHFR gene was supplied by digesting pgDtruncDHFR with EcoRV and Sal and an approximately 4 Kb fragment 7 recovered. The DHFR gene also can be supplied from pE342 (EP 73,656A) or any other DHFR plasmid. Vector 5 was digested with EcoRV and Sal and and vector fragment 8 recovered containing the truncated env gene. Fragment 7 and 8 were ligated and pgDHTLV3TRDHFR was recovered from an $Amp^r$ colony.

The skilled artisan will appreciate that the above described vectors for the expression of a gp120-viral protein fusion are suitably modified for expression as fusions with other viral polypeptides than those of herpes simplex. For example, a fusion with hepatitis surface antigen is readily accomplished by inserting DNA encoding the mature truncated or intact gp41 or gp120 protein in place of the surface antigen stop codon, or vice versa, using for example pE348 HBV as a starting plasmid. Selection of appropriate restriction sites and synthetic adaptors as required will be within the skill of the ordinary artisan.

Signal sequences other than the herpes gD signal are used as well. Suitable signals include those of secreted eukaryotic polypeptides or secreted polypeptides of mammalian host range viruses which are known per se.

B. Transfection and Selection of Mammalian Cell Lines

On the day prior to transfection, cells from a confluent 10 $cm^2$ dish of CHO $DHFR^-$ cells were split 1:10 into 2 $10cm^2$ dishes in F12/DMEM (Delbecco's modified Eagles medium), 10% FBS (fetal bovine serum)+GHT (glutamine, hypoxanthine, thymidine)+penn-strep antibiotics and grown overnight at 37° C.

Preparation of Plasmid for Transfection

75λ 10 mM Tris, 1 mM EDTA 10 μg Plasmid DNA (omitting DNA for mock transfection), 65 λ $CaCl_2$ and 0.65 ml 2×hepes buffer, pH7.1 were carefully mixed at room temperature, and thereafter poured directly on the CHO cells with media. Cells and DNA were incubated at 37° C. for 3 hours. The media were then aspirated and the CHO cell uonolayers shocked with 20% glycerol-PBS (2.5 ml) for 45 sec. The dishes were flooded with 7.8 mls of F12/DMEM, aspirated and replaced with 12 ml F12/DMEM. Cells were incubated at 37° C. for 2 days and then split 1:2 and 1:10 in F12 media containing 7% XDZ,FBS (extensively dialyzed fetal bovine serum), with penn-strep. The cells were fed again on day 4.

Selection and Amplification of New Cell Line

On day 7 the mock transfected cells were all dead. The transfected CHO cells split 1:2 and grown to confluence. They were split 1:.3 into 3 10 $cm_2$ dishes containing F12/DMEM, 7% XDZ, 50 nM MTX (Methotrexate)-100 nM MTX and 250 nM MTX. The dishes were refed every 4 days until confluent monolayers had adapted to MTX. The monolayers were then labelled in $^{35}$S-met and assayed by immunoprecipitation for the secreted env fusion.

Cells diluted 1:10 in selection media had 50–100 colonies at day 10. The colonies were picked and clones grown up in F12/DMEM. These clones were screened by radioimmunoprecipitation with anti-env antisera. Positive clones were amplified in increasing concentrations of MTX (500, 1000 and 3000 nM) until maximum secretion of env fusion was observed.

C. Radioimmunoprecipitation Analysis of Transfected CHO Cells

Confluent 10 cm dishes were labelled with 66 μC/ml of 35S methionine for 4 hr at 37° C. in RPMI 1640 medium lacking methionine. The media were then collected and apoprotinin was added (1%). Cells were removed by centrifugation. One ml of supernatant was added to 100 μL of 2.5M NaCl, 2% Tween 80, 1-mg/ml BSA. Two pL of high titer human anti-AIDS antibody was added and incubated 1 hr at room temp. Protein A Sepharose, preadsorbed with non-transfected CHO protein lysates, was added (50 μL) and the mixture incubated 30 minutes at 37° C. The Protein A Sepharose beads were then washed by centrifugation 3 times in PBS, 0.2% deoxycholate, 0.2% Tween 20. A final water wash was followed by resuspension of the Sepharose beads in a standard SDS PAGE sample buffer. The samples were boiled 5 minutes, centrifuged, and the supernatants were separated on SDS polyacrylamide gels. The gels were then autoradiographed using Enlighten 30.

Cells producing large amounts of envelope synthesized a ~120,000 Mr protein which was specifically immunoprecipitable by anti HTLV-III retrovirus antibodies. This protein was found only in plasmid transfected cells. The intracellular form of the antigen was approximately 100,000 daltons in size, and it could be chased, in a pulse-chase experiment, into 130,000 dalton, secreted protein. This protein was also found to react on Western blots when incubated with anti-AIDS retrovirus antibodies.

D. Culture of Amplified Transformant CHO Cells 1 confluent 10 $cm^2$ dish of transformants from step B was incubated with trypsin to free the cells and transferred to a small roller bottle In 50 mls F12/DKEM 50:50 media w/o GHT, low glucose, minus glycine +7% XDZ FBS. $CO_2$ was introduced into the bottle for 5 sec. and capped tightly. The bottle was rolled at 37° C. and observed daily until confluent (~3 days).

The medium was decanted, cells rinsed once in 50 mls PBS, and trypsinized for 5 min. at 37° C. with 5 mls trypsin in EDTA. Cells were suspended in 5 mls of F12/DMEM 50:50 plus 7% SDZ FBS and the suspension placed into 850 $cm^2$ roller bottles. This procedure is continued until the desired number of bottles is obtained. When the desired number of bottles reached about 85% confluency, they were rinsed twice in 100 mls PBS and 125 mls serum-free F12/DMEM 3:1 w/o GHT, low glucose, minus glycine added to each bottle. The bottles were incubated at 37° C. for 3 days. On the third day the media were poured off and retained. This process was repeated twice. The ~375 ml of medium collected from each bottle was centrifuged at 2000 rpm for 5 min and Na Azide added to inhibit any contaminant microbial growth.

E. Purification of Recombinant HTLV III Envelope Protein

E.I. Preparation of an Affinity Column for the Isolation of Recombinant HTLV III Polypeptides Sera from patients diagnosed with AIDS related complex (ARC), were tested for the presence of antibodies reactive with HTLV-III proteins by "Western" immunoblot analysis. Plasma from individuals exhibiting a high titers to HTLV-III envelope protein were collected, and immunoglobulins were purified by affinity chromatography using Protein A-Sepharose CL-4B (Pharmacia Fine Chemicals) according to the manufacturer's directions. The purification procedure yielded material that was approximately 90% pure as judged by polyacrylamide gel electrophoresis (PAGE) visualized by silver staining. The purified immunoglobulins were then covalently linked to Sepharose 4B (Pharmacia Fine Chemicals) according to the manufacturer's instructions.

E.II Purification of Recombinant HTLV-III Envelope Protein Fusion

Serum free cell culture medium from the method of step D was harvested, clarified by passage through a 0.45 micron Nalgene filter, and concentrated 50-fold by ultrafiltration using an Amicon YM-10 ultrafiltration membrane. The concentrated medium was dialyzed against phosphate buffered saline (PBS), and applied to an affinity column of the type described above in E.I. After application of the concentrated cell culture medium, the column effluent was monitored spectroscopically at 280 nm and the column was washed until the effluent was free of material adsorbing light at this wavelength. Proteins retained on the affinity column were eluted by treating the eluted from the column with 0.1M acetic acid, 0.5M NaCl elution buffer. Material eluted from the column was monitored spectroscopically, and was immediately treated with 1M Tris buffer to adjust the pH to near neutrality (pH 7–8). The eluted protein was dialyzed against PBS and concentrated approximately 5 fold by ultrafiltration with the use of an Amicon YM-10 membrane. The resulting protein was analyzed by PAGE and visualized by silver staining and "Western" immunoblotting. Based on these analyses, the secreted truncated recombinant HTLV-III env fusion exhibited a molecular weight of approximately 130 Kd, and represented from 5–25% of the total protein eluted from the is column, depending on the preparation. Neuraminidase digestion of the fusion reduced its size from 130 Kd to about 100 Kd, suggesting that the secreted antigen possessed the complex form of N-linked carbohydrate with terminal sialic acid residues (Hubbard et al., 1981, "Ann. Rev. Biochem." 50: 555–583). The secreted fusion was resistant to endoglycosidase H, but the intracellular 100 Kd form was sensitive, generating a 69 Kd species (Torentino et al., 1974, "J. Biol. Chem." 249: 811–817). These results demonstrated that the intracellular protein possessed the simple form of N-linked carbohydrate (highmannose).

E.III. Immunization of Rabbits with Affinity Purified Recombinant HTLV-III Envelope Protein Fusion Rabbits were immunized with 30–50 micrograms of total protein (prepared as described above) per immunization. For the primary immunization, 30–50 micrograms of protein in 1 ml of PBS was emulsified with an equal volume of complete Freund's adjuvant and injected as follows: 0.5 ml in each rear footpad, 0.2 ml injected at 5 intradermal sites along the back. The rabbits were then boosted 14–21 days after the primary immunization. The antigen emulsion for the booster immunizations was prepared the same way as that for the primary immunization with the exception that incomplete Freund's adjuvant replaced complete Freund's adjuvant. For the booster immunizations each rabbit received a total of 2 ml of antigen emulsion distributed as follows: 0.5 ml intramuscularly in each thigh, and 1 ml distributed among 5 intradermal sites along the back (0.2 ml per site). Animals were bled via the ear vein or cardiac puncture 10 to 14 days after each boost. Antibodies elicited against the recombinant HTLV-III envelope protein were identified by "Western" immunoblot analysis using recombinant HTLV-III 130K protein as the antigen. In the first experiment, one of two rabbits formed antibodies reactive with the recombinant HTLV-III protein after one booster immunization. The second rabbit required additional booster immunizations to elicit the formation of anti-rHTLV-III antibodies.

F. Neutralization of HTLV-III Retrovirus Infection

Various sera from either control rabbits, rabbits inoculated with the recombinant envelope antigen, normal control patients, or patients with known retrovirus neutralizing antibodies were heat inactivated at 56° C. for 30 minutes. The serum samples were then mixed 1:1 with virus in wells containing RPMI 1640, 20% fetal calf serum, penn-strep, and 2 μg/ml polybrene. The wells were incubated 1 hour at 4° C., after which the plates were returned to room temperature for 15 minutes. $1\times10^6$ H9 human T cells were then added to each well, and the wells were incubated in $CO_2$ incubator. The cultures were split 1:1 on day 4. Cells were assayed for reverse transcriptase and immunofluorescence on day 7 or 8. Immunofluorescence assays were done on fixed cells using human antisera known to contain AIDS retrovirus antibodies. The percentage of cells which vere fluorescent was a measure of the percentage of cells which were infected by the virus. Reverse transcriptase assays of cell supernatants were done as described. The reduction in reverse transcriptase levels was indicative of virus neutralization. When either control human or rabbit sera were mixed with the virus, approximately 70–80% of the cells were fluorescent. Reverse transcriptase assays gave approximately $1.6\times10^6$ cpm incorporated. When serum from a rabbit vaccinated with recombinant envelope antigen was analyzed, the percentage of cells fluorescing was 35% and the reverse transcriptase levels were 285,000 cpm. Human serum known to neutralize the virus gave 0% fluorescence and 10,000 cpm reverse transcriptase. These results indicate neutralization with the antiserum from rabbits vaccinated with the recombinant antigen.

EXAMPLE 9

Construction and Expression of gp160, gp120 and Fusions and Truncations Thereof gp160 is the precursor to envelope proteins gp120 and gp41. Infected cells express the intact gp160 molecule and then proteolytically cleave it at a hydrophobic region starting at gp160 residue 517 in the amino terminus of gp41. The objective of this example is to describe a method for preparing gp120, gp160 as well as derivatives thereof containing varying selected gp41 sequences.

H9c.53, the HTLV-III proviral clone described above, was digested with XhoI, the XhoI site filled, digested with EcoRI, and the fragment spanning bp 5324 to 8476 was recovered (Fragment A). This fragment contained the HTLV-III gp160 envelope gene.

pgDHTLV3FL+Pro, encoding the full gp160 sequence, was prepared in the same way as a pgDHTLV3TRDHFR except that fragment A (the full-length gene) was used in place of fragment 3 (the truncated gene with its 3' end at the HhaI site).

pgDHTLV3FL+Pro was transfected into CHO DHFR⁻ cells, and pulse labelled with 35 S methionine in methotrexate in the same fashion as described above in Example 8B.

Transformants were lysed in NP40 lysis buffer and the lysate proteins separated by 7.5% SDS-PA reducing gels. A 160 kD band was identified as gp160 by radioimmunoprecipitation. This gp160 species contained the full length gp41 polypeptide, including the hydrophobic regions having hydropathy hydrophobic levels in excess of about +2 (on a scale of 4), in particular at about residues 512 to 538 and about 684 to 705, as well as all of gp120 except for the 61 amino terminal residues. These are readily inserted by replacing the 25 residues of the gD mature sequence with the missing 61 residues of the gp160 amino terminus.

Additional gp160 truncations

DNA encoding the truncated gp160 fusion in pgDHTLV3FL+Pro was subjected to further manipulation in order to remove DNA encoding gp41 or certain of its subsequences. The object was to prepare envelope antigens containing gp120 and gp41 sequences, but without hydrophobic gp41 regions spanning substantially all of residues 512–538 and 684 to 705. Three expression plasmids were constructed, pFB53, pFB58 and pFB56. pFB53 encodes a gp120 species which is identical to gDtrunc (Example 8) except that the carboxyl terminus is residue 514 rather than 531. This envelope protein also is secreted.

pFB56 encodes a full length gp160 derivative from which substantially the N-terminal hydrophobic domain of gp41 (residues 517 to 540) have been deleted.

pFB58 encodes the same derivative as pFB56 except that, in addition, the carboxyl terminus of gp41 downstream from residue 614 is deleted.

Other envelope derivatives are within the scope hereof. For example, full length gp41 is expressed as a fusion with a heterologous signal (in this case heterologous meaning other than the gp160 signal), and with or without either of the hydrophobic regions described above. The hydrophobic regions are deleted or substituted by hydrophilic domains, derived for example from other AIDS-associated viral polypeptides.

The manipulations giving rise to pFB58, pFB53 and pFB56 will be more readily understood by. reference to the following Table and chart. The chart depicts the flow scheme for plasmid construction that led to each of the 3 final plasmids.

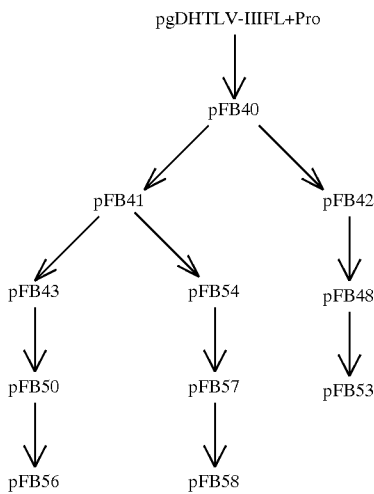

The following Table describes the construction of these intermediate and final plasmids.

restriction enzymes as indicated and the vector fragent recovered in each instance. In the three instances where the recipient plasmid was digested with BglII the vector fragment was treated with bacterial alkaline phosphatase in order to prevent insert-less recircularization of the plasmid during ligation. The donor plasmid fragment was cloned into the recipient by ligating it to the recipient vector fragment, transforming E. coli 294 cells and recovering the product plasmid from ampicillin resistant colonies. In those instances where the insert contained BglII cohesive termini at both ends the product plasmids having the correct orientation were identified by restriction digest analysis.

For expression, each of pFB53, pFB56 and pFB58 were transfected into CHO DHFR⁻ cells and amplified as described in Example 8B. Cell lysates and supernatants were analyzed by radioimmuno-precipitation as described in Example 8C. The expected product encoded by pFB53 was identified in culture fluid. The full length gp160 derivative encoded by pFB56 was identified in cell lysates. The pFB58 eodiment of gp160 is secreted in two forms, one corresponding to the unprocessed protein (unprocessed at the gp120–gp41 processing site) and the other closely resembling gp120, probably representing the gD-gp120 fusion having a C-terminus at the normal gp120-gp41 processing site which is produced by proteolytic removal of the truncated gp41 species encoded by pFB58.

Obviously, the nonradioactive forms of the env proteins described above are produced by culture without 35S methionine. The embodiments of this Example are purified and analyzed for neutralizing activity by the methods described in Example 8E.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

TABLE 2

| Donor Plasmid | Donor Fragment(s)* | Recipient Plasmid | Recipient Fragment | Product Plasmid |
|---|---|---|---|---|
| gD HTLV-III FL + Pro | AhaIII-BamHI (1228 bp) | pUC 13 | SmaI-BamHI | pFB40 |
| pFB40 | 1. EcoRI-Alu (525 bp) 2. BeeIII-HindIII (297 bp) | pUC 13 | EcoRI-HindIII (Fragment a) | pFB41 |
| pFB40 | EcoRI-Alu (525 bp) | pBR322 | ClaI blunt-EcoRI | pFB42 |
| pFB41 | EcoRI-HindIII (822 bp, Fragment b) | pUC 13 | EcoRI-Sma | pFB43 |
| gD HTLV-III FL + Pro | HindIII-EcoRV (977 bp) | | | |
| pFB42 | BglII-EcoRV (314 bp, Fragment c) | gD HTLV-III FL + Pro | BglII-EcoRV (Fragment d) | pFB48 |
| pFB43 | PstI blunt-BglII | gD HTLV-III FL + Pro | Fragment d | pFB50 |
| gD HTLV-III FL + Pro | BglII (580 bp, Fragment e) | pFB 48 | BglII | pFB53 |
| pFB41 | Fragment b | pBR322 | Fragment a | pFB54 |
| gD HTLV-III FL + Pro | Fragment e | pFB 50 | BglII | pFB 56 |
| pFB54 | BglII-EcoRV (612 bp) | gD HTLV-III FL + Pro | Fragment d | pFB 57 |
| gD HTLV-III FL + Pro | Fragment e | pFB 57 | BglII | pFB 58 |

*fragment lengths are approximate

In general, each of the intermediate plasmids was constructed by digesting a donor plasmid with restriction enzymes as indicated and the desired fragment recovered. The recovered fragment was then cloned into a designated recipient plasmid. The recipient plasmids were digested with The references cited herein or grouped in the following bibliography and respectively cited parenthetically by number in the foregoing text, are hereby incorporated by reference.

BIBLIOGRAPHY

1. Emtage et al., *Nature* 283, 171 (1980); Davis, et al. *Proc. Natl. Acad. Sci.* (USA) 78, 5376 (1981); Weiland et al. *Nature* 292, 851 (1981).
2. Kupper, et al., *Nature* 289, 555 (1981); Kleid et al., *Science* 214, 1123 (1981).
3. Charnay et al., *Nucleic Acids Research* 7, 335 (1979); Valenzuela et al., *Nature* 298, 247 (1982).
4. Rose et al., *PNAS* 78, 6670 (1981).
5. Yelverton et al., *Science* 219, 614 (1983).
6. Burrell, C. et al., *Nature* 291, 503–506 (1981); Mackay et al., *PNAS* 78, 451–4514 (1981).
7. Fauci, A. et al., *Annals of Internal Medicine* 100, 92 (1984).
8. Marx, J. L., *Science* 224, 475 (1984).
9. Groopman, J. E., *Nature* 308, 769 (1984).
10. Wilson, T., *Biotechnology* p. 682 August (1984).
11. Gallo, R. C. et al., *Science* 724, 500 (1984).
12. Popovic, M. et al., *Science* 224, 497 (1984).
13. Barre-Sinouss, F. et al., *Science* 220, 868 (1983).
14. Vilmer, F. et al., *Lancet* 753, (1984).
15. *Chemical and Engineering News*, 14 Sept. (1984).
16. Sarngadharen, M. G. et al., *Science* 224, 506 (1984).
17. Kitchen, L. W. et al., *Nature* 312, 367 (1984).
18. Bolivar et al., *Gene* 2, 95 (1977).
19. Chang et al., *Nature* 275, 615 (1978).
20. Itakura et al. *Science* 198, 1056 (1977).
21. Goeddel et al., *Nature* 281, 544 (1979).
22. Goeddel et al., *Nucleic Acids Res.* 8, 4057 (1980).
23. European Patent Appln. Publ. No. 036776.
24. Siebenlist et al., *Cell* 20, 269 (1980).
25. Stinchcomb et al., *Nature* 282, 39 (1979).
26. Kingsman et al. *Gene* 7, 141 (1979).
27. Tschemper et al., *Gene* 10, 157 (1980).
28. Jones, *Genetics* 85, 12 (1977).
29. Hitzeman et al., *J. Biol. Chem.* 255, 2073 (1980).
30. Bess et al. *J. Adv. Enzyme Reg.* 7, 149 (1968).
31. Holland et al. *Biochemistry* 17, 4900 (1978).
32. T. Maniatis et al., *Molecular Cloning* (Cold Spring Harbor Press. N.Y. 1982)
33. Mandel et al. *J. Mol. Biol.* 53, 154 (1970).
34. R. Lawn et al. *Nucleic Acids Res.* 9, 6103–6114 (1981).
35. Crea et al., *Proc. Natl. Acad. Sci. USA* 75(12), 5765 (1978).
36. Deleted
37. Wood, N. I., et al., *Nature* 312, 330 (1984).
38. Gray, P. W. et al., *Nature* 295, 503 (1982).
39. Messing, R. et al., *Nucleic Acid Res.* 9, 309–321 (1981).
40. Laemelli, U. *Nature* 227, 680–685 (1970).
41. Hunkapillar, M. et al. in *Methods in Enzymology*, 91, 227–231 (eds. Hirs, C. i Timasheff, S.) Academic Press, N.Y., 1983).
42. Hewick, R. M. et al., *J. Biol. Chem.* 256:7990 (1981).
43. Vieira, J. and Messing, J. *GEM*, 19, 259–268, (1982).
44. McGrath et al., *Nature* 295, 423 (1982).
45. DeBoer, R. et al. in *Promters, Structure and Function* (Praeger Scientific, 1982).
46. Liu, C. et al., *Nature* 309, 82 (1984).
47. Kirid, D., et al., *Science*, 214, 1125–1129 (1981).
48. Gazdar, A. F. et al., *Blood* 55, 409 (1980).
49. Gallo, R. et al., *PNAS*, 77, 7415 (1980).
50. No reference
51. No reference
52. No reference
53. Mitsua, H. et al., *Science* 226, 172 (1984).
54. DeCiccio, *J. Nat. Cancer Institute* 61, 1187 (1978); Verma, B.B.A. 473 (1974).
55a. Kleid, D. et al., *Science* 214, 1125–1129 (1981).
55b. Miozzaro, G. and Yanofsky, C., *J. Bact.* 133, 1457–1466 (1978).
55c. Goeddel, D. et al., *Proc. Natl. Acad. Sci.* 76, 106–110 (1979).
55d. Towbin, H., Staehelin, T. and Gordon, T., *Proc. Natl. Acad. Sci.* 76, 4350–4353 (1979).
55e. Muesing, M. et al., *Nature* 313, 450–458 (1985).
55f. Urlaub, G. and Chasin, L., *Proc. Natl. Acad. Sci.* 77, 4216–4220 (1980).
55g. Graham, F. and van der Eb, A., *Virology* 52, 456–467 (1977).
55h. Wigler, M. et al., *Proc. Natl. Acad. Sci.* 76, 1373–1376 (1979).
55i. Frost, E. and Williams J., *Virology* 91, 39–50 (1978).
55j. Ringold, G., Dieckmann, B. and Lee, F., *J. Mol. Appl. Genet.* 1, 165–175 (1981).
55k. Kaufman, R. and Sharp, P., *J. Mol. Biol.* 159, 601–621 (1982).
55l. Safai, B. et al., *Lancet* I:1438–1440 (1984).
55m. Salahuddin, S. et al., *Lancet* II:1418–1420 (1984).
55n. Barin, F. et al., *Science* 228, 1094–1096 (1985).
55o. Veronese, F. et al., *Science* 229, 1402–1405 (1985).
55p. Robey, W. et al., *Science* 228, 593–595 (1985).
55q. Arya, S., Chan, G., Josephs, S. and Wong-Staal, F., *Science* 229, 69–73 (1985).
55r. Kozak, M., *Nucleic Acids Res.* 9, 5233–5253 (1981).
55s. Liu, C., Simonsen, C. and Levinson, A., *Nature* 309, 82–85 (1984).
56. Rose, D. et al., *Proc. Nat. Acad. Sci. USA*, 78, 6670 (1981).
57. Yelverton, E. et al., *Science* 219, 614 (1983).
58. Voller, A. et al., *Manual of Clinical Imunology* 2d (1980), American Society for Microbiology, pp. 359–371.

What is claimed is:

1. A fusion polypeptide comprising (a) a first polypeptide sequence of an AIDS associated E', env, or gag polypeptide, that specifically binds complementary antibody and (b) a second polypeptide sequence which is not an AIDS associated virus polypeptide.

2. The fusion polypeptide of claim 1 wherein the amino terminus of the first polypeptide sequence is fused to the carboxyl terminus of the second polypeptide sequence.

3. The fusion polypeptide of claim 1 wherein the second polypeptide is a viral antigen.

4. The fusion polypeptide of claim 3 wherein the viral antigen is a herpes simplex antigen.

5. The fusion polypeptide of claim 1 wherein the retrovirus polypeptide is gp 120 or gp 160.

6. The fusion polypeptide of claim 1 wherein the second polypeptide is positioned at the amino terminus, carboxy terminus, or inserted within the AIDS associated polypeptide sequence.

7. The fusion polypeptide of claim 1 wherein the second polypeptide is not capable of inducing an autoimmune response in humans.

8. The fusion of claim 1 wherein the retrovirus polypeptide is an E' sequence.

9. The fusion polypeptide of claim 1 which is unglycosylated.

10. The fusion polypeptide of claim 1, wherein the polypeptide sequence of the AIDS associated E', env, or gag polypeptide is full length.

11. A fusion polypeptide having a herpes simplex virus gD signal peptide sequence fused in reading frame with a polypeptide sequence other than HSV gD.

12. A nucleic acid comprising the fusion polypeptide of claim 11.

13. An expression vector comprising the nucleic acid of claim 12.

14. A host comprising the vector of claim 13.

* * * * *